(12) United States Patent
Luo et al.

(10) Patent No.: US 11,788,124 B2
(45) Date of Patent: Oct. 17, 2023

(54) METHODS TO FURTHER ENHANCE SIGNAL AMPLIFICATION FOR THE IN SITU DETECTION OF NUCLEIC ACIDS

(71) Applicant: ADVANCED CELL DIAGNOSTICS, INC., Newark, CA (US)

(72) Inventors: Yuling Luo, Newark, CA (US); Xiao-Jun Ma, Newark, CA (US); Steve Chen, Newark, CA (US); Nan Su, Newark, CA (US); Emerald Doolittle, Newark, CA (US); Bingqing Zhang, Newark, CA (US); Xiaoming Wang, Newark, CA (US); Xingyong Wu, Newark, CA (US); Xiao Yan Pimentel, Newark, CA (US); Helen Jarnagin, Newark, CA (US)

(73) Assignee: ADVANCED CELL DIAGNOSTICS, INC., Newark, CA (US)

( * ) Notice: Subject to any disclaimer, the term of this patent is extended or adjusted under 35 U.S.C. 154(b) by 316 days.

(21) Appl. No.: 17/046,228

(22) PCT Filed: Apr. 8, 2019

(86) PCT No.: PCT/US2019/026279
§ 371 (c)(1),
(2) Date: Oct. 8, 2020

(87) PCT Pub. No.: WO2019/199643
PCT Pub. Date: Oct. 17, 2019

(65) Prior Publication Data
US 2021/0032690 A1      Feb. 4, 2021

Related U.S. Application Data
(60) Provisional application No. 62/667,237, filed on May 4, 2018, provisional application No. 62/655,143, filed on Apr. 9, 2018.

(51) Int. Cl.
*C07H 21/02* (2006.01)
*C12Q 1/6841* (2018.01)
(Continued)

(52) U.S. Cl.
CPC .......... *C12Q 1/6841* (2013.01); *C12Q 1/682* (2013.01); *C12Q 1/6876* (2013.01); *C12Q 2543/10* (2013.01)

(58) Field of Classification Search
USPC .......... 435/6.1, 6.11, 6.12, 91.1, 91.2, 91.51, 435/183; 436/94, 501; 536/23.1, 24.3,
(Continued)

(56) References Cited

U.S. PATENT DOCUMENTS

| | | | |
|---|---|---|---|
| 3,817,837 | A | 6/1974 | Rubenstein et al. |
| 3,850,752 | A | 11/1974 | Schuurs et al. |

(Continued)

FOREIGN PATENT DOCUMENTS

| | | |
|---|---|---|
| WO | WO 2007/001986 | 1/2007 |
| WO | WO 2007/002006 | 1/2007 |

(Continued)

OTHER PUBLICATIONS

International Search Report and Written Opinion for PCT/US2019/026279, dated Jul. 5, 2019. 29 pages.

(Continued)

*Primary Examiner* — Frank W Lu
(74) *Attorney, Agent, or Firm* — Casimir Jones, S.C.; Peter J. Schlueter

(57) ABSTRACT

The present invention relates to detection of nucleic acids and provides a composition comprising a Signal Generating Complex, wherein the composition comprises: (A) a pair of target probes (TPs), wherein a first TP of the pair of TPs comprises a nucleic acid sequence comprising two segments; (B) a pair of base PPAs comprising the first and
(Continued)

second base PPAs, wherein the first base PPA comprises a nucleic acid sequence comprising three segments; (C) a set of extension PPAs comprising the first and second extension PPAs, wherein the first extension PPA comprises a nucleic acid sequence comprising two segments; (D) a plurality of pre-amplifiers (PAs), wherein the PAs comprise a nucleic acid sequence comprising three segments; (E) a plurality of amplifiers (AMPs), wherein the AMPs comprise a nucleic acid sequence comprising two segments; and (F) a plurality of label probes (LPs), wherein the LPs comprise a nucleic acid sequence comprising two segments.

15 Claims, 9 Drawing Sheets

(51) Int. Cl.
   *C12Q 1/682*      (2018.01)
   *C12Q 1/6876*     (2018.01)
(58) Field of Classification Search
   USPC .............................................. 536/24.33, 25.3
   See application file for complete search history.

(56) References Cited

U.S. PATENT DOCUMENTS

| | | |
|---|---|---|
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,366,241 A | 12/1982 | Tom et al. |
| 5,124,246 A | 6/1992 | Urdea et al. |
| 5,635,352 A | 6/1997 | Urdea et al. |
| 5,681,697 A | 10/1997 | Urdea et al. |
| 5,710,264 A | 1/1998 | Urdea et al. |
| 5,849,481 A | 12/1998 | Urdea et al. |
| 6,465,175 B2 | 10/2002 | Horn et al. |
| 7,399,845 B2 | 7/2008 | Seth et al. |
| 7,709,198 B2 | 5/2010 | Lue et al. |
| 8,658,361 B2 | 2/2014 | Wu et al. |
| 9,315,854 B2 | 4/2016 | Wu et al. |
| 2007/0015188 A1 | 1/2007 | Luo et al. |
| 2008/0038725 A1 | 2/2008 | Luo et al. |
| 2009/0081688 A1 | 3/2009 | Luo et al. |
| 2011/0059442 A1 | 3/2011 | Luo et al. |
| 2011/0059866 A1 | 3/2011 | Luo et al. |
| 2012/0071343 A1 | 3/2012 | Ma et al. |
| 2012/0100540 A1 | 4/2012 | Wu et al. |
| 2012/0214152 A1 | 8/2012 | Ma et al. |
| 2013/0023433 A1 | 1/2013 | Luo et al. |
| 2013/0171621 A1 | 7/2013 | Luo et al. |
| 2013/0294826 A1 | 11/2013 | Chen |
| 2013/0323717 A1 | 12/2013 | Choe et al. |
| 2014/0178869 A1 | 6/2014 | Ma et al. |
| 2014/0249040 A1 | 9/2014 | Wu et al. |
| 2014/0296090 A1 | 10/2014 | Mir et al. |
| 2014/0357509 A1 | 12/2014 | Ma et al. |
| 2015/0045251 A1 | 2/2015 | Wang et al. |
| 2016/0046984 A1 | 2/2016 | Nguyen et al. |
| 2016/0115555 A1 | 4/2016 | Ma et al. |
| 2016/0186245 A1 | 6/2016 | Luo et al. |
| 2016/0201117 A1 | 7/2016 | Wu et al. |
| 2017/0101672 A1 | 4/2017 | Luo et al. |

FOREIGN PATENT DOCUMENTS

| | | |
|---|---|---|
| WO | WO 2012/054795 | 4/2012 |
| WO | WO 2017/004203 | 1/2017 |
| WO | WO 2017/066211 | 4/2017 |

OTHER PUBLICATIONS

Extended European Search Report for 22173719.0, dated Feb. 8, 2022. 7 pages.
Anderson et al., Fully Automated RNAscope In Situ Hybridization Assays for Formalin-Fixed Paraffin-Embedded Cells and Tissues. J Cell Biochem. Oct. 2016;117(10):2201-8.
Ausubel et al., Current Protocols in Molecular Biology, John Wiley and Sons, Baltimore, MD. 2003. TOC only. 15 pages.
Baker et al., Robust RNA-based in situ mutation detection delineates colorectal cancer subclonal evolution. Nat Commun. Dec. 8, 2017;8(1):1998. 1-8.
Baxter et al., Multiparametric characterization of rare HIV-infected cells using an RNA-flow FISH technique. Nat Protoc. Oct. 2017;12(10):2029-2049.
Brown et al., New technologies for cervical cancer screening. Best Pract Res Clin Obstet Gynaecol. Apr. 2012;26(2):233-42.
Cecil Textbook of Medicine, Bennett and Plum, eds., 20th ed., WB Saunders, Philadelphia. 1996. TOC only. 42 pages.
Cervical Cytology Practice Guidelines. Approved by the American Society of Cytopathology (ASC) Executive Board. Acta Cytol. Mar.-Apr. 2001;45(2):201-26.
Colposcopy and Treatment of Cervical Intraepithelial Neoplasia: A Beginner's Manual, Sellors and Sankaranarayanan, eds., International Agency for Research on Cancer, Lyon, France. 2003. 138 pages.
Dey, "Cytology Sample Procurement, Fixation and Processing" in Basic and Advanced Laboratory Techniques in Histopathology and Cytology. Springer, Singapore. 2018. pp. 121-132.
Hanley et al., Detection of low abundance RNA molecules in individual cells by flow cytometry. PLoS One. 2013;8(2):e57002. 8 pages.
Hicks et al., In situ hybridization in the pathology laboratory: general principles, automation, and emerging research applications for tissue-based studies of gene expression. J Mol Histol. Aug. 2004;35(6):595-601.
Kalof et al., Our approach to squamous intraepithelial lesions of the uterine cervix. J Clin Pathol. May 2007;60(5):449-55.
Majlessi et al., Advantages of 2'-O-methyl oligoribonucleotide probes for detecting RNA targets. Nucleic Acids Res. May 1, 1998;26(9):2224-9.
Manafi et al., Fluorogenic and chromogenic substrates used in bacterial diagnostics. Microbiol Rev. Sep. 1991;55(3):335-48.
Non-Gynocological Cytology Practice Guideline. American Society of Cytopathology, Adopted by the ASC executive board Mar. 2, 2004. Acta Cytol. Jul.-Aug. 2004;48(4):521-46.
Petersen et al., LNA: a versatile tool for therapeutics and genomics. Trends Biotechnol. Feb. 2003;21(2):74-81.
Sambrook et al., Molecular Cloning: A Laboratory Manual, Third Ed., Cold Spring Harbor Laboratory, New York. 2001. TOC only. 23 pages.
Santalucia. A unified view of polymer, dumbbell, and oligonucleotide DNA nearest-neighbor thermodynamics. Proc Natl Acad Sci U S A. Feb. 17, 1998;95(4):1460-5.
Stoler. In situ hybridization. Clin Lab Med. Mar. 1990;10(1):215-36.
Wang et al., Characterization of denaturation and renaturation of DNA for DNA hybridization. Environ Health Toxicol. Sep. 11, 2014;29:e2014007. 1-8.
Wang et al., RNAscope: a novel in situ RNA analysis platform for formalin-fixed, paraffin-embedded tissues. J Mol Diagn. Jan. 2012;14(1):22-9.
Waxman et al., Revised terminology for cervical histopathology and its implications for management of high-grade squamous intraepithelial lesions of the cervix. Obstet Gynecol. Dec. 2012;120(6):1465-71.
Wilkinson, ed., In situ hybridization. A practical approach., IRL Press, Oxford. 1992. TOC only. 8 pages.
Yang et al., Artificially expanded genetic information system: a new base pair with an alternative hydrogen bonding pattern. Nucleic Acids Res. 2006:34(21):6095-101.
Hermanson, Bioconjugate Techniques, Academic Press, San Diego. 1996. Table of Contents, Preface, and Acknowledgements, 12 pages.

(56) References Cited

OTHER PUBLICATIONS

Schulz et al., Simultaneous Multiplexed Imaging of mRNA and Proteins with Subcellular Resolution in Breast Cancer Tissue Samples by Mass Cytometry. Cell Syst. Jan. 24, 2018;6(1):25-36.e5.
Shapiro, Practical Flow Cytometry 4th ed., Wiley-Liss, New York. 2003. Table of Contents and Preface only. 47 pages.

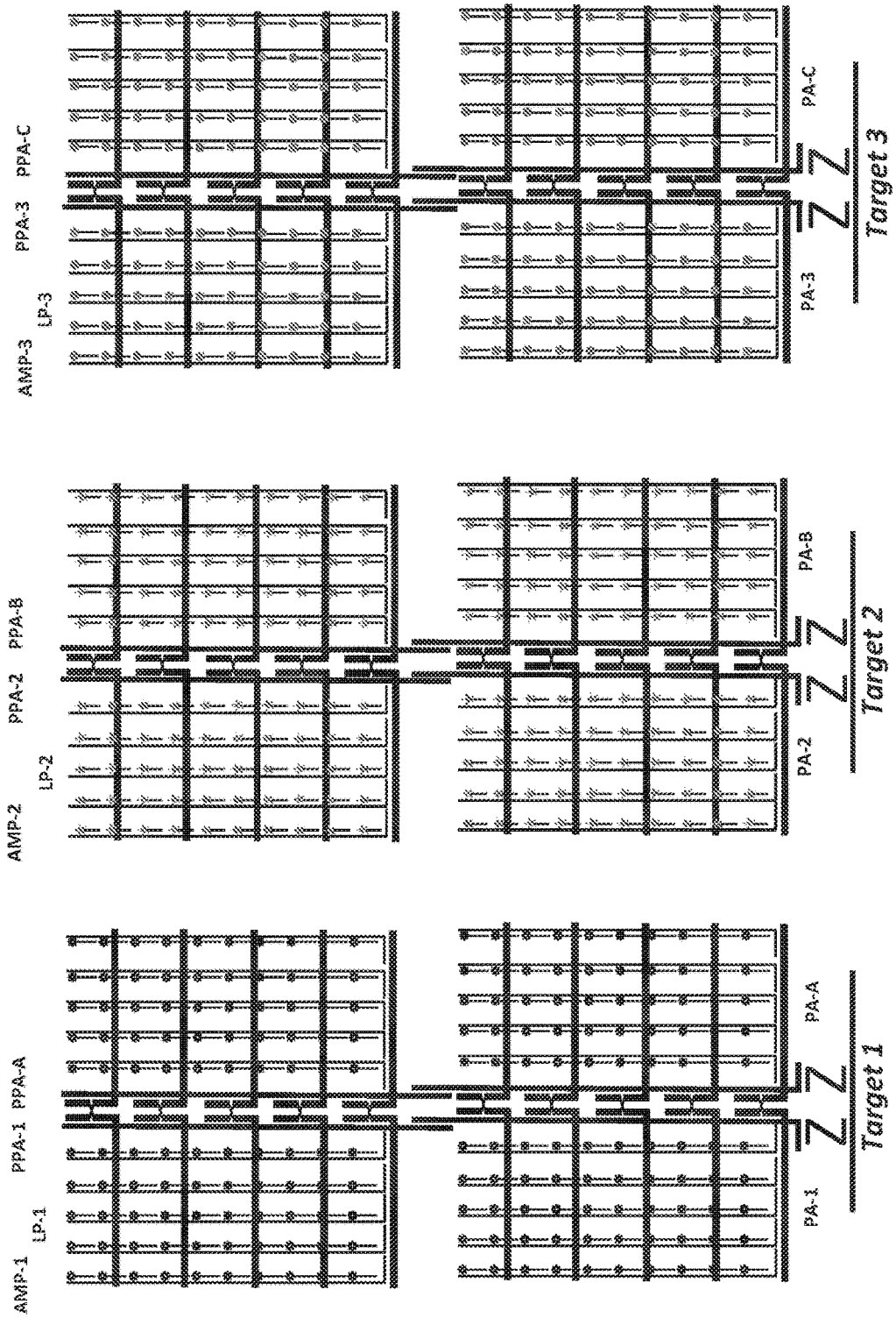

METHODS TO FURTHER ENHANCE SIGNAL AMPLIFICATION FOR THE IN SITU DETECTION OF NUCLEIC ACIDS

This application claims the benefit of U.S. Provisional Application No. 62/655,143, filed Apr. 9, 2018, and U.S. Provisional Application No. 62/667,237, filed May 4, 2018, the entire contents of each of which are incorporated herein by reference.

BACKGROUND OF THE INVENTION

The present invention relates generally to detection of nucleic acids, and more specifically to in situ detection of nucleic acids.

In situ hybridization (ISH) is a technique that allows detection and localization of specific nucleic acid molecules in morphologically preserved individual cells, histological tissue sections, or chromosome preparations. ISH is based on the complementary hybridization of a nucleic acid probe, generally an oligonucleotide, to a specific target nucleic acid, such as DNA or RNA.

ISH detection of nucleic acids is important in life sciences research and in diagnostics because it allows the molecular signals associated with the detected nucleic acid to be mapped to the corresponding cell, which can provide insights into the biological system under study or the disease condition associated with a diagnostic application. An important aspect of using ISH, particularly with detection of low abundance nucleic acids, is to provide a high signal associated with positive detection of a target nucleic acid and low background and non-specific binding probes.

Thus, there exists a need for methods to detect nucleic acid molecules with high sensitivity and specificity. The present invention satisfies this need and provides related advantages as well.

SUMMARY OF INVENTION

In one embodiment, the invention provides a composition comprising a Signal Generating Complex (SGC), wherein the composition comprises: (A) a pair of target probes (TPs), wherein a first TP of the pair of TPs comprises a nucleic acid sequence comprising two segments, (i) a segment comprising a binding site for a first segment of a target nucleic acid, and (ii) a segment comprising a binding site for a first base pre-pre-amplifier (base PPA); and wherein a second TP of the pair of TPs comprises a nucleic acid sequence comprising two segments, (i) a segment comprising a binding site for a second segment of the target nucleic acid, and (ii) a segment comprising a binding site for a second base PPA; (B) a pair of base PPAs comprising the first and second base PPAs, wherein the first base PPA comprises a nucleic acid sequence comprising three segments, (i) a segment that binds to the first base PPA binding site of the first TP, (ii) a segment comprising a plurality of first pre-amplifier binding segment repeats (first PA-BSRs), and (iii) a segment comprising a binding site for a first extension pre-pre-amplifier (extension PPA); and wherein the second base PPA comprises a nucleic acid sequence comprising three segments, (i) a segment that binds to the second base PPA binding site of the second TP, (ii) a segment comprising a plurality of second pre-amplifier binding segment repeats (second PA-BSRs), and (iii) a segment comprising a binding site for a second extension PPA; wherein the first and second PA-BSRs are different sequences, and wherein the segments are in the order (i), (ii), (iii); (C) a set of extension PPAs comprising the first and second extension PPAs, wherein the first extension PPA comprises a nucleic acid sequence comprising two segments, (i) a segment that binds to the first extension PPA binding site of the first base PPA, and (ii) a segment comprising a plurality of the first PA-BSRs; and wherein the second extension PPA comprises a nucleic acid sequence comprising two segments, (i) a segment that binds to the second extension PPA binding site of the second base PPA, and (ii) a segment comprising a plurality of the second PA-BSRs; (D) a plurality of pre-amplifiers (PAs), wherein the PAs comprise a nucleic acid sequence comprising three segments, (i) a segment complementary to the first PA-BSR, (ii) a segment complementary to the second PA-BSR, and (iii) a segment comprising a plurality of amplifier binding segment repeats (AMP-BSRs); wherein the segments are in the order (i), (ii), (iii); (E) a plurality of amplifiers (AMPs), wherein the AMPs comprise a nucleic acid sequence comprising two segments, (i) a segment complementary to the AMP-BSRs, and (ii) a segment comprising a plurality of label probe binding segment repeats (LP-BSRs); and (F) a plurality of label probes (LPs), wherein the LPs comprise a nucleic acid sequence comprising two segments, (i) a segment complementary to the LP-BSRs, and (ii) a segment that is detectable; wherein the respective binding sites and complementary segments are hybridized to form the SGC.

In one embodiment of such a composition, the set of extension PPAs comprises at least one additional first extension PPA and at least one additional second extension PPA, wherein the additional first extension PPA comprises a nucleic acid sequence comprising two segments, (i) a segment comprising a binding site for the first extension PPA, and (ii) a segment comprising a plurality of the first PA-BSRs; wherein the additional second extension PPA comprises a nucleic acid sequence comprising two segments, (i) a segment comprising a binding site for the second extension PPA, and (ii) a segment comprising a plurality of the second PA-BSRs; and wherein the at least one additional first PPA optionally comprises a third segment (iii) comprising a second binding site for the first extension PPAs, and the at least one additional second PPA optionally comprises a third segment (iii) comprising a second binding site for the second extension PPAs, wherein the segments are in the order (i), (ii), (iii).

In one embodiment of such a composition, the binding sites between the first base PPA and the first extension PPA and/or between the extension PPAs comprise complementary sequences, and wherein the binding sites between the second base PPA and the second extension PPA and/or between the second extension PPAs comprise complementary sequences.

In one embodiment of such a composition, the composition further comprises a pair of bridges comprising a first bridge and second bridge, wherein the first bridge comprises two sections that bind to the first extension PPA binding site of the first base PPA and/or the first extension PPA binding site of the first extension PPA; and wherein the second bridge comprises two sections that bind to the second extension PPA binding site of the second base PPA and/or the second extension PPA binding site of the second extension PPA; wherein binding of the bridge tethers the extension PPA to the base PPA and/or the extension PPAs to each other.

In one embodiment of such a composition, the composition further comprises a pair of bridges comprising a first bridge and second bridge, wherein the first bridge comprises two sections, (i) a section that binds to the first extension PPA binding site of the first base PPA and/or the first extension PPA binding site of the first extension PPA, and (ii) a section that binds to the second extension PPA binding site of the second extension PPA; wherein the second bridge comprises two sections, (i) a section that binds to the second extension PPA binding site of the second base PPA and/or the second extension PPA binding site of the second extension PPA, and (ii) a section that binds to the first extension PPA binding site of the first extension PPA; wherein binding of the bridge tethers the second extension PPA to the first base PPA or the second extension PPA to the first extension PPA, and tethers the first extension PPA to the second base PPA or the first extension PPA to the second extension PPA.

In one embodiment of such a composition, the first base PPA and/or the first extension PPA comprises a fourth segment (iv) comprising a binding site for the second extension PPA, and wherein the second base PPA and/or the second extension PPA comprises a fourth segment (iv) comprising a binding site for the first extension PPA, wherein the segments of the PPA are in the order (i), (ii), (iv), (iii).

In another embodiment, the invention provides a composition comprising a Signal Generating Complex (SGC), wherein the composition comprises (A) a pair of target probes (TPs), wherein a first TP of the pair of TPs comprises a nucleic acid sequence comprising two segments, (i) a segment comprising a binding site for a first segment of a target nucleic acid, and (ii) a segment comprising a binding site for a first pre-pre-amplifier (PPA); and wherein a second TP of the pair of TPs comprises a nucleic acid sequence comprising two segments, (i) a segment comprising a binding site for a second segment of the target nucleic acid, and (ii) a segment comprising a binding site for a second PPA; (B) a pair of PPAs comprising the first and second PPAs, wherein the first PPA comprises a nucleic acid sequence comprising two segments, (i) a segment that binds to the first PPA binding site of the first TP, and (ii) a segment comprising a plurality of first pre-amplifier binding segment repeats (first PA-BSRs); and wherein the second PPA comprises a nucleic acid sequence comprising two segments, (i) a segment that binds to the second PPA binding site of the second TP, and (ii) a segment comprising a plurality of second PA-BSRs, wherein the first and second PA-BSRs are different sequences; (C) a plurality of base pre-amplifiers (base PAs), wherein the base PAs comprise a nucleic acid sequence comprising four segments (i) a segment complementary to the first PA-BSRs, (ii) a segment complementary to the second PA-BSRs, (iii) a segment comprising a plurality of amplifier binding segment repeats (AMP-BSRs), and (iv) a segment that binds to an extension pre-amplifier (extension PA), wherein the segments are in the order (i), (ii), (iii), (iv); (D) a plurality of extension PAs, wherein the extension PAs comprise a nucleic acid sequence comprising two segments (i) a segment that binds to the extension PA binding site of the base PAs and (ii) a plurality of amplifier binding segment repeats (AMP-BSRs); and wherein the extension PAs optionally comprise a third segment (iii) comprising a binding site for the extension PAs, wherein the segments are in the order (i), (ii), (iii); (E) a plurality of amplifiers (AMPs), wherein the AMPS comprise a nucleic acid sequence comprising two segments, (i) a segment complementary to the AMP-BSRs, and (ii) a segment comprising a plurality of label probe binding segment repeats (LP-BSRs); and (F) a plurality of label probes (LPs), wherein the LPs comprise a nucleic acid sequence comprising two segments, (i) a segment complementary to the LP-BSRs, and (ii) a segment that is detectable; wherein the respective binding sites and complementary segments are hybridized to form the SGC.

In one embodiment of such a composition, the binding sites between the base PAs and the extension PAs comprise complementary sequences. In one embodiment of such a composition, the composition further comprises a bridge, wherein the bridge comprises two sections that bind to the extension PA binding site of the base PA and/or the extension PA binding site of the extension PA, wherein binding of the bridge tethers the extension PA to the base PA and/or the extension PAs to each other.

In another embodiment, the invention provides a composition comprising a Signal Generating Complex (SGC), wherein the composition comprises (A) a pair of target probes (TPs), wherein a first TP of the pair of TPs comprises a nucleic acid sequence comprising two segments, (i) a segment comprising a binding site for a first segment of a target nucleic acid, and (ii) a segment comprising a binding site for a first pre-pre-amplifier (PPA); and wherein a second TP of the pair of TPs comprises a nucleic acid sequence comprising two segments, (i) a segment comprising a binding site for a second segment of the target nucleic acid, and (ii) a segment comprising a binding site for a second PPA; (B) a pair of PPAs comprising the first and second PPAs, wherein the first PPA comprises a nucleic acid sequence comprising two segments, (i) a segment that binds to the first PPA binding site of the first TP, and (ii) a segment comprising a plurality of first pre-amplifier binding segment repeats (first PA-BSRs); and wherein the second PPA comprises a nucleic acid sequence comprising two segments, (i) a segment that binds to the second PPA binding site of the second TP, and (ii) a segment comprising a plurality of second PA-BSRs, wherein the first and second PA-BSRs are different sequences; (C) a plurality of pre-amplifiers (PAs), wherein the PAs comprise a nucleic acid sequence comprising three segments, (i) a segment complementary to the first PA-BSR, (ii) a segment complementary to the second PA-BSR, and (iii) a segment comprising a plurality of amplifier binding segment repeats (AMP-BSRs); wherein the segments are in the order (i), (ii), (iii); (D) a plurality of base amplifiers (base AMPs), wherein the base AMPs comprise a nucleic acid sequence comprising three segments (i) a segment complementary to the AMP-BSRs, (ii) a segment comprising a plurality of label probe binding segment repeats (LP-BSRs), and (iii) a segment that binds to an extension amplifier (extension AMP), in the order (i), (ii), (iii); (E) a plurality of extension AMPs, wherein the extension AMPs comprise a nucleic acid sequence comprising two segments (i) a segment that binds to the extension AMP binding site of the base AMP, and (ii) a segment comprising a plurality of label probe binding segment repeats (LP-BSRs); and wherein the extension AMPs optionally comprise a third segment (iii) comprising a binding site for the extension PAs, wherein the segments are in the order (i), (ii), (iii); (F) a plurality of label probes (LPs), wherein the LPs comprise a nucleic acid sequence comprising two segments (i) a segment complementary to the LP-BSRs, and (ii) a segment that is detectable; wherein the respective binding sites and complementary segments are hybridized to form the SGC.

In one embodiment of such a composition, the binding sites between the base AMPs and the extension AMPs comprise complementary sequences. In one embodiment of such a composition, the composition further comprises a bridge, wherein the bridge comprises two sections that bind to the extension AMP binding site of the base AMP and/or the extension AMP binding site of the extension AMP, wherein binding of the bridge tethers the extension AMP to the base AMP and/or the extension AMPs to each other.

In some embodiments of compositions of the invention, (I) the first TP further comprises a third segment (iii) comprising a binding site for the second PPA; wherein the second TP further comprise a third segment (iii) comprising a binding site for the first PPA; and wherein the segments are in the order (i), (iii), (ii); and (II) the first base PPA further comprises a fourth segment (iv) comprising a binding site for the second TP; wherein the second base PPA further comprises a fourth segment (iv) comprising a binding site for the first TP; wherein the segments are in the order (iv), (i), (ii), (iii); or wherein the first PPA further comprises a third segment (iii) comprising a binding site for the second TP; wherein the second PPA further comprises a third segment (iii) comprising a binding site for the first TP; wherein the segments are in the order (iii), (i), (ii).

In another embodiment, the invention provides a composition comprising a Signal Generating Complex (SGC), wherein the composition comprises (A) a pair of target probes (TPs), wherein a first TP of the pair of TPs comprises a nucleic acid sequence comprising two segments, (i) a segment comprising a binding site for a first segment of a target nucleic acid, and (ii) a segment comprising a binding site for a first base pre-pre-amplifier (base PPA); and wherein a second TP of the pair of TPs comprises a nucleic acid sequence comprising two segments, (i) a segment comprising a binding site for a second segment of the target nucleic acid, and (ii) a segment comprising a binding site for a second base PPA; (B) a pair of PPAs comprising the first and second PPAs, wherein the first PPA comprises a nucleic acid sequence comprising two segments, (i) a segment that binds to the first PPA binding site of the first TP, and (ii) a segment comprising a plurality of first pre-amplifier binding segment repeats (first PA-BSRs), wherein the first PA-BSRs comprise two segments, (ia) a segment comprising a binding site for a first pre-amplifier (first PA) and (ib) a segment comprising a binding site for a second PA, wherein the segments of the first PPA are in the order (i), (ia), (ib); and wherein the second PPA comprises a nucleic acid sequence comprising two segments, (i) a segment that binds to the second PPA binding site of the second TP, and (ii) a segment comprising a plurality of second PA-BSRs, wherein the second PA-BSRs comprise two segments, (iia) a segment comprising a binding site for the second PA and (iib) a segment comprising a binding site for the first PA, wherein the segments of the second PPA are in the order (i), (iia), (iib); (C) a plurality of the first PAs and the second PAs, wherein the first PAs comprise a nucleic acid sequence comprising three segments, (i) a segment complementary to the second PA-BSR, (ii) a segment complementary to the first PA-BSR, and (iii) a segment comprising a plurality of amplifier binding segment repeats (AMP-BSRs); and wherein the second PAs comprise a nucleic acid sequence comprising three segments, (i) a segment complementary to the first PA-BSR, (ii) a segment complementary to the second PA-BSR, and (iii) a segment comprising a plurality of amplifier binding segment repeats (AMP-BSRs); (D) a plurality of amplifiers (AMPs), wherein the AMPs comprise a nucleic acid sequence comprising two segments, (i) a segment complementary to the AMP-BSRs, and (ii) a segment comprising a plurality of label probe binding segment repeats (LP-BSRs); and (E) a plurality of label probes (LPs), wherein the LPs comprise a nucleic acid sequence comprising two segments, (i) a segment complementary to the LP-BSRs, and (ii) a segment that is detectable; wherein the respective binding sites and complementary segments are hybridized to form the SGC.

In one embodiment of such a composition, the PPAs comprise base PPAs and extension PPAs. In one embodiment of such a composition, the PAs comprise base PAs and extension PAs. In one embodiment of such a composition, the AMPs comprise base AMPs and extension AMPs.

In some embodiments of such compositions, the base and extension molecules are tethered by a configuration comprising: wherein the binding sites between the first base PPA and the first extension PPA and/or between the first extension PPAs comprise complementary sequences, and wherein the binding sites between the second base PPA and the second extension PPA and/or between the second extension PPAs comprise complementary sequences; and/or wherein the binding sites between the base PA and extension PA, and or the binding sites between the base AMP and extension AMP comprise complementary sequences.

In some embodiments of such compositions, the base and extension molecules are tethered by a configuration comprising wherein the composition further comprises a pair of bridges comprising a first bridge and second bridge, wherein the first bridge comprises two sections that bind to the first extension PPA binding site of the first base PPA and/or the first extension PPA binding site of the first extension PPA; and wherein the second bridge comprises two sections that bind to the second extension PPA binding site of the second base PPA and/or the second extension PPA binding site of the second extension PPA; wherein binding of the bridge tethers the extension PPA to the base PPA and/or the extension PPAs to each other; or wherein the composition further comprises a bridge, wherein the bridge comprises two sections that bind to the extension PA or AMP binding site of the base PA or AMP and/or the extension PA or AMP binding site of the extension PA or AMP, wherein binding of the bridge tethers the extension PA or AMP to the base PA or AMP and/or the extension PAs or AMPs to each other.

In some embodiments of such compositions, the base and extension molecules are tethered by a configuration comprising wherein the composition further comprises a pair of bridges comprising a first bridge and second bridge, wherein the first bridge comprises two sections, (i) a section that binds to the first extension PPA binding site of the first base PPA and/or the first extension PPA binding site of the first extension PPA, and (ii) a section that binds to the second extension PPA binding site of the second extension PPA; wherein the second bridge comprises two sections, (i) a section that binds to the second extension PPA binding site of the second base PPA and/or the second extension PPA binding site of the second extension PPA, and (ii) a section that binds to the first extension PPA binding site of the first extension PPA; wherein binding of the bridge tethers the second extension PPA to the first base PPA or the second extension PPA to the first extension PPA, and tethers the first extension PPA to the second base PPA or the first extension PPA to the second extension PPA.

In some embodiments of such compositions, the base and extension molecules are tethered by a configuration comprising wherein the first base PPA and/or the first extension PPA comprises a fourth segment (iv) comprising a binding site for the second extension PPA, and wherein the second base PPA and/or the second extension PPA comprises a fourth segment (iv) comprising a binding site for the first extension PPA, wherein the segments of the PPA are in the order (i), (ii), (iv), (iii).

In some embodiments of such compositions, (I) the first TP further comprises a third segment (iii) comprising a binding site for the second PPA; wherein the second TP further comprise a third segment (iii) comprising a binding site for the first PPA; and wherein the segments are in the order (i), (iii), (ii); and (II) the first base PPA further comprises a fourth segment (iv) comprising a binding site for the second TP; wherein the second base PPA further comprises a fourth segment (iv) comprising a binding site for the first TP; wherein the segments are in the order (iv), (i), (ii), (iii); or the first PPA further comprises a third segment (iii) comprising a binding site for the second TP; wherein the second PPA further comprises a third segment (iii) comprising a binding site for the first TP; wherein the segments are in the order (iii), (i), (ii).

In some embodiments of compositions of the invention, the composition further comprises a second SGC, wherein the second SGC comprises a second target that is different from the first target, wherein the SGC comprises an SGC configuration for the second target is independent of the configuration of the first SGC, and wherein the second SGC is distinguishable from the first SGC. In such a composition, the composition can further comprise a third SGC, wherein the third SGC comprises a third target that is different from the first and second targets, wherein the SGC comprises an SGC configuration that is independent of the configuration of the first SGC and/or the second SGC, and wherein the third SGC is distinguishable from the first and second SGC.

In one embodiment, the compositions of the invention comprise a target nucleic acid to which the pair of TPs bind. In one embodiment, the composition of the invention further comprises a cell.

In one embodiment, the invention provides a method of detecting a target nucleic acid, comprising contacting a sample nucleic acid with the components for assembly of an SGC as in the compositions described above, assembling an SGC on the target nucleic acid, and detecting the target nucleic acid. In one embodiment of such a method, the nucleic acid is in a cell.

In one embodiment, the invention provides a kit comprising the components for assembling an SGC, wherein the kit comprises the PPAs, PAs, AMPs, and LPs of any of the compositions described above. In one embodiment of such a kit, the kit further comprises the TPs of any one of compositions described above.

In one embodiment, the invention provides a sample of fixed and permeabilized cells comprising an assembled SGC of any of the compositions described above.

In one embodiment, the invention provides a slide having immobilized thereon a plurality of fixed and permeabilized cells comprising at least one fixed and permeabilized cell containing a target nucleic acid and an assembled SGC of any of the compositions described above.

In one embodiment, the invention provides a composition comprising a Signal Generating Complex (SGC), wherein the composition comprises: (A) a pair of target probes (TPs), wherein a first TP of the pair of TPs comprises a nucleic acid sequence comprising two segments, (i) a segment comprising a binding site for a first segment of a target nucleic acid, and (ii) a segment comprising a binding site for a first base pre-pre-amplifier (base PPA); and wherein a second TP of the pair of TPs comprises a nucleic acid sequence comprising two segments, (i) a segment comprising a binding site for a second segment of the target nucleic acid, and (ii) a segment comprising a binding site for a second base PPA; (B) a pair of base PPAs comprising the first and second base PPAs, wherein the first base PPA comprises a nucleic acid sequence comprising three segments, (i) a segment that binds to the first base PPA binding site of the first TP, (ii) a segment comprising a plurality of first pre-amplifier binding segment repeats (first PA-BSRs), and (iii) a segment comprising a binding site for a first extension pre-pre-amplifier (extension PPA); and wherein the second base PPA comprises a nucleic acid sequence comprising three segments, (i) a segment that binds to the second base PPA binding site of the second TP, (ii) a segment comprising a plurality of second pre-amplifier binding segment repeats (second PA-BSRs), and (iii) a segment comprising a binding site for a second extension PPA; wherein the first and second PA-BSRs are different sequences; (C) a set of extension PPAs comprising the first and second extension PPAs, wherein the first extension PPA comprises a nucleic acid sequence comprising two segments, (i) a segment that binds to the first extension PPA binding site of the first base PPA, and (ii) a segment comprising a plurality of the first PA-BSRs; and wherein the second extension PPA comprises a nucleic acid sequence comprising two segments, (i) a segment that binds to the second extension PPA binding site of the second base PPA, and (ii) a segment comprising a plurality of the second PA-BSRs; (D) a plurality of pre-amplifiers (PAs), wherein the PAs comprise a nucleic acid sequence comprising three segments, (i) a segment complementary to the first PA-BSR, (ii) a segment complementary to the second PA-BSR, and (iii) a segment comprising a plurality of amplifier binding segment repeats (AMP-BSRs); (E) a plurality of amplifiers (AMPs), wherein the AMPs comprise a nucleic acid sequence comprising two segments, (i) a segment complementary to the AMP-BSRs, and (ii) a segment comprising a plurality of label probe binding segment repeats (LP-BSRs); and (F) a plurality of label probes (LPs), wherein the LPs comprise a nucleic acid sequence comprising two segments, (i) a segment complementary to the LP-BSRs, and (ii) a segment that is detectable; wherein the respective binding sites and complementary segments are hybridized to form the SGC.

In one embodiment of such a composition, the set of extension PPAs comprises at least one additional first extension PPA and at least one additional second extension PPA, wherein the additional first extension PPA comprises a nucleic acid sequence comprising two segments, (i) a segment comprising a binding site for the first extension PPA, and (ii) a segment comprising a plurality of the first PA-BSRs; wherein the additional second extension PPA comprises a nucleic acid sequence comprising two segments, (i) a segment comprising a binding site for the second extension PPA, and (ii) a segment comprising a plurality of the second PA-BSRs; and wherein the at least one additional first PPA optionally comprises a third segment (iii) comprising a second binding site for the first extension PPAs, and the at least one additional second PPA optionally comprises a third segment (iii) comprising a second binding site for the second extension PPAs.

In one embodiment of such a composition, the binding sites between the first base PPA and the first extension PPA and/or between the extension PPAs comprise complementary sequences, and wherein the binding sites between the second base PPA and the second extension PPA and/or between the second extension PPAs comprise complementary sequences.

In one embodiment, the composition further comprises a pair of bridges comprising a first bridge and second bridge, wherein the first bridge comprises two sections that bind to the first extension PPA binding site of the first base PPA and/or the first extension PPA binding site of the first extension PPA; and wherein the second bridge comprises two sections that bind to the second extension PPA binding site of the second base PPA and/or the second extension PPA binding site of the second extension PPA; wherein binding of the bridge tethers the extension PPA to the base PPA and/or the extension PPAs to each other.

In one embodiment, the composition further comprises a pair of bridges comprising a first bridge and second bridge, wherein the first bridge comprises two sections, (i) a section that binds to the first extension PPA binding site of the first base PPA and/or the first extension PPA binding site of the first extension PPA, and (ii) a section that binds to the second extension PPA binding site of the second extension PPA; wherein the second bridge comprises two sections, (i) a section that binds to the second extension PPA binding site of the second base PPA and/or the second extension PPA binding site of the second extension PPA, and (ii) a section that binds to the first extension PPA binding site of the first extension PPA; wherein binding of the bridge tethers the second extension PPA to the first base PPA or the second extension PPA to the first extension PPA, and tethers the first extension PPA to the second base PPA or the first extension PPA to the second extension PPA.

In one embodiment of such a composition, the first base PPA and/or the first extension PPA comprises a fourth segment (iv) comprising a binding site for the second extension PPA, and wherein the second base PPA and/or the second extension PPA comprises a fourth segment (iv) comprising a binding site for the first extension PPA.

In another embodiment, the invention provides a composition comprising a Signal Generating Complex (SGC), wherein the composition comprises: (A) a pair of target probes (TPs), wherein a first TP of the pair of TPs comprises a nucleic acid sequence comprising two segments, (i) a segment comprising a binding site for a first segment of a target nucleic acid, and (ii) a segment comprising a binding site for a first pre-pre-amplifier (PPA); and wherein a second TP of the pair of TPs comprises a nucleic acid sequence comprising two segments, (i) a segment comprising a binding site for a second segment of the target nucleic acid, and (ii) a segment comprising a binding site for a second PPA; (B) a pair of PPAs comprising the first and second PPAs, wherein the first PPA comprises a nucleic acid sequence comprising two segments, (i) a segment that binds to the first PPA binding site of the first TP, and (ii) a segment comprising a plurality of first pre-amplifier binding segment repeats (first PA-BSRs); and wherein the second PPA comprises a nucleic acid sequence comprising two segments, (i) a segment that binds to the second PPA binding site of the second TP, and (ii) a segment comprising a plurality of second PA-BSRs, wherein the first and second PA-BSRs are different sequences; (C) a plurality of base pre-amplifiers (base PAs), wherein the base PAs comprise a nucleic acid sequence comprising four segments (i) a segment complementary to the first PA-BSRs, (ii) a segment complementary to the second PA-BSRs, (iii) a segment comprising a plurality of amplifier binding segment repeats (AMP-BSRs), and (iv) a segment that binds to an extension pre-amplifier (extension PA); (D) a plurality of extension PAs, wherein the extension PAs comprise a nucleic acid sequence comprising two segments (i) a segment that binds to the extension PA binding site of the base PAs and (ii) a plurality of amplifier binding segment repeats (AMP-BSRs); and wherein the extension PAs optionally comprise a third segment (iii) comprising a binding site for the extension PAs; (E) a plurality of amplifiers (AMPs), wherein the AMPS comprise a nucleic acid sequence comprising two segments, (i) a segment complementary to the AMP-BSRs, and (ii) a segment comprising a plurality of label probe binding segment repeats (LP-BSRs); and (F) a plurality of label probes (LPs), wherein the LPs comprise a nucleic acid sequence comprising two segments, (i) a segment complementary to the LP-BSRs, and (ii) a segment that is detectable; wherein the respective binding sites and complementary segments are hybridized to form the SGC.

In one embodiment of such a composition, the binding sites between the base PAs and the extension PAs comprise complementary sequences.

In one embodiment, the composition further comprises a bridge, wherein the bridge comprises two sections that bind to the extension PA binding site of the base PA and/or the extension PA binding site of the extension PA, wherein binding of the bridge tethers the extension PA to the base PA and/or the extension PAs to each other.

In another embodiment, the invention provides a composition comprising a Signal Generating Complex (SGC), wherein the composition comprises: (A) a pair of target probes (TPs), wherein a first TP of the pair of TPs comprises a nucleic acid sequence comprising two segments, (i) a segment comprising a binding site for a first segment of a target nucleic acid, and (ii) a segment comprising a binding site for a first pre-pre-amplifier (PPA); and wherein a second TP of the pair of TPs comprises a nucleic acid sequence comprising two segments, (i) a segment comprising a binding site for a second segment of the target nucleic acid, and (ii) a segment comprising a binding site for a second PPA; (B) a pair of PPAs comprising the first and second PPAs, wherein the first PPA comprises a nucleic acid sequence comprising two segments, (i) a segment that binds to the first PPA binding site of the first TP, and (ii) a segment comprising a plurality of first pre-amplifier binding segment repeats (first PA-BSRs); and wherein the second PPA comprises a nucleic acid sequence comprising two segments, (i) a segment that binds to the second PPA binding site of the second TP, and (ii) a segment comprising a plurality of second PA-BSRs, wherein the first and second PA-BSRs are different sequences; (C) a plurality of pre-amplifiers (PAs), wherein the PAs comprise a nucleic acid sequence comprising three segments, (i) a segment complementary to the first PA-BSR, (ii) a segment complementary to the second PA-BSR, and (iii) a segment comprising a plurality of amplifier binding segment repeats (AMP-BSRs); (D) a plurality of base amplifiers (base AMPs), wherein the base AMPs comprise a nucleic acid sequence comprising three segments (i) a segment complementary to the AMP-BSRs, (ii) a segment comprising a plurality of label probe binding segment repeats (LP-BSRs), and (iii) a segment that binds to an extension amplifier (extension AMP); (E) a plurality of extension AMPs, wherein the extension AMPs comprise a nucleic acid sequence comprising two segments (i) a segment that binds to the extension AMP binding site of the base AMP, and (ii) a segment comprising a plurality of label probe binding segment repeats (LP-BSRs); and wherein the extension AMPs optionally comprise a third segment (iii) comprising a binding site for the extension PAs; (F) a plurality of label probes (LPs), wherein the LPs comprise a nucleic acid sequence comprising two segments (i) a segment complementary to the LP-BSRs, and (ii) a segment that is detectable; wherein the respective binding sites and complementary segments are hybridized to form the SGC.

In one embodiment of such a composition, the binding sites between the base AMPs and the extension AMPs comprise complementary sequences.

In one embodiment, the composition further comprises a bridge, wherein the bridge comprises two sections that bind to the extension AMP binding site of the base AMP and/or the extension AMP binding site of the extension AMP, wherein binding of the bridge tethers the extension AMP to the base AMP and/or the extension AMPs to each other.

In one embodiment of a composition of the invention, (I) wherein the first TP further comprises a third segment (iii) comprising a binding site for the second PPA; wherein the second TP further comprise a third segment (iii) comprising a binding site for the first PPA; and (II) wherein the first base PPA further comprises a fourth segment (iv) comprising a binding site for the second TP; wherein the second base PPA further comprises a fourth segment (iv) comprising a binding site for the first TP; or wherein the first PPA further comprises a third segment (iii) comprising a binding site for the second TP; wherein the second PPA further comprises a third segment (iii) comprising a binding site for the first TP.

In another embodiment, the invention provides a composition comprising a Signal Generating Complex (SGC), wherein the composition comprises: (A) a pair of target probes (TPs), wherein a first TP of the pair of TPs comprises a nucleic acid sequence comprising two segments, (i) a segment comprising a binding site for a first segment of a target nucleic acid, and (ii) a segment comprising a binding site for a first base pre-pre-amplifier (base PPA); and wherein a second TP of the pair of TPs comprises a nucleic acid sequence comprising two segments, (i) a segment comprising a binding site for a second segment of the target nucleic acid, and (ii) a segment comprising a binding site for a second base PPA; (B) a pair of PPAs comprising the first and second PPAs, wherein the first PPA comprises a nucleic acid sequence comprising two segments, (i) a segment that binds to the first PPA binding site of the first TP, and (ii) a segment comprising a plurality of first pre-amplifier binding segment repeats (first PA-BSRs), wherein the first PA-BSRs comprise two segments, (ia) a segment comprising a binding site for a first pre-amplifier (first PA) and (ib) a segment comprising a binding site for a second PA; and wherein the second PPA comprises a nucleic acid sequence comprising two segments, (i) a segment that binds to the second PPA binding site of the second TP, and (ii) a segment comprising a plurality of second PA-BSRs, wherein the second PA-BSRs comprise two segments, (iia) a segment comprising a binding site for the second PA and (iib) a segment comprising a binding site for the first PA; (C) a plurality of the first PAs and the second PAs, wherein the first PAs comprise a nucleic acid sequence comprising three segments, (i) a segment complementary to the second PA-BSR, (ii) a segment complementary to the first PA-BSR, and (iii) a segment comprising a plurality of amplifier binding segment repeats (AMP-BSRs); and wherein the second PAs comprise a nucleic acid sequence comprising three segments, (i) a segment complementary to the first PA-BSR, (ii) a segment complementary to the second PA-BSR, and (iii) a segment comprising a plurality of amplifier binding segment repeats (AMP-BSRs); (D) a plurality of amplifiers (AMPs), wherein the AMPs comprise a nucleic acid sequence comprising two segments, (i) a segment complementary to the AMP-BSRs, and (ii) a segment comprising a plurality of label probe binding segment repeats (LP-BSRs); and (E) a plurality of label probes (LPs), wherein the LPs comprise a nucleic acid sequence comprising two segments, (i) a segment complementary to the LP-BSRs, and (ii) a segment that is detectable; wherein the respective binding sites and complementary segments are hybridized to form the SGC.

In one embodiment of such a composition, the PPAs comprise base PPAs and extension PPAs. In one embodiment of such a composition, the PAs comprise base PAs and extension PAs. In one embodiment of such a composition, the AMPs comprise base AMPs and extension AMPs.

In one embodiment of such a composition, the base and extension molecules are tethered by a configuration comprising: wherein the binding sites between the first base PPA and the first extension PPA and/or between the first extension PPAs comprise complementary sequences, and wherein the binding sites between the second base PPA and the second extension PPA and/or between the second extension PPAs comprise complementary sequences; and/or wherein the binding sites between the base PA and extension PA, and or the binding sites between the base AMP and extension AMP comprise complementary sequences.

In one embodiment of such a composition, the base and extension molecules are tethered by a configuration comprising: wherein the composition further comprises a pair of bridges comprising a first bridge and second bridge, wherein the first bridge comprises two sections that bind to the first extension PPA binding site of the first base PPA and/or the first extension PPA binding site of the first extension PPA; and wherein the second bridge comprises two sections that bind to the second extension PPA binding site of the second base PPA and/or the second extension PPA binding site of the second extension PPA; wherein binding of the bridge tethers the extension PPA to the base PPA and/or the extension PPAs to each other; or wherein the composition further comprises a bridge, wherein the bridge comprises two sections that bind to the extension PA or AMP binding site of the base PA or AMP and/or the extension PA or AMP binding site of the extension PA or AMP, wherein binding of the bridge tethers the extension PA or AMP to the base PA or AMP and/or the extension PAs or AMPs to each other.

In one embodiment of such a composition, the base and extension molecules are tethered by a configuration comprising: wherein the composition further comprises a pair of bridges comprising a first bridge and second bridge, wherein the first bridge comprises two sections, (i) a section that binds to the first extension PPA binding site of the first base PPA and/or the first extension PPA binding site of the first extension PPA, and (ii) a section that binds to the second extension PPA binding site of the second extension PPA; wherein the second bridge comprises two sections, (i) a section that binds to the second extension PPA binding site of the second base PPA and/or the second extension PPA binding site of the second extension PPA, and (ii) a section that binds to the first extension PPA binding site of the first extension PPA; wherein binding of the bridge tethers the second extension PPA to the first base PPA or the second extension PPA to the first extension PPA, and tethers the first extension PPA to the second base PPA or the first extension PPA to the second extension PPA.

In one embodiment of such a composition, the base and extension molecules are tethered by a configuration comprising: wherein the first base PPA and/or the first extension PPA comprises a fourth segment (iv) comprising a binding site for the second extension PPA, and wherein the second base PPA and/or the second extension PPA comprises a fourth segment (iv) comprising a binding site for the first extension PPA.

In one embodiment of such a composition, (I) wherein the first TP further comprises a third segment (iii) comprising a binding site for the second PPA; wherein the second TP further comprise a third segment (iii) comprising a binding site for the first PPA; and (II) wherein the first base PPA further comprises a fourth segment (iv) comprising a binding site for the second TP; wherein the second base PPA further comprises a fourth segment (iv) comprising a binding site for the first TP; or wherein the first PPA further comprises a third segment (iii) comprising a binding site for the second TP; wherein the second PPA further comprises a third segment (iii) comprising a binding site for the first TP.

In one embodiment, the composition further comprises a second SGC, wherein the second SGC comprises a second target that is different from the first target of the compositions described above, wherein the SGC comprises an SGC configuration of any of the compositions described above independently of the configuration of the first SGC, and wherein the second SGC is distinguishable from the first SGC.

In one embodiment, the composition further comprises a third SGC, wherein the third SGC comprises a third target that is different from the first target of the compositions described above and the second target, wherein the SGC comprises an SGC configuration of the compositions described above independently of the configuration of the first SGC and/or the second SGC, and wherein the third SGC is distinguishable from the first and second SGC.

In one embodiment, the composition comprises a target nucleic acid to which the pair of TPs bind. In one embodiment, the composition further comprises a cell, for example, a cell comprising the target nucleic acid(s).

In another embodiment, the inventions provides a method of detecting a target nucleic acid, comprising contacting a sample nucleic acid with the components for assembly of an SGC as in any of the compositions described above, assembling an SGC on the target nucleic acid, and detecting the target nucleic acid. In one embodiment of such a method, the nucleic acid is in a cell.

In another embodiment, the invention provides a kit comprising the components for assembling an SGC, wherein the kit comprises the PPAs, PAs, AMPs, and LPs of any of the compositions described above. In one embodiment, the kit further comprises the TPs of any one of compositions described above.

In another embodiment, the invention provides a sample of cells comprising an assembled SGC of any one of the compositions described above. The cells can optionally be fixed and/or permeabilized.

In another embodiment, the invention provides a slide having immobilized thereon a plurality of cells comprising at least one cell containing a target nucleic acid and an assembled SGC of any of the compositions described above. The cells can optionally be fixed and/or permeabilized.

BRIEF DESCRIPTION OF THE DRAWINGS

FIG. 6 shows exemplary embodiments of multiplex detection of nucleic acids.

DETAILED DESCRIPTION OF THE INVENTION

The present invention relates to the application of methods to increase the signal-to-noise ratio in a sample in which nucleic acids are being detected. The methods utilize tiers or layers of amplification molecules to increase the signal associated with a detected nucleic acid, while at the same time components of the amplification layers are configured to decrease false positives, thereby increasing the signal-to-noise ratio. The amplification layers can comprise pre-pre-amplifiers (PPAs), pre-amplifiers (PAs), and amplifiers (AMPs), as described herein.

Figure 1A:
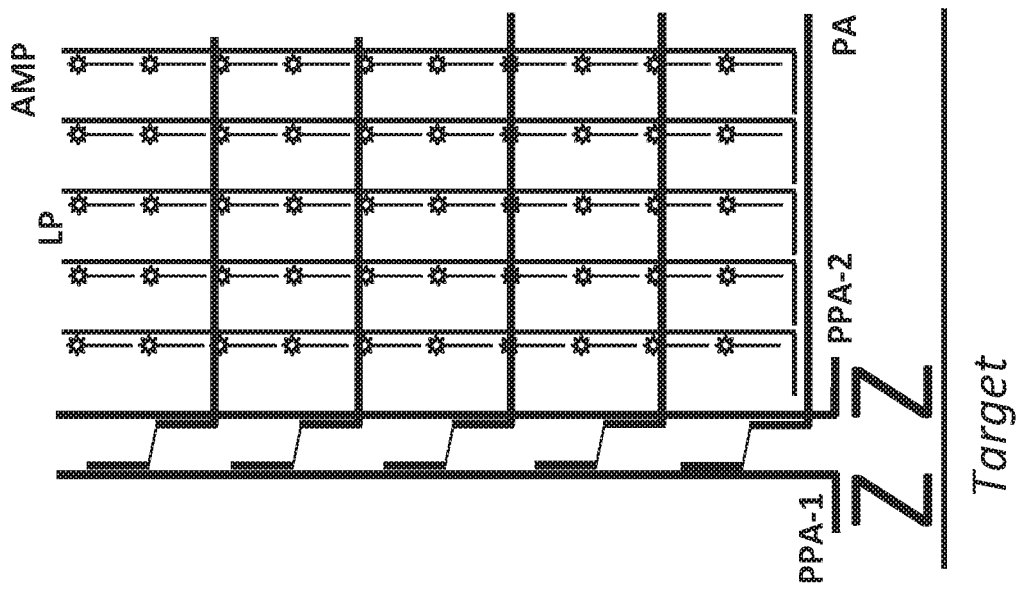
FIGS. 1A-1C show a schematic of previously described methods of detecting a nucleic acid target using a signal generating complex (SGC). PPA, pre-pre-amplifier; PA, pre-amplifier; AMP, amplifier; LP, label probe.

The present invention covers methods to enhance the signal amplification power of existing methods for the in situ detection of nucleic acid targets, including short targets such as splice junctions, point mutations, microRNA and fusion RNA transcripts. In these existing methods, a hybridization amplification system is used to facilitate the detection and visualization of the target nucleic acid. An example of a method previously described in US 2009/0081688 is shown in FIG. 1A, where the target nucleic acid is detected using one or more pairs of target probes (pictured in a "Z" configuration) that bind neighboring nucleic acid sequences in the target nucleic acid, which are bound by a long nucleic acid molecule called a Pre-Amplifier (PA) through hybridization. The PA contains multiple repeated sequence segments or domains, each of which binds another long nucleic acid molecule called an Amplifier (AMP). Each AMP also contains multiple repeated sequence segments or domains, each of which binds a label probe molecule (LP). This serial hybridization process builds a Signal Generating Complex (SGC), which includes the target nucleic acid sequence, target probe pair, all layers of amplification molecules, and label probe molecules, which are used to generate a detectable signal. The detectable signal from the SGC can be generated by a variety of labeling methods, such as fluorescent or chromogenic labels for direct visualization, direct addition of detectable metal isotopes, or an enzymatic or chemical reaction that generates a fluorescent, chromogenic, or other detectable signal, as is known in the art and described herein. Such in situ detection methods can be used on tissue specimens immobilized on a glass slide, on single cells in suspension such as peripheral blood mononucleated cells isolated from blood samples, in solution-based assays where the target nucleic acids are present in a homogenized state, or in samples where the target nucleic acids have been selectively captured onto a solid substrate.

In FIG. 1, the target probe is depicted in a "Z" configuration, as described, for example, in U.S. Pat. No. 7,709,198, U.S. publications 2008/0038725 and 2009/0081688, and WO 2007/001986 and WO 2007/002006. The Z configuration shown in FIG. 1 has the target binding site in the same orientation in both target probe pairs (i.e., the target binding site is 5' to the pre-amplifier or pre-pre-amplifier binding site, or the target binding site is 3' to the pre-amplifier or pre-pre-amplifier binding site). It is understood that such a configuration, as depicted in FIG. 1, is merely exemplary. It is understood that the target probe pair can independently be in either orientation, that is, one member of the pair of target probes can have the target binding site 5' or 3' to the pre-amplifier or pre-pre-amplifier binding site, and can be paired with a second probe having a binding site 5' or 3' to the pre-amplifier or pre-pre-amplifier, such that there are four possible combinations of orientations for the target probe pairs.

One significant challenge of existing methods of in situ hybridization (ISH) is that it is possible for signal to be generated in the absence of the target nucleic acid, due to non-specific binding or trapping of components of the SGC. A key requirement for the successful application of ISH methods is that real signal generated by specific recognition of the target sequence should be strong enough to be easily detected, while in the absence of the target nucleic acid, any false signal should be low enough so as to be either undetectable or easily distinguishable from the true, target-generated signal. Maximal differentiation of signal generated in the presence or absence of the target nucleic acid (also known as a high "Signal-to-Noise Ratio") is important for robust in situ detection with both high sensitivity and specificity.

For longer target nucleic acids, a high Signal-to-Noise Ratio can be achieved through the use of multiple target probe pairs that bind to the same target nucleic acid molecule. In this situation, an SGC generated by any single probe pair can be small enough so as to be insufficient to generate detectable signal, thereby requiring the generation of SGCs from multiple probe pairs in close proximity to allow signal detection. Requiring the redundant detection of the same target through hybridization of multiple target probe pairs to generate visible signal creates a high degree of detection specificity for these long targets. For the detection of shorter nucleic acid sequences, where only one pair of target probes is to be used by choice or because the target nucleic acid sequence is too short to bind multiple probe pairs, for example, due to the short length of the target nucleic acid, a single SGC must be large enough to generate detectable signal.

More robust signal can be generated by increasing the overall number of label probes able to hybridize within the SGC. One approach is to increase the length of any set of amplification molecules, thereby increasing the number of hybridization segments and therefore increasing the number of label probes that can be bound in the SGC. However, the use of larger amplification molecules can be problematic, as larger molecules may have difficulty diffusing into the cellular matrix of a cell being analyzed by ISH and gaining access to the hybridization sites on the target nucleic acid. In addition, larger molecules are also more prone to bind or stick non-specifically, generating background noise or false positive signal. Further, long molecules are much more expensive to produce. The use of shorter amplification molecules makes it possible to synthesize them as oligonucleotides, which can be manufactured economically and consistently.

Figure 1B:
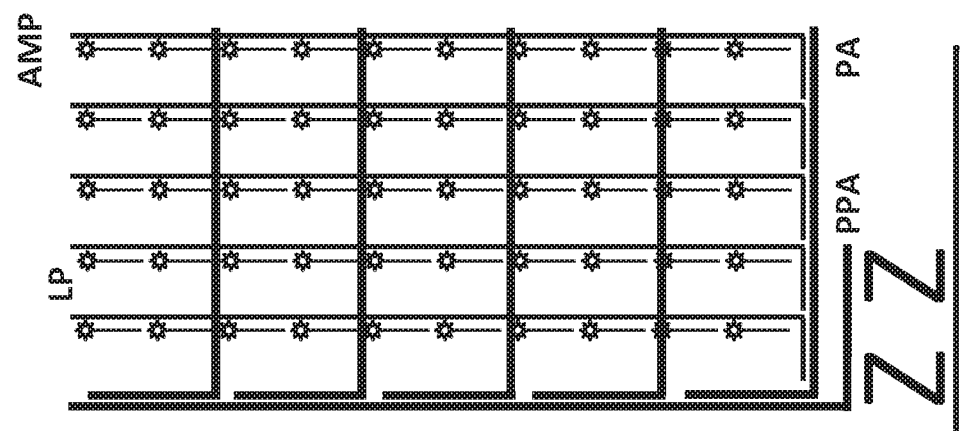

Another approach is to add additional layers of amplification molecules within the SGC, allowing a large SGC to be generated, even while the size of each component molecule is limited. As shown in FIG. 1B, an additional layer of amplification molecule called a Pre-Pre-Amplifier (PPA) can be added to generate the SGC. Using a PPA produces a larger SGC containing more label probes and allows for improved cell penetration while background noise caused by non-specific binding or trapping is kept to a low level. However, this approach of increasing the number of amplification layers has limits as to the number of layers that can be added. For example, if an amplifier molecule in the SGC closest to the target probe, such as the PPA in FIG. 1B, is bound or trapped non-specifically, a large SGC might be built on the molecule, generating a false positive signal.

Figure 1C:
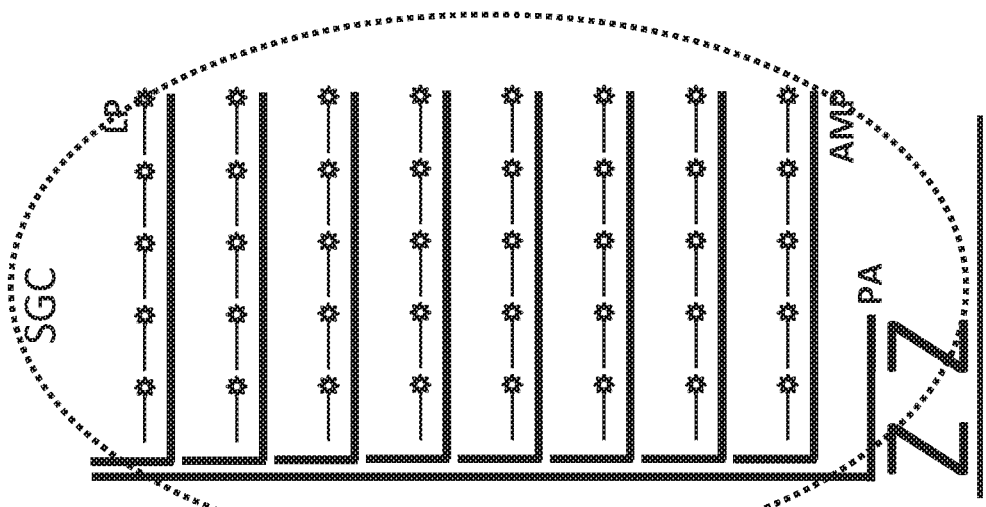

Another method has been described in US 2017/0101672, which improved upon the method as described in US 2009/0081688 by requiring collaborative hybridization of multiple distinct molecules in any layer of the SGC to allow the hybridization of the following layer. As illustrated in FIG. 1C, the PPA molecule, which is shown in FIG. 1B binding to two target probes, is provided as two molecules, PPA-1 and PPA-2, each of which binds to one of the two target probes. Each PA can only stably bind in the SGC when it hybridizes simultaneously with PPA-1 and PPA-2. In this approach, one amplification molecule alone, such as one PPA, which may be trapped or hybridized non-specifically, is not sufficient to permit growth of the SGC. However, when two or more components are present that are required for assembly of the amplification molecule layer, they allow a stable hybridization of the next layer or tier, in this case PA. This approach increases the number of amplification layers without negatively impacting signal-to-noise ratio. Perhaps surprisingly, even this strategy may have limits because having many collaborative hybridizations in multiple amplification layers can structurally weaken the SGC, can increase the total hybridization time, and therefore can reduce the robustness of the assay.

Building upon previously described methods, the present invention provides for further increases in the amplification power within the SGC, while also reducing the generation of artificial non-target specific signal. This is achieved by the hybridization of additional nucleic acids during the creation of the SGC, the division of single amplification molecules into an assemblage of multiple smaller pieces, and additional methods to increase the amount of label probe that is able to hybridize within a single SGC, allowing for more robust detection of the target nucleic acid sequence. At the same time, the use of multiple shorter amplification molecules allows more effective penetration of the sample and reduces non-specific trapping of amplification molecules within the sample that can generate signal in the absence of the target nucleic acid. Increasing signal detection while reducing non-specific signal provides for a more robust, specific detection of nucleic acid targets, especially those that are rare within a sample, short in sequence, highly homologous to other nucleic acid sequences, and/or partially degraded. Further, the present invention facilitates the simultaneous detection of multiple distinct nucleic acid targets of this nature within the same sample.

Previous methods for the in situ detection of nucleic acid targets have included the assembly of branched DNA to form a signal generating complex (SGC). As an example, in a three-layered hybridization amplification system, pre-pre-amplifier molecules hybridize to the target probes, followed by a layer of pre-amplifier molecules which hybridize to the pre-pre-amplifiers, followed by a layer of amplifier molecules that hybridize to the pre-amplifiers (see FIG. 1B). A label probe is a specialized molecule that is joined to a signal generating element such as fluorescent or chromogenic tag, metal isotope, or signal generating enzyme. Label probes hybridize to the amplifier molecules to form a complete SGC (FIG. 1A). The specificity of target detection is managed by requiring the coincident hybridization of multiple distinct elements at the same layer of amplification. For longer nucleic acid targets, signal specificity can be effectively controlled by requiring the simultaneous binding of multiple neighboring target probe pairs, where the SGC generated by the binding of a single target probe pair alone is not sufficient to generate a detectable signal, but the cumulative signal generated by the formation of SGCs from multiple neighboring target probe pairs is sufficient to allow signal detection. In cases where only a single target probe pair can be used, signal specificity can be gained by requiring simultaneous binding of multiple elements at a higher level of amplification. At an amplification level where such collaborative hybridization is used, the hybridization domain is divided between multiple amplification molecules (FIG. 1C). In contrast to when multiple probe pairs are used, signal detection using a single probe pair requires the generation of a larger SGC that is detectable as an individual entity.

The invention is based on building a complex between a target nucleic acid in order to label the target nucleic acid with a detectable label. Such a complex is sometimes referred to as a signal generating complex (SGC; see, for example, US 20170101672). Such a complex, or SGC, is achieved by building layers of molecules that allow the attachment of a large number of labels to a target nucleic acid.

The methods of the invention can employ a signal generating complex (SGC), where the SGC comprises multiple molecules rather than a single molecule. Such an SGC is particularly useful for amplifying the detectable signal, providing higher sensitivity detection of target nucleic acids. Such methods for amplifying a signal are described, for example, in U.S. Pat. Nos. 5,635,352, 5,124,246, 5,710,264, 5,849,481, and 7,709,198, and U.S. publications 2008/0038725 and 2009/0081688, as well as WO 2007/001986 and WO 2012/054795, each of which is incorporated herein by reference. The generation of an SGC is a principle of the RNAscope™ assay (see U.S. Pat. Nos. 7,709,198, 8,658,361 and 9,315,854, U.S. publications 2008/0038725, 2009/0081688 and 2016/0201117, as well as WO 2007/001986 and WO 2012/054795, each of which is incorporated herein by reference).

A basic Signal Generating Complex (SGC) is illustrated in FIG. 1A (see US 2009/0081688). A pair of target probes, depicted here as a pair of "Z's", hybridizes to a complementary molecule sequence, labeled "Target". Each target probe contains an additional sequence complementary to a pre-amplifier molecule (PA), which must hybridize simultaneously to both members of the target probe pair in order to bind stably. The pre-amplifier molecule is made up of two domains: one domain with a region that hybridizes to each target probe, and one domain that contains a series of nucleotide sequence repeats, each complementary to a sequence on the amplifier molecule (Amp). The presence of multiple repeats of this sequence allows multiple amplifier molecules to hybridize to one pre-amplifier, which increases the overall signal amplification. Each amplifier molecule is made up of two domains, one domain with a region that hybridizes to the pre-amplifier, and one domain that contains a series of nucleotide sequence repeats, each complementary to a sequence on the label probe (LP), allowing multiple label probes to hybridize to each amplifier molecule, further increasing the total signal amplification. Each label probe contains two components. One component is made up of a nucleotide sequence complementary to the repeat sequence on the amplifier molecule to allow the label probe to hybridize. This nucleotide sequence is linked to the second component, which can be any signal-generating entity, including a fluorescent or chromogenic label for direct visualization, a directly detectable metal isotope, or an enzyme or other chemical capable of facilitating a chemical reaction to generate a fluorescent, chromogenic, or other detectable signal. In FIG. 1A, the label probe is depicted as a line, representing the nucleic acid component, and a star, representing the signal-generating component. Together, the assembly from target probe to label probe is referred to as a Signal Generating Complex (SGC).

FIG. 1B illustrates a SGC enlarged by adding an amplification molecule layer, in this case a pre-pre-amplifier molecule (PPA, shown in red). The PPA binds to both target probes in one domain and multiple PAs in another domain.

FIG. 1C illustrates a different SGC structure that uses collaborative hybridization at the pre-amplifier level (see US 2017/0101672). Similarly to the SGC formed in FIGS. 1A and 1B, a pair of target probes hybridize to the target molecule sequence. Each target probe contains an additional sequence complementary to a unique pre-pre-amplifier molecule (PPA-1; PPA-2). The use of two independent molecules sets up a base on which collaborative hybridization can be required. Each pre-pre-amplifier molecule is made up of two domains: one domain with a region that hybridizes to one of the target probes, and one domain that contains a series of nucleotide sequence repeats, each containing both a sequence complementary to a sequence within the pre-amplifier molecule (PA), as well as a spacer sequence to facilitate PPA-PA binding efficiency. To stably attach to the growing SGC, each PA must hybridize to both PPA molecules simultaneously. Each pre-amplifier molecule is made up of two domains, one domain that contains sequences complementary to both pre-pre-amplifiers to allow hybridization, and one domain that contains a series of nucleotide sequence repeats each complementary to a sequence on the amplifier molecule (AMP). Multiple repeats of the amplifier hybridization sequence allows multiple amplifier molecules to hybridize to each pre-amplifier, further increasing signal amplification. For simplicity of illustration, amplifier molecules are shown hybridizing to one pre-amplifier molecule. Each amplifier molecule contains a series of nucleotide sequence repeats complementary to a sequence within the label probe (LP), allowing several label probes to hybridize to each amplifier molecule. Each label probe contains a signal-generating element to provide for signal detection.

As used herein, the term "label probe" refers to an entity that binds to a target molecule, directly or indirectly, generally indirectly, and allows the target to be detected. A label probe (or "LP") contains a nucleic acid binding portion that is typically a single stranded polynucleotide or oligonucleotide that comprises one or more labels which directly or indirectly provides a detectable signal. The label can be covalently attached to the polynucleotide, or the polynucleotide can be configured to bind to the label. For example, a biotinylated polynucleotide can bind a streptavidin-associated label. The label probe can, for example, hybridize directly to a target nucleic acid. In general, the label probe can hybridize to a nucleic acid that is in turn hybridized to the target nucleic acid or to one or more other nucleic acids that are hybridized to the target nucleic acid. Thus, the label probe can comprise a polynucleotide sequence that is complementary to a polynucleotide sequence, particularly a portion, of the target nucleic acid. Alternatively, the label probe can comprise at least one polynucleotide sequence that is complementary to a polynucleotide sequence in an amplifier, pre-amplifier, pre-pre-amplifier, signal generating complex (SGC), or the like, as described herein. In general in embodiments of the invention, the label probe binds to an amplifier. As used herein, a label probe comprising an enzyme label refers to a label probe comprising a nucleic acid binding portion such as an oligonucleotide and an enzyme that is coupled to the nucleic acid binding portion. As disclosed herein, the coupling of the enzyme to the nucleic acid binding portion can be covalent or through a high affinity binding interaction such as biotin/avidin or other similar high affinity binding molecules.

As used herein, a "target probe" is a polynucleotide that is capable of hybridizing to a target nucleic acid and capturing or binding a label probe or signal generating complex (SGC) component, for example, an amplifier, pre-amplifier or pre-pre-amplifier, to that target nucleic acid. The target probe can hybridize directly to the label probe, or it can hybridize to one or more nucleic acids that in turn hybridize to the label probe; for example, the target probe can hybridize to an amplifier, a pre-amplifier or a pre-pre-amplifier in an SGC. The target probe thus includes a first polynucleotide sequence that is complementary to a polynucleotide sequence of the target nucleic acid and a second polynucleotide sequence that is complementary to a polynucleotide sequence of the label probe, amplifier, pre-amplifier, pre-pre-amplifier, or the like. In general in embodiments of the invention, the target probe binds to a pre-amplifier, as in FIG. 1A, or to a pre-pre-amplifier, as in FIGS. 1B and 1C. The target probe is generally single stranded so that the complementary sequence is available to hybridize with a corresponding target nucleic acid, label probe, amplifier, pre-amplifier or pre-pre-amplifier.

As used herein, an "amplifier" is a molecule, typically a polynucleotide, that is capable of hybridizing to multiple label probes. Typically, the amplifier hybridizes to multiple identical label probes. The amplifier can also hybridize to a target nucleic acid, to at least one target probe of a pair of target probes, to both target probes of a pair of target probes, or to nucleic acid bound to a target probe such as a pre-amplifier or pre-pre-amplifier. For example, the amplifier can hybridize to at least one target probe and to a plurality of label probes, or to a pre-amplifier and a plurality of label probes. In general in embodiments of the invention, the amplifier can hybridize to a pre-amplifier. The amplifier can be, for example, a linear, forked, comb-like, or branched nucleic acid. As described herein for all polynucleotides, the amplifier can include modified nucleotides and/or nonstandard internucleotide linkages as well as standard deoxyribonucleotides, ribonucleotides, and/or phosphodiester bonds. Suitable amplifiers are described, for example, in U.S. Pat. Nos. 5,635,352, 5,124,246, 5,710,264, 5,849,481, and 7,709,198 and U.S. publications 2008/0038725 and 2009/0081688, each of which is incorporated by reference. In general in embodiments of the invention, the amplifier binds to a pre-amplifier and label probes (see FIG. 1).

As used herein, a "pre-amplifier" is a molecule, typically a polynucleotide, that serves as an intermediate binding component between one or more target probes and one or more amplifiers. Typically, the pre-amplifier hybridizes simultaneously to one or more target probes and to a plurality of amplifiers. Exemplary pre-amplifiers are described, for example, in U.S. Pat. Nos. 5,635,352, 5,681, 697 and 7,709,198 and U.S. publications 2008/0038725, 2009/0081688 and 2017/0101672, each of which is incorporated by reference. In general in embodiments of the invention, a pre-amplifier binds to both members of a target probe pair (see FIG. 1A), to a pre-pre-amplifier that can bind to a target probe pair (FIG. 1B), or to both members of a pair of pre-pre-amplifiers that can bind to a target probe pair (see FIG. 1C). A pre-amplifier also binds to an amplifier (see FIG. 1).

As used herein, a "pre-pre-amplifier" is a molecule, typically a polynucleotide, that serves as an intermediate binding component between one or more target probes and one or more pre-amplifiers. Typically, the pre-pre-amplifier hybridizes simultaneously to one or more target probes and to a plurality of pre-amplifiers. Exemplary pre-pre-amplifiers are described, for example, in U.S. publication 2017/0101672, which is incorporated by reference. In general in embodiments of the invention, a pre-pre-amplifier binds to a target probe pair (see FIG. 1B) or to a member of a target probe pair (see FIG. 1C) and to a pre-amplifier (see FIGS. 1B and 1C).

As described herein, whether using a configuration as depicted in FIG. 1A, 1B or 1C, the components of the SGC are designed such that the binding of both target probes is required in order to build an SGC. In the case of the configuration of FIGS. 1A and 1B, a pre-amplifier (FIG. 1A) (or pre-pre-amplifier as in FIG. 1B) must bind to both members of the target probe pair for stable binding to occur. This is achieved by designing binding sites between the target probes and the pre-amplifier (or pre-pre-amplifier) such that binding of both target probes to the pre-amplifier (or pre-pre-amplifier) has a higher melting temperature (Tm) than the binding of a single target probe to the pre-amplifier (or pre-pre-amplifier), and where the binding of a single target probe is unstable under the conditions of the assay. This design has been described previously, for example, in U.S. Pat. No. 7,709,198, U.S. publications 2008/0038725 and 2009/0081688, WO 2007/001986 WO 2007/002006, Wang et al., supra, 2012, Anderson et al., supra, 2016). By configuring the SGC components this way, the assembly of the SGC is achieved when both target probes are bound to the target nucleic acid and the pre-amplifier (or pre-pre-amplifier), thereby reducing background noise since assembly of an SGC as a false positive is minimized.

In the case of the configuration of FIG. 1C, the requirement that an SGC be formed only when both members of a target probe pair are bound to the target nucleic acid is achieved by requiring that a pre-amplifier be bound to both pre-pre-amplifiers, which in turn are bound to both members of the target probe pair, respectively. This requirement is achieved by designing the binding sites between the pre-pre-amplifiers and the pre-amplifier such that the melting temperature (Tm) between the binding of both pre-pre-amplifiers to the pre-amplifier is higher than the melting temperature of either pre-pre-amplifier alone, and where the binding of one of the pre-pre-amplifiers to the pre-amplifier is unstable under the conditions of the assay. This design has been described previously, for example, in US 20170101672, WO 2017/066211 and Baker et al., supra, 2017). Unless the pre-amplifier is bound to both pre-pre-amplifiers, the amplifiers and label probes cannot assemble into an SGC bound to the target nucleic acid, thereby reducing background noise since assembly of an SGC as a false positive is minimized.

The size, and thereby the effective amplification power, of the SGC can also be increased by increasing the length of amplification molecules. However, the longer the amplification molecule, the more susceptible it becomes to non-specific trapping as it permeates the sample. Trapped or non-specifically hybridized molecules can seed the generation of non-specific signal, as subsequent amplification molecules and label probes hybridize to form a functional SGC in the absence of the target nucleic acid sequence. As disclosed herein, to limit such background generation, multiple, shorter segments of amplification molecules can be hybridized to one another to form a lengthened sequence without the use of a longer molecule. This method can apply at any level of the amplification process.

Figure 2C:
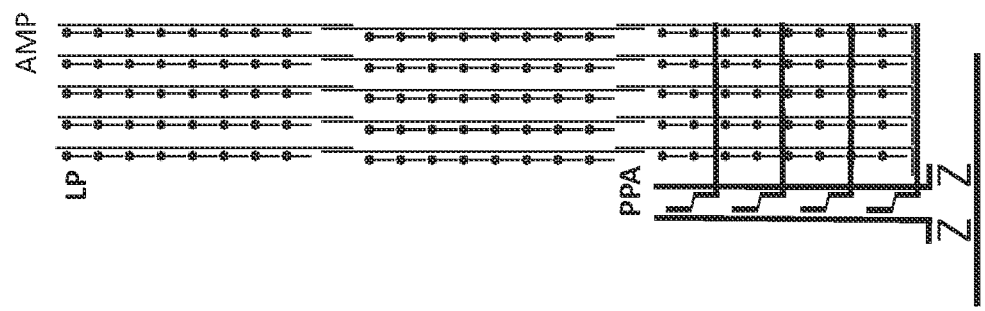
FIGS. 2A-2C show exemplary embodiments of detecting nucleic acids by extending the amplification components of an SGC.
Figure 2B:
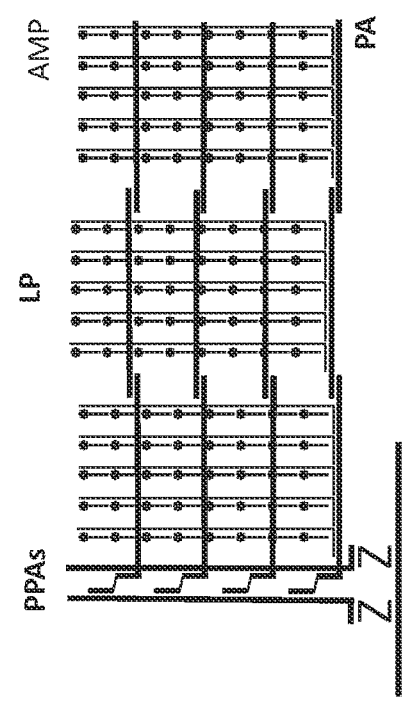
Figure 2A:
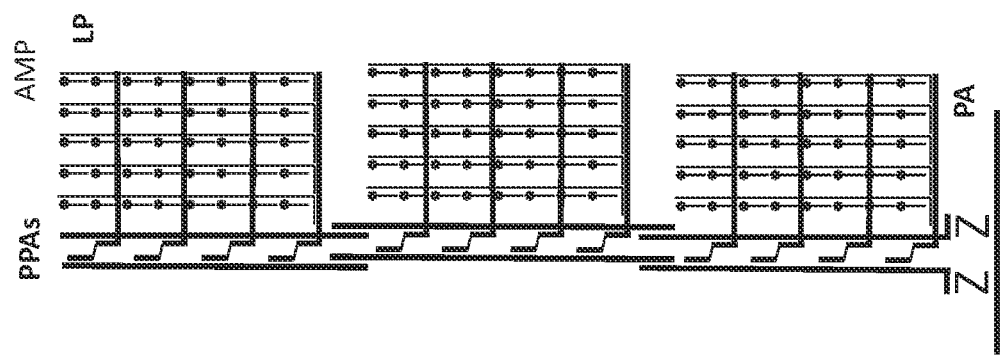

In one embodiment of a method of the invention using extension of amplification components, a three layered amplification system is used, with extension of the first amplification layer comprising pre-pre-amplifiers (PPAs) (FIG. 2A). A single target probe pair hybridizes to a target sequence, which can be a short target nucleic acid, followed by hybridization of a pre-pre-amplifier (PPA) molecule to each individual target probe pair. The pre-pre-amplifier that hybridizes to the target probe as depicted in FIG. 2A is referred to herein as a base PPA. At this stage, before the addition of pre-amplifier molecules, each pre-pre-amplifier sequence is extended by the hybridization of multiple lengthening molecules, referred to herein as extension PPA(s), which add additional hybridization domains as they extend the base pre-pre-amplifier, thereby lengthening the PPA layer. After completion of the pre-pre-amplifier layer, pre-amplifier molecules collaboratively hybridize to binding sequences on both base and extension pre-pre-amplifiers, which is then followed by the hybridization of amplifiers, label probes, and the generation of signal, as described above.

In a second embodiment of a method of the invention using extension of amplification components, a three layered amplification system is used, with extension of the second amplification layer comprising pre-amplifiers (PAs) (FIG. 2B). A single probe pair hybridizes to a short target sequence, followed by hybridization of a pre-pre-amplifier molecule to each individual probe pair. During the addition of the second amplification layer, pre-amplifier molecules collaboratively hybridize to the pre-pre-amplifiers. The pre-amplifier bound to the PPA as depicted in FIG. 2B is referred to herein as a base PA. The base PA is extended by the hybridization of multiple lengthening molecules, referred to herein as extension PA(s), which add additional hybridization domains to the base pre-amplifier, thereby increasing the length of the pre-amplifier layer. The completion of the lengthened pre-amplifier layer is followed by the hybridization of amplifiers, label probes, and the generation of signal, as described above.

In a third embodiment of a method of the invention using extension of amplification components, a three layered amplification system is used, with extension of the third amplification layer comprising amplifiers (AMPs) (FIG. 2C). In this embodiment, a single probe pair hybridizes to a target sequence, for example, a short target nucleic acid. This is followed by hybridization of a pre-pre-amplifier molecule to each individual probe pair, and then the collaborative hybridization of pre-amplifier molecules to the pre-pre-amplifiers. During the addition of the third amplification layer, amplifier molecules hybridize to the pre-amplifiers to form a base amplifier (base AMP). The base AMP is lengthened by the hybridization of multiple amplifier extension molecules, referred to herein as extension AMP(s), which add additional label probe hybridization domains as they lengthen the amplifier layer. The completion of the amplifier layer is followed by the hybridization of label probes, and the generation of signal, as described above.

As shown in FIG. 2 and as described above, signal detection can be improved by increasing the amplification power of the SGC. This can be achieved by increasing the number of hybridization domains on one or more layers of amplification molecules so that an overall greater number of label probes can hybridize within the SGC. However, increasing the overall length of amplification molecules increases the propensity for non-specific trapping of these molecules within the sample, which can yield false signal in the absence of the nucleic acid target. To increase the number of hybridization domains without using longer molecules that are prone to trapping, any amplification step can be extended by "tiling" multiple short molecules to generate a cumulatively higher number of hybridization domains, as described above.

In FIG. 2, a pair of target probes (Z) hybridize to the target sequence, followed by hybridization of one pre-preamplifier molecule (PPA) to each target probe. Pre-amplifier molecules (PA) collaboratively hybridize to both PPAs, with the total number of hybridizing PAs increased by PPA length extension (for example as in FIG. 2A). Amplifier molecules (AMP) hybridize to all bound PAs. In FIG. 2, AMPs are depicted hybridizing to one PA for simplicity of illustration, but it is understood that the AMPs can hybridize to all of the PA molecules in the SGC. Label probes (LP) bind to hybridization sequence repeats within each AMP, forming a complete SGC. In FIG. 2A, the amplification power of the SGC is increased by tiling multiple, shorter molecules to build a final, extended pre-pre-amplifier (base PPA plus extension PPA(s)) with more hybridization domains for pre-amplifier binding. In FIG. 2B, the amplification power of the SGC is increased by tiling multiple, shorter molecules to build a pre-amplifier with more amplifier hybridization domains (base PA plus extension PA(s)). In FIG. 2C, the amplification power of the SGC is increased by tiling multiple, shorter molecules to build an amplifier with more domains (base AMP plus extension AMP(s)) for label probe hybridization.

Figure 3A:
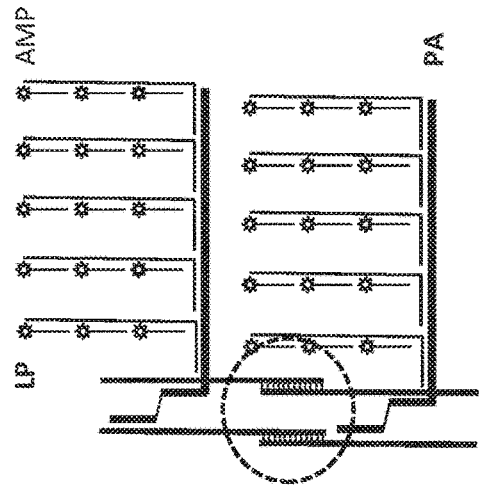
FIGS. 3A-3D show exemplary embodiments of connecting the extending components.

The extension of amplification molecules involves joining of multiple amplification molecule segments (base PPA/PA/AMP plus extension PPA(s)/PA(s)/AMP(s)) to build a longer sequence with more hybridization domains (also referred to herein as binding segment repeats (BSRs)), thereby allowing a greater number of molecules to hybridize in the next amplification layer or tier and building a larger SGC (FIG. 3A). A variety of methods can be used to attach a base amplification molecule to an extension amplification molecule(s). For example, the base and extension amplification molecules can be joined directly to one another, using complementary sequences on the end of each amplification molecule to allow direct hybridization to one another (see FIG. 3B). Alternatively, in another embodiment a smaller bridging molecule, referred to herein as a bridge or bridge molecule, can be used to hybridize to both base and extension amplification molecules, or to adjacent extension amplification molecules, acting as a molecular "tape" joining the two amplification molecules. This bridging molecule can hybridize directly to each amplification molecule (base and extension PPA(s)/PA(s)/AMP(s)) to join two segments (FIG. 3C). In another alternative embodiment, the bridging molecules can be designed to each hybridize to both amplification molecules, in particular PPAs, utilizing collaborative hybridization (FIG. 3D). Such a configuration can provide further structural stabilization to the SGC being assembled.

Exemplary embodiments of amplification molecule extension are depicted in FIG. 3. In FIG. 3A, a schematic of an SGC using amplification molecule extension is shown. A pair of target probes (Z) hybridize to the target sequence, and are each bound by pre-preamplifier molecules (PPA) (referred to herein as base PPAs). The total PPA sequence length is extended by the hybridization of one or more additional PPA molecules (extension PPAs) to each of the base PPAs hybridized to the target probe. The attachment of the two PPA extension molecules to the two base PPAs is highlighted by a dashed oval in FIG. 3. Pre-amplifier molecules (PA) hybridize to binding segment repeats (BSRs) on each base and extension PPA, increasing signal amplification within the SGC. Amplifier molecules (AMP) hybridize to binding sequence repeats (BSRs) on each PA. For simplicity of illustration, AMP molecules are shown hybridizing to only one PA per PPA extension layer, but it is understood that the AMPs can bind to any and all of the PAs. Label probes (LP) bind to complementary binding segment repeats within each AMP molecule, forming a complete SGC. To more closely view the exemplary embodiments of amplification molecule extension, FIGS. 3B-D show close-up views of part of the SGC illustrated in FIG. 3A and highlighted by a dashed-line box.

Figure 3B:
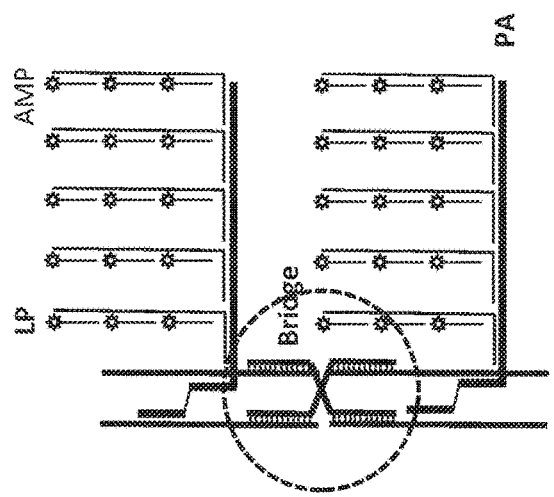
Figure 3C:
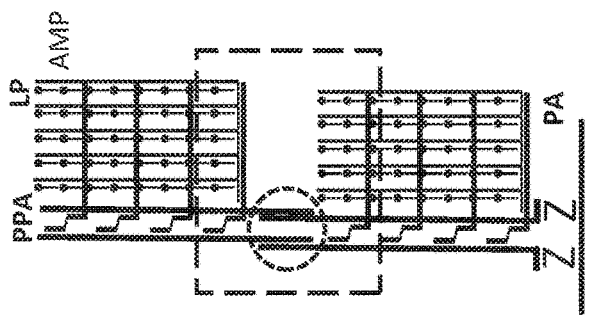
Figure 3D:
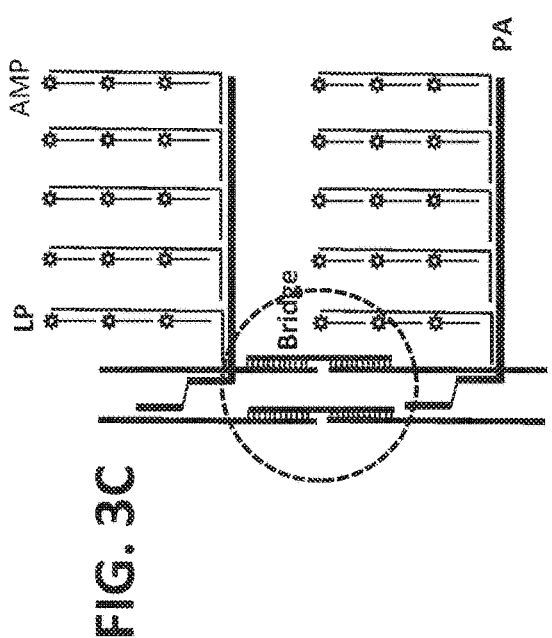

In one embodiment, illustrated in FIG. 3B, tiled amplification extension molecules hybridize directly via complementary nucleotide sequences on the end of each molecule (depicted as extended PPAs in FIG. 3B). In another embodiment, illustrated in FIG. 3C, tiled molecules can be joined using bridge molecules ("bridge") that anneal to both base and extension amplification molecules or to two adjacent extension amplification molecules. In a third embodiment, illustrated in FIG. 3D, tiled pairs of amplification molecules are joined and stabilized using bridges that anneal to both amplification molecules. Each embodiment can be applied both for amplification steps that involve the parallel use of distinct molecules (as depicted in FIG. 3), such as are used as the base for collaborative hybridization, and for extending amplification molecules that function singly (for example as depicted in FIGS. 1 and 1B).

Figure 7A:
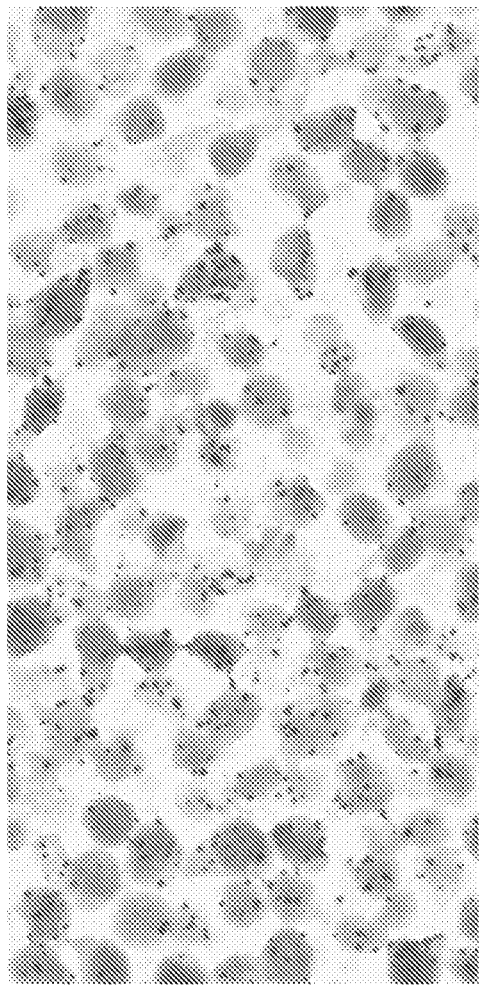
FIGS. 7A and 7B show detection of nucleic acids by in situ hybridization using amplification oligonucleotide extension.
Figure 7B:
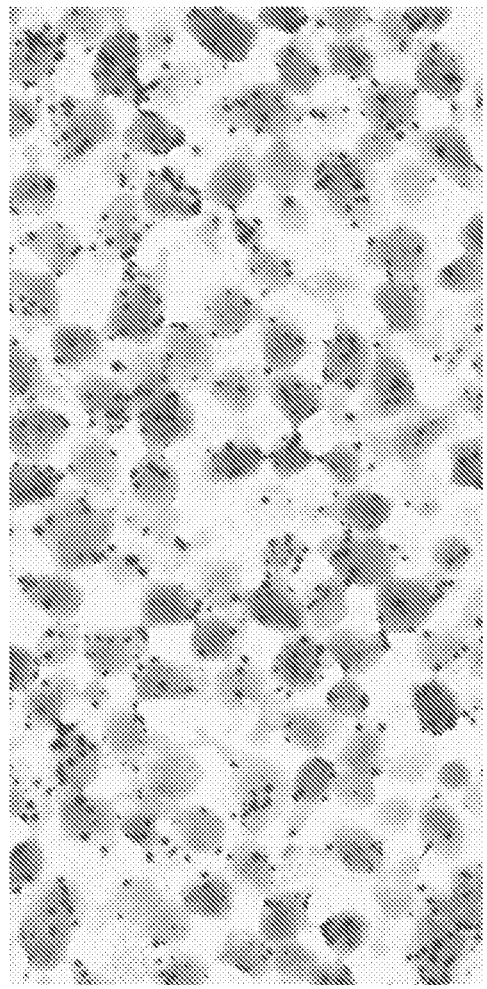

The use of amplification molecule extension is described in Example 1 and shown in FIG. 7. As described in Example 1, a single pair of target probes was used to detect a small region of the human POLR2A mRNA transcript in formalin-fixed, paraffin embedded cultured HeLa cells. Signal was amplified using a three-layered (three tiered) amplification system, with extension of the pre-preamplifier sequence by direct hybridization (as depicted in FIG. 3B). In the experiment shown in FIG. 7A, two pre-pre-amplifier molecules were joined by annealing directly to one another (base PPA plus extension PPA), increasing the number of binding segment repeats (BSRs) available for hybridization of pre-amplifier. In the experiment shown in FIG. 7B, three pre-pre-amplifier molecules were joined by annealing directly to one another (base PPA plus two extension PPAs), further increasing the number of binding segment repeats (BSRs) available for hybridization of pre-amplifiers, and therefore the amplification power and overall dot size generated by each SGC.

Figure 4:
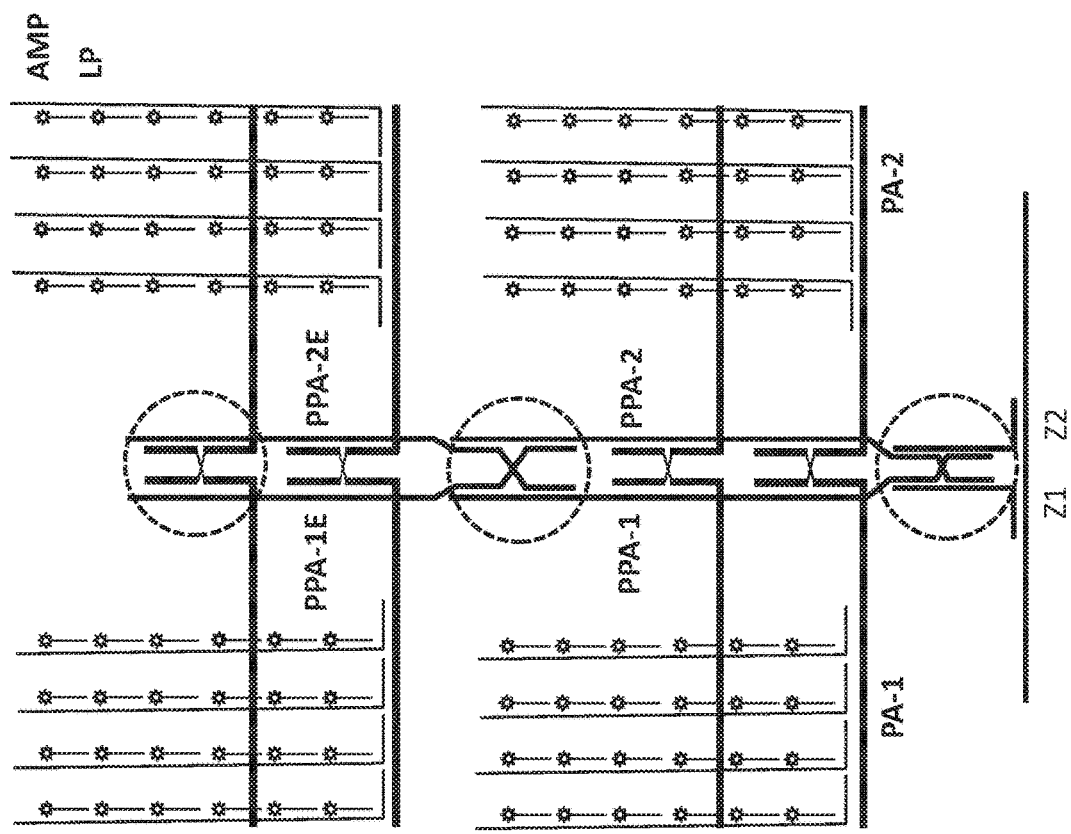
FIG. 4 shows exemplary embodiments of detecting nucleic acids using symmetric collaborative hybridization.

Increasing the degree of signal amplification allows for greater detection of SGC signal. However, it also carries an increased risk that non-specific signal may be generated by the trapping or non-specific hybridization of amplification molecules. The specificity of signal detection can be increased by using collaborative hybridization as previously described and illustrated in FIG. 1C. Amplification molecules that must collaboratively hybridize to multiple molecules in order to successfully attach to the growing SGC may experience a lower overall hybridization efficiency, as they can only stably bind when associated with the full hybridization sequence that is split among multiple molecules. Hybridization efficiency can be improved by introducing spacer sequences between the binding segment repeats on each base amplification molecule to allow for greater binding accessibility (see FIG. 1C, which depicts the spacer between the binding segment repeats for binding of multiple PAs). The additional nucleotide lengths between each binding segment repeat can be leveraged to add a second, distinct, collaboratively hybridizing amplification molecule in the opposite binding orientation, taking advantage of the previously unoccupied "spacer" sequence. Such a configuration is depicted in FIG. 4. By collaboratively hybridizing in a symmetric fashion, the two binding amplification molecules effectively tether two other amplification molecules in close proximity, providing stabilization and facilitating any further hybridization. Symmetric collaborative hybridization can be used at any step of the amplification process or tier of the amplification molecules, including hybridization of amplification molecules to target probes, extension of an amplification molecule, and/or addition of a new layer or tier of amplification molecule (FIG. 4).

As described previously, one method that can be used for increasing signal specificity is requiring collaborative hybridization of multiple distinct molecules within the same amplification layer in order to successfully generate a final detectable signal (US 2017/0101672). When multiple, distinct molecules are used, both molecules can be made necessary to the further SGC assembly by dividing the hybridization sequence (binding segment repeat) for the next tier of hybridization molecules between the distinct molecules. Because successful attachment of the next tier of amplification molecules requires hybridization to multiple distinct molecules, the amplification molecules that collaboratively hybridize may experience a lower overall hybridization efficiency, as they can only stably bind when associated with the full hybridization sequence that is split among multiple base molecules. The efficiency of hybridization can be improved by introducing spacer sequences between each partial hybridization sequence repeat to allow greater binding accessibility, as described above. This use of spacer sequences allows the addition of a second, distinct, collaboratively hybridizing amplification molecule in the opposite orientation, taking advantage of the previously unbound "spacer" region. In this way, two distinct amplification molecules can collaboratively hybridize in a symmetric fashion, providing stabilization and improving the efficiency of hybridization to additional binding segment repeats on the amplification molecule by effectively tethering the amplification molecules in close proximity (see FIG. 4).

FIG. 4 shows three possible uses of symmetric collaborative hybridization. As depicted in more detail in FIG. 4, two target probes ("Z1" and "Z2") hybridize to a target sequence. Two pre-preamplifier molecules (PPA-1 and PPA-2) each hybridize to both target probes using symmetric collaborative hybridization (depicted in lower broken circle in FIG. 4). Each pre-pre-amplifier molecule is extended by the attachment of additional pre-pre-amplifier molecule(s) (extension PPA(s)) that contain the same pre-amplifier binding segment repeats (PPA-1E and PPA-2E) (depicted in middle broken circle in FIG. 4). These extension amplification molecules each hybridize to both PPA-1 and PPA-2, using symmetric collaborative hybridization. As illustrated in FIG. 4, symmetric collaborative hybridization can be used at any level of SGC formation, including attachment of amplification molecules to the target probes (FIG. 4, lower broken circle), extension of parallel amplification molecules (FIG. 4, middle broken circled), and/or in the attachment of additional amplification molecule tiers or layers (FIG. 4, upper broken circle).

Figure 5:
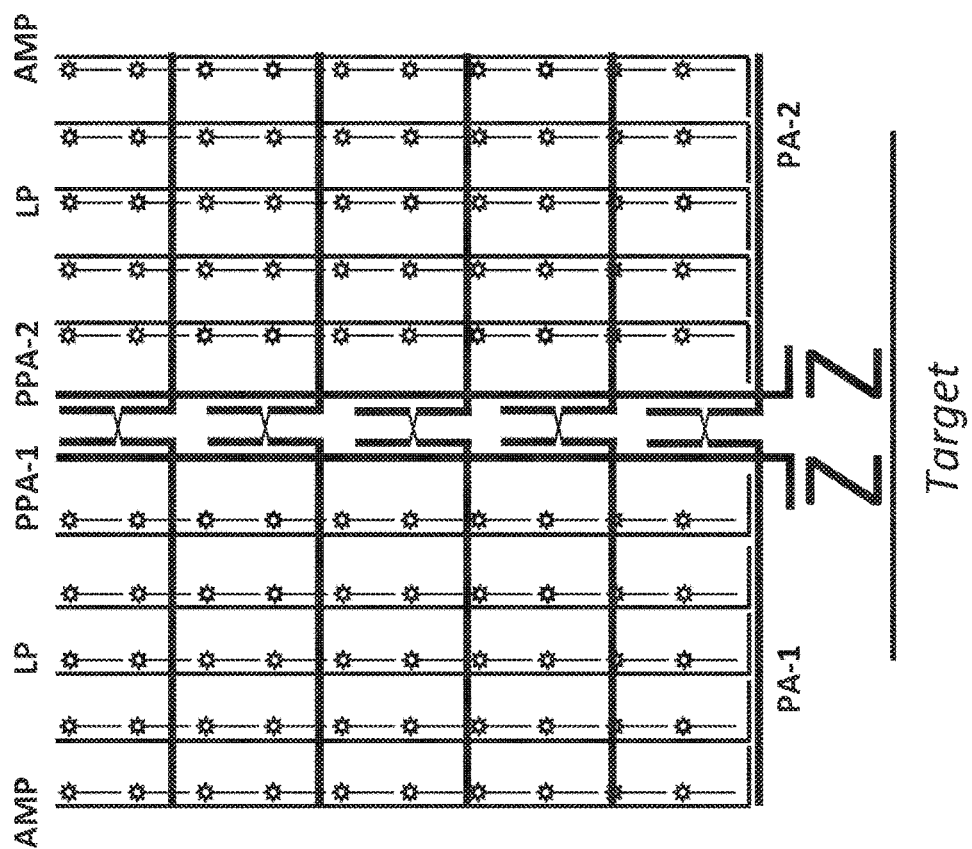
FIG. 5 shows an exemplary embodiment of detecting nucleic acids by increasing the density of the SGC utilizing symmetric collaborative hybridization.

In one embodiment, symmetric collaborative hybridization can be used to increase the density and amplification power of the SGC (FIG. 5). The use of collaborative hybridization increases the specificity of signal amplification by allowing amplification molecules to only stably attach to the growing SGC by simultaneously hybridizing to lower tier amplification molecules. However, the requirement for simultaneous hybridization to two amplification molecules may also lower the hybridization efficiency. Including spacer sequences between each partial hybridization sequence can improve hybridization efficiency by allowing greater accessibility to the lower tier amplification molecules, as described above. Using symmetric collaborative hybridization, an additional amplification molecule can be hybridized within the "spacer" nucleotide sequence, doubling the amplification power for the same length of amplification molecule for each repeat (see FIG. 5). This embodiment allows the amplification power of the SGC to be increased while simultaneously providing further stabilization, and improved hybridization efficiency, by tethering the amplification molecules in close proximity.

FIG. 5 shows a configuration for increasing the density of the SGC. The formation of an SGC with maximal amplification power is dependent on the efficient hybridization and assembly of amplification molecules, such that all binding segment repeats within the SGC can be fully occupied. Hybridization of the greatest possible number of amplification molecules within a single SGC allows the addition of the most possible amount of label probes, to generate the most robust signal detection. Introducing spacer sequences between binding segment repeats can facilitate amplifier binding to allow for greater hybridization domain occupancy, as described above. However, this introduces a significant length of unoccupied, "wasted" sequences. To increase the overall density of the SGC when using spacer sequences, the amount of amplification within a single SGC can be doubled by using two different amplification molecules that collaboratively hybridize in a symmetric fashion. In addition to increasing the theoretical amplification power of an SGC, symmetric collaborative hybridization may also help to build a complete SGC with greater efficiency, by bringing the amplification molecules closer together during hybridization of each amplification molecule in the new layer, stabilizing the growing SGC and facilitating further collaborative hybridization events in the new amplification layer or tier.

As shown in FIG. 5, two target probes ("Z") hybridize to the target sequence. These target probes have distinct nucleotide sequences in both target hybridization and PPA hybridization regions. The distinct PPA-hybridization sequence allows two independent PPA molecules of distinct sequence, PPA-1 and PPA-2, to each hybridize uniquely to one corresponding target probe. Each PPA contains hybridization sequences (binding segment repeats) for attachment of the pre-amplifier layer. Two pre-amplifiers, PA-1 and PA-2, are each made up of two domains: one domain containing both PPA-1 and PPA-2 hybridization sequences, and one domain containing multiple binding segment repeats for the hybridization of amplifier molecules (AMP). The PPA-1 and PPA-2 hybridization sequences within PA-1 and PA-2 are distinct, and oriented such that each PA-1 hybridizes to PPA-1 proximal to the target probe binding site, and PPA-2 hybridizes adjacent to PPA-1 and distal to its target binding site. PA-2 hybridizes to PPA-2 proximal to the target probe binding site, and PPA-1 hybridizes adjacent to PPA-2 and distal to its target binding site. This symmetric collaborative hybridization "cross-over" allows the same nucleotide length, including both binding and spacer sequences, to be collaboratively hybridized by two preamplifier molecules rather than one. As a result, twice as many amplifier molecules (AMP), and thereby twice as many label probes (LP, depicted as a line with a star), can hybridize within the SGC, increasing density and overall amplification power of the SGC. For simplicity of this illustration, amplifier molecules (AMP) are depicted hybridizing to only one PA-1 and one PA-2, however it is understood that amplifier molecules can hybridize to any and all PA-1 and PA-2 within the SGC.

The use of symmetric collaborative hybridization is demonstrated in FIG. 8. In the experiment shown in FIG. 8, a single pair of target probes detected a small region of the human POLR2A mRNA transcript in formalin-fixed, paraffin embedded cultured HeLa cells, and signal was amplified using a three-layered amplification system. In this example, symmetric collaborative hybridization was employed at the second layer of amplification, using two distinct pre-preamplifier molecules to create two symmetric collaborative hybridization sites, allowing for two distinct pre-amplifiers to bind in a balanced orientation, as depicted in FIG. 5.

The methods described herein can be used for the detection of multiple target nucleic acid sequences in a multiplex analysis. The multiple targets can be either within the same nucleic acid molecule or on distinct nucleic acid molecules, such as distinct mRNA transcripts. One embodiment of the combined use of these methods for the purpose of multiple target detection is illustrated in FIG. 6. In this embodiment, three short nucleic acid target sequences are examined simultaneously, with a single distinct target probe pair to detect each target. Each target probe pair hybridizes to a unique set of pre-pre-amplifier molecules, each containing distinct hybridization domain sequences (binding segment repeats) for distinct pre-amplifier molecules. Pre-amplifiers collaboratively hybridize to two pre-pre-amplifier molecules. Such a configuration can be used to increase the specificity of signal generated using a single probe pair when detecting short target nucleic acids. Unique amplifiers hybridize to pre-amplifier molecules for each different target nucleic acid, followed by hybridization of unique label probes for each SGC. Label probes within SGCs for each target contain different detectable elements, to ensure that all three target nucleic acid sequences can be detected and distinguished.

The methods described herein can be applied to the simultaneous detection of multiple, distinct target nucleic acid sequences within the same sample. As an example, FIG. 6 illustrates the detection of three distinct nucleic acid targets in the same sample, each using an amplification method that involves the use of two paired, parallel pre-preamplifiers that are each tiled by direct annealing to extend the number of pre-amplifier symmetric collaborative hybridization domains. Two distinct pre-amplifiers hybridize symmetrically to each pre-pre-amplifier molecule, increasing the number of amplifiers and subsequently the number of label probes that hybridize within each final SGC. For each distinct nucleic acid target, target probes, amplification molecules and label probes with unique nucleic acid sequences are used to prevent cross detection, and label probes used within the SGC of each target generate distinct detectable signals, allowing the multiple target nucleic acids to be distinguished.

In FIG. 6, three independent nucleic acid targets are individually detected with three specific target probe pairs ("ZZ", Target 1; Target 2; Target 3). Two distinct PPAs hybridize to each target probe pair, with each PPA hybridizing to one of the two target probes (for Target 1: PPA-1 and PPA-A; for Target 2: PPA-2 and PPA-B; for Target 3: PPA-3 and PPA-C). Each PPA pair contains different PA binding sequences, as well as an extension hybridization sequence to allow the attachment of a second PPA layer containing additional PA binding sequence repeats. On each growing SGC, two distinct PAs collaboratively hybridize to each PPA pair (PA-1 and PA-A, each collaboratively hybridize to both PPA-1 and PPA-A; PA-2 and PA-B, each collaboratively hybridize to both PPA-2 and PPA-B; PA-3 and PA-C, each collaboratively hybridize to both PPA-3 and PPA-C), allowing both increased signal specificity and amplification for each target. Both PAs for a given "tree" (i.e., SGC) contain distinct PPA-hybridization sequences but the same AMP-hybridization sequence repeats (binding segment repeats), allowing a single design of AMP molecule to hybridize to both PAs (AMP-1 hybridizes to both PA-1 and PA-A; AMP-2 hybridizes to both PA-2 and PA-B; AMP-3 hybridizes to both PA-3 and PA-C). Distinct label probes, which include a nucleic acid sequence for hybridization to a specific AMP, are hybridized to the growing SGC (LP-1 hybridizes to AMP-1; LP-2 hybridizes to AMP-2; LP-3 hybridizes to AMP-3). In addition to the nucleic acid hybridization domain, each of the label probes contain a unique signal generating element, allowing independent SGCs generated from each target to be distinguished.

Figure 9A:
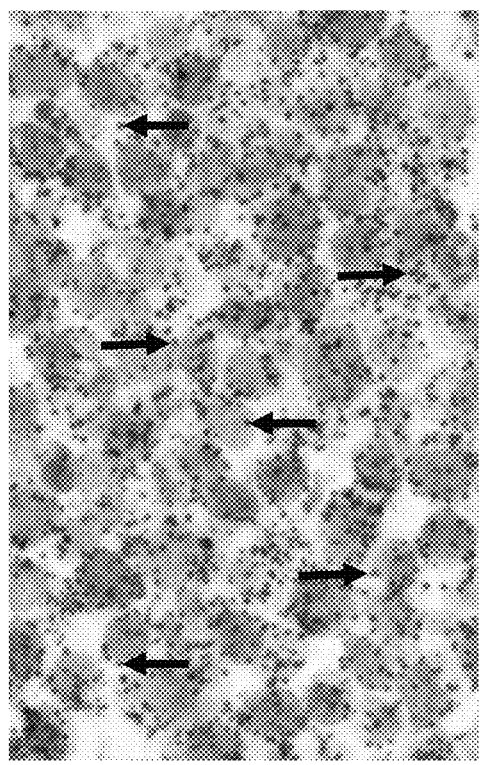
FIGS. 9A and 9B show detection of nucleic acids by in situ hybridization for detection of multiple targets within the same tissue sample.
Figure 9B:
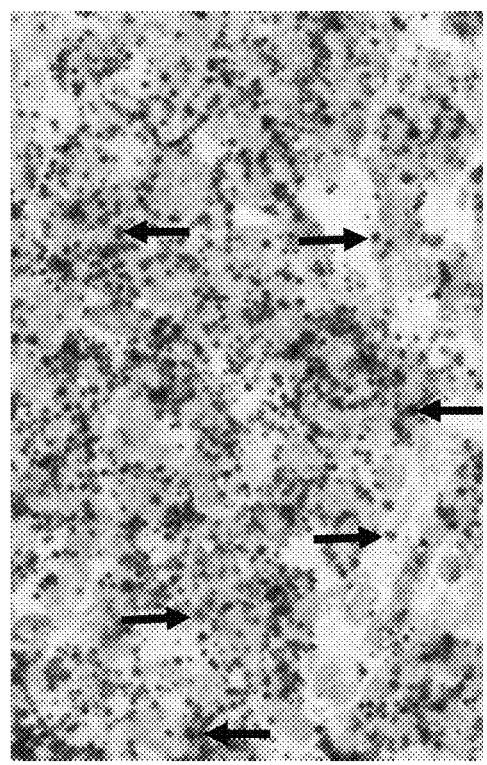

The combined use of the outlined methods for the detection of multiple targets is demonstrated in FIG. 9. In the experiment shown in FIG. 9A, one pair of target probes detected the first target, a small region of the human POLR2A mRNA transcript (stained red), while another probe pair detected the second target, a small region of the human PPIB mRNA transcript (stained green) in formalin-fixed, paraffin embedded cultured HeLa cells. Signal representing each target was amplified using a multi-layered amplification system with direct hybridization allowing for amplifier molecule extension (see FIG. 6). In FIG. 9B, the same signal amplification method was used to detect human POLR2A mRNA transcript (stained red) and human PPIB mRNA transcript (stained green) in a formalin-fixed, paraffin embedded human colon cancer tumor.

In one embodiment, the invention comprises a composition comprising a Signal Generating Complex (SGC) comprising any combination of target probes, pre-pre-amplifiers, pre-amplifiers, amplifiers and/or label probes and configurations thereof depicted in any one or more of FIGS. 2-6 and/or, as compatible with the detection of a target nucleic acid.

In one embodiment, the invention provides a composition comprising a Signal Generating Complex (SGC), wherein the composition comprises: (A) a pair of target probes (TPs), wherein a first TP of the pair of TPs comprises a nucleic acid sequence comprising two segments, (i) a segment comprising a binding site for a first segment of a target nucleic acid, and (ii) a segment comprising a binding site for a first base pre-pre-amplifier (base PPA); and wherein a second TP of the pair of TPs comprises a nucleic acid sequence comprising two segments, (i) a segment comprising a binding site for a second segment of the target nucleic acid, and (ii) a segment comprising a binding site for a second base PPA; (B) a pair of base PPAs comprising the first and second base PPAs, wherein the first base PPA comprises a nucleic acid sequence comprising three segments, (i) a segment that binds to the first base PPA binding site of the first TP, (ii) a segment comprising a plurality of first pre-amplifier binding segment repeats (first PA-BSRs), and (iii) a segment comprising a binding site for a first extension pre-pre-amplifier (extension PPA); and wherein the second base PPA comprises a nucleic acid sequence comprising three segments, (i) a segment that binds to the second base PPA binding site of the second TP, (ii) a segment comprising a plurality of second pre-amplifier binding segment repeats (second PA-BSRs), and (iii) a segment comprising a binding site for a second extension PPA; wherein the first and second PA-BSRs are different sequences, and wherein the segments are in the order (i), (ii), (iii); (C) a set of extension PPAs comprising the first and second extension PPAs, wherein the first extension PPA comprises a nucleic acid sequence comprising two segments, (i) a segment that binds to the first extension PPA binding site of the first base PPA, and (ii) a segment comprising a plurality of the first PA-BSRs; and wherein the second extension PPA comprises a nucleic acid sequence comprising two segments, (i) a segment that binds to the second extension PPA binding site of the second base PPA, and (ii) a segment comprising a plurality of the second PA-BSRs; (D) a plurality of pre-amplifiers (PAs), wherein the PAs comprise a nucleic acid sequence comprising three segments, (i) a segment complementary to the first PA-BSR, (ii) a segment complementary to the second PA-BSR, and (iii) a segment comprising a plurality of amplifier binding segment repeats (AMP-BSRs); wherein the segments are in the order (i), (ii), (iii); (E) a plurality of amplifiers (AMPs), wherein the AMPS comprise a nucleic acid sequence comprising two segments, (i) a segment complementary to the AMP-BSRs, and (ii) a segment comprising a plurality of label probe binding segment repeats (LP-BSRs); and (F) a plurality of label probes (LPs), wherein the LPs comprise a nucleic acid sequence comprising two segments, (i) a segment complementary to the LP-BSRs, and (ii) a segment that is detectable; wherein the respective binding sites and complementary segments are hybridized to form the SGC (see FIG. 2A).

In one embodiment, the set of extension PPAs comprises at least one additional first extension PPA and at least one additional second extension PPA, wherein the additional first extension PPA comprises a nucleic acid sequence comprising two segments, (i) a segment comprising a binding site for the first extension PPA, and (ii) a segment comprising a plurality of the first PA-BSRs; wherein the additional second extension PPA comprises a nucleic acid sequence comprising two segments, (i) a segment comprising a binding site for the second extension PPA, and (ii) a segment comprising a plurality of the second PA-BSRs; and wherein the at least one additional first PPA optionally comprises a third segment (iii) comprising a second binding site for the first extension PPAs, and the at least one additional second PPA optionally comprises a third segment (iii) comprising a second binding site for the second extension PPAs, wherein the segments are in the order (i), (ii), (iii).

In another embodiment, the binding sites between the first base PPA and the first extension PPA and/or between the extension PPAs comprise complementary sequences, and wherein the binding sites between the second base PPA and the second extension PPA and/or between the second extension PPAs comprise complementary sequences (see FIG. 2A and FIG. 3B).

In another embodiment, the composition further comprises a pair of bridges comprising a first bridge and second bridge, wherein the first bridge comprises two sections that bind to the first extension PPA binding site of the first base PPA and/or the first extension PPA binding site of the first extension PPA; and wherein the second bridge comprises two sections that bind to the second extension PPA binding site of the second base PPA and/or the second extension PPA binding site of the second extension PPA; wherein binding of the bridge tethers the extension PPA to the base PPA and/or the extension PPAs to each other (see FIGS. 2A and 3C).

In another embodiment, the composition further comprises a pair of bridges comprising a first bridge and second bridge, wherein the first bridge comprises two sections, (i) a section that binds to the first extension PPA binding site of the first base PPA and/or the first extension PPA binding site of the first extension PPA, and (ii) a section that binds to the second extension PPA binding site of the second extension PPA; wherein the second bridge comprises two sections, (i) a section that binds to the second extension PPA binding site of the second base PPA and/or the second extension PPA binding site of the second extension PPA, and (ii) a section that binds to the first extension PPA binding site of the first extension PPA; wherein binding of the bridge tethers the second extension PPA to the first base PPA or the second extension PPA to the first extension PPA, and tethers the first extension PPA to the second base PPA or the first extension PPA to the second extension PPA (see FIG. 2A and FIG. 3D).

In another embodiment, the first base PPA and/or the first extension PPA comprises a fourth segment (iv) comprising a binding site for the second extension PPA, and wherein the second base PPA and/or the second extension PPA comprises a fourth segment (iv) comprising a binding site for the first extension PPA, wherein the segments of the PPA are in the order (i), (ii), (iv), (iii) (see FIG. 2A and FIG. 4, middle circle).

In another embodiment, the invention provides a composition comprising a Signal Generating Complex (SGC), wherein the composition comprises: (A) a pair of target probes (TPs), wherein a first TP of the pair of TPs comprises a nucleic acid sequence comprising two segments, (i) a segment comprising a binding site for a first segment of a target nucleic acid, and (ii) a segment comprising a binding site for a first pre-pre-amplifier (PPA); and wherein a second TP of the pair of TPs comprises a nucleic acid sequence comprising two segments, (i) a segment comprising a binding site for a second segment of the target nucleic acid, and (ii) a segment comprising a binding site for a second PPA; (B) a pair of PPAs comprising the first and second PPAs, wherein the first PPA comprises a nucleic acid sequence comprising two segments, (i) a segment that binds to the first PPA binding site of the first TP, and (ii) a segment comprising a plurality of first pre-amplifier binding segment repeats (first PA-BSRs); and wherein the second PPA comprises a nucleic acid sequence comprising two segments, (i) a segment that binds to the second PPA binding site of the second TP, and (ii) a segment comprising a plurality of second PA-BSRs, wherein the first and second PA-BSRs are different sequences; (C) a plurality of base pre-amplifiers (base PAs), wherein the base PAs comprise a nucleic acid sequence comprising four segments (i) a segment complementary to the first PA-BSRs, (ii) a segment complementary to the second PA-BSRs, (iii) a segment comprising a plurality of amplifier binding segment repeats (AMP-BSRs), and (iv) a segment that binds to an extension pre-amplifier (extension PA), wherein the segments are in the order (i), (ii), (iii), (iv); (D) a plurality of extension PAs, wherein the extension PAs comprise a nucleic acid sequence comprising two segments (i) a segment that binds to the extension PA binding site of the base PAs and (ii) a plurality of amplifier binding segment repeats (AMP-BSRs); and wherein the extension PAs optionally comprise a third segment (iii) comprising a binding site for the extension PAs, wherein the segments are in the order (i), (ii), (iii); (E) a plurality of amplifiers (AMPs), wherein the AMPS comprise a nucleic acid sequence comprising two segments, (i) a segment complementary to the AMP-BSRs, and (ii) a segment comprising a plurality of label probe binding segment repeats (LP-BSRs); and (F) a plurality of label probes (LPs), wherein the LPs comprise a nucleic acid sequence comprising two segments, (i) a segment complementary to the LP-BSRs, and (ii) a segment that is detectable; wherein the respective binding sites and complementary segments are hybridized to form the SGC (see FIG. 2B).

In one embodiment, the binding sites between the base PAs and the extension PAs comprise complementary sequences (FIG. 2B and FIG. 3B). In another embodiment, the composition further comprises a bridge, wherein the bridge comprises two sections that bind to the extension PA binding site of the base PA and/or the extension PA binding site of the extension PA, wherein binding of the bridge tethers the extension PA to the base PA and/or the extension PAs to each other (see FIG. 2B and FIG. 3C).

In another embodiment the invention provides a composition comprising a Signal Generating Complex (SGC), wherein the composition comprises: (A) a pair of target probes (TPs), wherein a first TP of the pair of TPs comprises a nucleic acid sequence comprising two segments, (i) a segment comprising a binding site for a first segment of a target nucleic acid, and (ii) a segment comprising a binding site for a first pre-pre-amplifier (PPA); and wherein a second TP of the pair of TPs comprises a nucleic acid sequence comprising two segments, (i) a segment comprising a binding site for a second segment of the target nucleic acid, and (ii) a segment comprising a binding site for a second PPA; (B) a pair of PPAs comprising the first and second PPAs, wherein the first PPA comprises a nucleic acid sequence comprising two segments, (i) a segment that binds to the first PPA binding site of the first TP, and (ii) a segment comprising a plurality of first pre-amplifier binding segment repeats (first PA-BSRs); and wherein the second PPA comprises a nucleic acid sequence comprising two segments, (i) a segment that binds to the second PPA binding site of the second TP, and (ii) a segment comprising a plurality of second PA-BSRs, wherein the first and second PA-BSRs are different sequences; (C) a plurality of pre-amplifiers (PAs), wherein the PAs comprise a nucleic acid sequence comprising three segments, (i) a segment complementary to the first PA-BSR, (ii) a segment complementary to the second PA-BSR, and (iii) a segment comprising a plurality of amplifier binding segment repeats (AMP-BSRs); wherein the segments are in the order (i), (ii), (iii); (D) a plurality of base amplifiers (base AMPs), wherein the base AMPs comprise a nucleic acid sequence comprising three segments (i) a segment complementary to the AMP-BSRs, (ii) a segment comprising a plurality of label probe binding segment repeats (LP-BSRs), and (iii) a segment that binds to an extension amplifier (extension AMP), in the order (i), (ii), (iii); (E) a plurality of extension AMPs, wherein the extension AMPs comprise a nucleic acid sequence comprising two segments (i) a segment that binds to the extension AMP binding site of the base AMP, and (ii) a segment comprising a plurality of label probe binding segment repeats (LP-BSRs); and wherein the extension AMPs optionally comprise a third segment (iii) comprising a binding site for the extension PAs, wherein the segments are in the order (i), (ii), (iii); (F) a plurality of label probes (LPs), wherein the LPs comprise a nucleic acid sequence comprising two segments (i) a segment complementary to the LP-BSRs, and (ii) a segment that is detectable; wherein the respective binding sites and complementary segments are hybridized to form the SGC (see FIG. 2C).

In another embodiment, the binding sites between the base AMPs and the extension AMPs comprise complementary sequences (see FIG. 2C and FIG. 3B). In another embodiment, the composition further comprises a bridge, wherein the bridge comprises two sections that bind to the extension AMP binding site of the base AMP and/or the extension AMP binding site of the extension AMP, wherein binding of the bridge tethers the extension AMP to the base AMP and/or the extension AMPs to each other (see FIG. 2C and FIG. 3C).

In one embodiment of the compositions described above, (I) the first TP further comprises a third segment (iii) comprising a binding site for the second PPA; wherein the second TP further comprise a third segment (iii) comprising a binding site for the first PPA; and wherein the segments are in the order (i), (iii), (ii); and (II) the first base PPA further comprises a fourth segment (iv) comprising a binding site for the second TP; wherein the second base PPA further comprises a fourth segment (iv) comprising a binding site for the first TP; wherein the segments are in the order (iv), (i), (ii), (iii); or the first PPA further comprises a third segment (iii) comprising a binding site for the second TP; wherein the second PPA further comprises a third segment (iii) comprising a binding site for the first TP; wherein the segments are in the order (iii), (i), (ii) (FIG. 4A, lower circle).

In another embodiment, the invention provides a composition comprising a Signal Generating Complex (SGC), wherein the composition comprises: (A) a pair of target probes (TPs), wherein a first TP of the pair of TPs comprises a nucleic acid sequence comprising two segments, (i) a segment comprising a binding site for a first segment of a target nucleic acid, and (ii) a segment comprising a binding site for a first base pre-pre-amplifier (base PPA); and wherein a second TP of the pair of TPs comprises a nucleic acid sequence comprising two segments, (i) a segment comprising a binding site for a second segment of the target nucleic acid, and (ii) a segment comprising a binding site for a second base PPA; (B) a pair of PPAs comprising the first and second PPAs, wherein the first PPA comprises a nucleic acid sequence comprising two segments, (i) a segment that binds to the first PPA binding site of the first TP, and (ii) a segment comprising a plurality of first pre-amplifier binding segment repeats (first PA-BSRs), wherein the first PA-BSRs comprise two segments, (ia) a segment comprising a binding site for a first pre-amplifier (first PA) and (ib) a segment comprising a binding site for a second PA, wherein the segments of the first PPA are in the order (i), (ia), (ib); and wherein the second PPA comprises a nucleic acid sequence comprising two segments, (i) a segment that binds to the second PPA binding site of the second TP, and (ii) a segment comprising a plurality of second PA-BSRs, wherein the second PA-BSRs comprise two segments, (iia) a segment comprising a binding site for the second PA and (iib) a segment comprising a binding site for the first PA, wherein the segments of the second PPA are in the order (i), (iia), (iib); (C) a plurality of the first PAs and the second PAs, wherein the first PAs comprise a nucleic acid sequence comprising three segments, (i) a segment complementary to the second PA-BSR, (ii) a segment complementary to the first PA-BSR, and (iii) a segment comprising a plurality of amplifier binding segment repeats (AMP-BSRs); and wherein the second PAs comprise a nucleic acid sequence comprising three segments, (i) a segment complementary to the first PA-BSR, (ii) a segment complementary to the second PA-BSR, and (iii) a segment comprising a plurality of amplifier binding segment repeats (AMP-BSRs); (D) a plurality of amplifiers (AMPs), wherein the AMPs comprise a nucleic acid sequence comprising two segments, (i) a segment complementary to the AMP-BSRs, and (ii) a segment comprising a plurality of label probe binding segment repeats (LP-BSRs); and (E) a plurality of label probes (LPs), wherein the LPs comprise a nucleic acid sequence comprising two segments, (i) a segment complementary to the LP-BSRs, and (ii) a segment that is detectable; wherein the respective binding sites and complementary segments are hybridized to form the SGC (see FIG. 5).

In another embodiment, the PPAs comprise base PPAs and extension PPAs (see FIG. 5 and FIG. 2A). In another embodiment, the PAs comprise base PAs and extension PAs (see FIG. 5 and FIG. 2B). In another embodiment, the AMPs comprise base AMPs and extension AMPs (see FIG. 5 and FIG. 2C).

In another embodiment, the base and extension molecules are tethered by a configuration comprising: wherein the binding sites between the first base PPA and the first extension PPA and/or between the first extension PPAs comprise complementary sequences, and wherein the binding sites between the second base PPA and the second extension PPA and/or between the second extension PPAs comprise complementary sequences; and/or wherein the binding sites between the base PA and extension PA, and or the binding sites between the base AMP and extension AMP comprise complementary sequences (see FIG. 5 and FIG. 3B).

In another embodiment, the base and extension molecules are tethered by a configuration comprising: wherein the composition further comprises a pair of bridges comprising a first bridge and second bridge, wherein the first bridge comprises two sections that bind to the first extension PPA binding site of the first base PPA and/or the first extension PPA binding site of the first extension PPA; and wherein the second bridge comprises two sections that bind to the second extension PPA binding site of the second base PPA and/or the second extension PPA binding site of the second extension PPA; wherein binding of the bridge tethers the extension PPA to the base PPA and/or the extension PPAs to each other; or wherein the composition further comprises a bridge, wherein the bridge comprises two sections that bind to the extension PA or AMP binding site of the base PA or AMP and/or the extension PA or AMP binding site of the extension PA or AMP, wherein binding of the bridge tethers the extension PA or AMP to the base PA or AMP and/or the extension PAs or AMPs to each other (see FIG. 5 and FIG. 3C).

In another embodiment, the base and extension molecules are tethered by a configuration comprising: wherein the composition further comprises a pair of bridges comprising a first bridge and second bridge, wherein the first bridge comprises two sections, (i) a section that binds to the first extension PPA binding site of the first base PPA and/or the first extension PPA binding site of the first extension PPA, and (ii) a section that binds to the second extension PPA binding site of the second extension PPA; wherein the second bridge comprises two sections, (i) a section that binds to the second extension PPA binding site of the second base PPA and/or the second extension PPA binding site of the second extension PPA, and (ii) a section that binds to the first extension PPA binding site of the first extension PPA; wherein binding of the bridge tethers the second extension PPA to the first base PPA or the second extension PPA to the first extension PPA, and tethers the first extension PPA to the second base PPA or the first extension PPA to the second extension PPA (see FIG. 5 and FIG. 3D).

In another embodiment, the base and extension molecules are tethered by a configuration comprising: wherein the first base PPA and/or the first extension PPA comprises a fourth segment (iv) comprising a binding site for the second extension PPA, and wherein the second base PPA and/or the second extension PPA comprises a fourth segment (iv) comprising a binding site for the first extension PPA, wherein the segments of the PPA are in the order (i), (ii), (iv), (iii) (see FIG. 2A and FIG. 4, middle circle).

In another embodiment, (I) wherein the first TP further comprises a third segment (iii) comprising a binding site for the second PPA; wherein the second TP further comprise a third segment (iii) comprising a binding site for the first PPA; and wherein the segments are in the order (i), (iii), (ii); and (II) wherein the first base PPA further comprise a fourth segment (iv) comprising a binding site for the second TP; wherein the second base PPA further comprises a fourth segment (iv) comprising a binding site for the first TP; wherein the segments are in the order (iv), (i), (ii), (iii); or wherein the first PPA further comprise a third segment (iii) comprising a binding site for the second TP; wherein the second PPA further comprises a third segment (iii) comprising a binding site for the first TP; wherein the segments are in the order (iii), (i), (ii) (see FIG. 4A, lower circle).

In another embodiment, the invention provides any of the compositions described above or disclosed herein, the composition further comprises a second SGC, wherein the second SGC comprises a second target that is different from the target of the first SGC, wherein the SGC comprises an SGC configuration of any one of SGCs describe above independently of the configuration of the first SGC, and wherein the second SGC is distinguishable from the first SGC (see FIG. 6).

In another embodiment, the composition further comprises a third SGC, wherein the third SGC comprises a third target that is different from the target of the first target and the second target, wherein the SGC comprises an SGC configuration of any one of SGCs described above or disclosed herein independently of the configuration of the first SGC and/or the second SGC, and wherein the third SGC is distinguishable from the first and second SGC.

In another embodiment, the compositions of the invention further comprise a target nucleic acid to which the pair of TPs bind. In another embodiment, the compositions of the invention further comprise a cell.

In another embodiment, the invention provides a method of detecting a target nucleic acid, comprising contacting a sample nucleic acid with the components for assembly of an SGC as described above or disclosed herein, including in any of FIGS. 2-6, assembling an SGC on the target nucleic acid, and detecting the target nucleic acid. In one embodiment, the nucleic acid is in a cell. In one embodiment, the cell is analyzed in an in situ assay. In one embodiment, the cell is on a slide.

It is understood that configurations of the compositions of the invention can be in any desired order so long as the components can bind to provide an SGC for detection of a target nucleic acid. Furthermore, the configurations of binding segments of a component of an SGC can be arranged in any desired order, relative to the 5' or 3' end of a nucleic acid molecule, so long as the binding segments provide for assembly of an SGC for detection of a target nucleic acid. It is further understood that, when an orientation of segments is referenced as being in the order (i), (ii), (iii) without reference to the 5' or 3' end of the nucleic acid molecule, it is understood that such an orientation can be in the order from 5' to 3' (i), (ii), (iii) or (iii), (ii), (i). It is additionally understood that other orientations are possible, as described herein. Furthermore, when two similar components are used (for example, first and second TPs, first and second base PPAs, first and second extension PPAs, and the like), it is understood that the two similar components can have the order of segments independently selected, for example, a first base PPA in the order (i), (ii), (iii), and a second base PPA in the order (ii), (iii), (i), and so forth.

In one embodiment, the invention provides a composition comprising a Signal Generating Complex (SGC), wherein the composition comprises (A) a pair of target probes (TPs), wherein a first TP of the pair of TPs comprises a nucleic acid sequence comprising two segments, (i) a segment comprising a binding site for a first segment of a target nucleic acid, and (ii) a segment comprising a binding site for a first base pre-pre-amplifier (base PPA); and wherein a second TP of the pair of TPs comprises a nucleic acid sequence comprising two segments, (i) a segment comprising a binding site for a second segment of the target nucleic acid, and (ii) a segment comprising a binding site for a second base PPA; (B) a pair of base PPAs comprising the first and second base PPAs, wherein the first base PPA comprises a nucleic acid sequence comprising three segments, (i) a segment that binds to the first base PPA binding site of the first TP, (ii) a segment comprising a plurality of first pre-amplifier binding segment repeats (first PA-BSRs), and (iii) a segment comprising a binding site for a first extension pre-pre-amplifier (extension PPA); and wherein the second base PPA comprises a nucleic acid sequence comprising three segments, (i) a segment that binds to the second base PPA binding site of the second TP, (ii) a segment comprising a plurality of second pre-amplifier binding segment repeats (second PA-BSRs), and (iii) a segment comprising a binding site for a second extension PPA; wherein the first and second PA-BSRs are different sequences; (C) a set of extension PPAs comprising the first and second extension PPAs, wherein the first extension PPA comprises a nucleic acid sequence comprising two segments, (i) a segment that binds to the first extension PPA binding site of the first base PPA, and (ii) a segment comprising a plurality of the first PA-BSRs; and wherein the second extension PPA comprises a nucleic acid sequence comprising two segments, (i) a segment that binds to the second extension PPA binding site of the second base PPA, and (ii) a segment comprising a plurality of the second PA-BSRs; (D) a plurality of pre-amplifiers (PAs), wherein the PAs comprise a nucleic acid sequence comprising three segments, (i) a segment complementary to the first PA-BSR, (ii) a segment complementary to the second PA-BSR, and (iii) a segment comprising a plurality of amplifier binding segment repeats (AMP-BSRs); (E) a plurality of amplifiers (AMPs), wherein the AMPs comprise a nucleic acid sequence comprising two segments, (i) a segment complementary to the AMP-BSRs, and (ii) a segment comprising a plurality of label probe binding segment repeats (LP-BSRs); and (F) a plurality of label probes (LPs), wherein the LPs comprise a nucleic acid sequence comprising two segments, (i) a segment complementary to the LP-BSRs, and (ii) a segment that is detectable; wherein the respective binding sites and complementary segments are hybridized to form the SGC (see FIG. 2A).

In some embodiments, the segments of the first and second base PPAs are in the order from 5' to 3' (i), (ii), (iii); (i), (iii), (ii); (ii), (i), (iii); (ii), (iii), (i); (iii), (i), (ii); or (iii), (ii), (i). In some embodiments, the segments of the PAs are in the order from 5' to 3' (i), (ii), (iii); (i), (iii), (ii); (ii), (i), (iii); (ii), (iii), (i); (iii), (i), (ii); or (iii), (ii), (i).

In one embodiment, the set of extension PPAs comprises at least one additional first extension PPA and at least one additional second extension PPA, wherein the additional first extension PPA comprises a nucleic acid sequence comprising two segments, (i) a segment comprising a binding site for the first extension PPA, and (ii) a segment comprising a plurality of the first PA-BSRs; wherein the additional second extension PPA comprises a nucleic acid sequence comprising two segments, (i) a segment comprising a binding site for the second extension PPA, and (ii) a segment comprising a plurality of the second PA-BSRs; and wherein the at least one additional first PPA optionally comprises a third segment (iii) comprising a second binding site for the first extension PPAs, and the at least one additional second PPA optionally comprises a third segment (iii) comprising a second binding site for the second extension PPAs.

In some embodiments, the segments of the first PPA are in the order from 5' to 3' (i), (ii), (iii); (i), (iii), (ii); (ii), (i), (iii); (ii), (iii), (i); (iii), (i), (ii); or (iii), (ii), (i).

In another embodiment, the binding sites between the first base PPA and the first extension PPA and/or between the extension PPAs comprise complementary sequences, and wherein the binding sites between the second base PPA and the second extension PPA and/or between the second extension PPAs comprise complementary sequences (see FIGS. 2A and 3B).

In another embodiment, the composition further comprises a pair of bridges comprising a first bridge and second bridge, wherein the first bridge comprises two sections that bind to the first extension PPA binding site of the first base PPA and/or the first extension PPA binding site of the first extension PPA; and wherein the second bridge comprises two sections that bind to the second extension PPA binding site of the second base PPA and/or the second extension PPA binding site of the second extension PPA; wherein binding of the bridge tethers the extension PPA to the base PPA and/or the extension PPAs to each other (see FIGS. 2A and 3C).

In another embodiment, the composition further comprises a pair of bridges comprising a first bridge and second bridge, wherein the first bridge comprises two sections, (i) a section that binds to the first extension PPA binding site of the first base PPA and/or the first extension PPA binding site of the first extension PPA, and (ii) a section that binds to the second extension PPA binding site of the second extension PPA; wherein the second bridge comprises two sections, (i) a section that binds to the second extension PPA binding site of the second base PPA and/or the second extension PPA binding site of the second extension PPA, and (ii) a section that binds to the first extension PPA binding site of the first extension PPA; wherein binding of the bridge tethers the second extension PPA to the first base PPA or the second extension PPA to the first extension PPA, and tethers the first extension PPA to the second base PPA or the first extension PPA to the second extension PPA (see FIGS. 2A and 3D).

In another embodiment, the first base PPA and/or the first extension PPA comprises a fourth segment (iv) comprising a binding site for the second extension PPA, and wherein the second base PPA and/or the second extension PPA comprises a fourth segment (iv) comprising a binding site for the first extension PPA (see FIG. 2A and FIG. 4 middle circle).

In some embodiments, the segments of the first and second base PPAs and/or first and second extension PPAs are in the order from 5' to 3' (i), (ii), (iii), (iv); (i), (ii), (iv), (iii); (i), (iii), (ii), (iv); (i), (iii), (iv), (ii); (i), (iv), (ii), (iii); (i), (iv), (iii), (ii); (ii), (i), (iii), (iv); (ii), (i), (iv), (iii); (ii), (iii), (i), (iv); (ii), (iii), (iv), (i); (ii), (iv), (i), (iii); (ii), (iv), (iii), (i); (iii), (i), (ii), (iv); (iii), (i), (iv), (ii); (iii), (ii), (i), (iv); (iii), (ii), (iv), (i); (iii), (iv), (i), (ii); (iii), (iv), (ii), (i); (iv), (i), (ii), (iii); (iv), (i), (iii), (ii); (iv), (ii), (i), (iii); (iv), (ii), (iii), (i); (iv), (iii), (i), (ii); or (iv), (iii), (ii), (i).

In another embodiment, the invention provides a composition comprising a Signal Generating Complex (SGC), wherein the composition comprises (A) a pair of target probes (TPs), wherein a first TP of the pair of TPs comprises a nucleic acid sequence comprising two segments, (i) a segment comprising a binding site for a first segment of a target nucleic acid, and (ii) a segment comprising a binding site for a first pre-pre-amplifier (PPA); and wherein a second TP of the pair of TPs comprises a nucleic acid sequence comprising two segments, (i) a segment comprising a binding site for a second segment of the target nucleic acid, and (ii) a segment comprising a binding site for a second PPA; (B) a pair of PPAs comprising the first and second PPAs, wherein the first PPA comprises a nucleic acid sequence comprising two segments, (i) a segment that binds to the first PPA binding site of the first TP, and (ii) a segment comprising a plurality of first pre-amplifier binding segment repeats (first PA-BSRs); and wherein the second PPA comprises a nucleic acid sequence comprising two segments, (i) a segment that binds to the second PPA binding site of the second TP, and (ii) a segment comprising a plurality of second PA-BSRs, wherein the first and second PA-BSRs are different sequences; (C) a plurality of base pre-amplifiers (base PAs), wherein the base PAs comprise a nucleic acid sequence comprising four segments (i) a segment complementary to the first PA-BSRs, (ii) a segment complementary to the second PA-BSRs, (iii) a segment comprising a plurality of amplifier binding segment repeats (AMP-BSRs), and (iv) a segment that binds to an extension pre-amplifier (extension PA); (D) a plurality of extension PAs, wherein the extension PAs comprise a nucleic acid sequence comprising two segments (i) a segment that binds to the extension PA binding site of the base PAs and (ii) a plurality of amplifier binding segment repeats (AMP-BSRs); and wherein the extension PAs optionally comprise a third segment (iii) comprising a binding site for the extension PAs; (E) a plurality of amplifiers (AMPs), wherein the AMPS comprise a nucleic acid sequence comprising two segments, (i) a segment complementary to the AMP-BSRs, and (ii) a segment comprising a plurality of label probe binding segment repeats (LP-BSRs); and (F) a plurality of label probes (LPs), wherein the LPs comprise a nucleic acid sequence comprising two segments, (i) a segment complementary to the LP-BSRs, and (ii) a segment that is detectable; wherein the respective binding sites and complementary segments are hybridized to form the SGC (see FIG. 2B).

In some embodiments, the segments of the base PA are in the order, from 5' to 3' (i), (ii), (iii), (iv); (i), (ii), (iv), (iii); (i), (iii), (ii), (iv); (i), (iii), (iv), (ii); (i), (iv), (ii), (iii); (i), (iv), (iii), (ii); (ii), (i), (iii), (iv); (ii), (i), (iv), (iii); (ii), (iii), (i), (iv); (ii), (iii), (iv), (i); (ii), (iv), (i), (iii); (ii), (iv), (iii), (i); (iii), (i), (ii), (iv); (iii), (i), (iv), (ii); (iii), (ii), (i), (iv); (iii), (ii), (iv), (i); (iii), (iv), (i), (ii); (iii), (iv), (ii), (i); (iv), (i), (ii), (iii); (iv), (i), (iii), (ii); (iv), (ii), (i), (iii); (iv), (ii), (iii), (i); (iv), (iii), (i), (ii); or (iv), (iii), (ii), (i). In some embodiments, the segments of the extension PAs are in the order from 5' to 3' (i), (ii), (iii); (i), (iii), (ii); (ii), (i), (iii); (ii), (iii), (i); (iii), (i), (ii); or (iii), (ii), (i).

In some embodiments, the binding sites between the base PAs and the extension PAs comprise complementary sequences (see FIGS. 2B and 3B). In some embodiments, the composition further comprises a bridge, wherein the bridge comprises two sections that bind to the extension PA binding site of the base PA and/or the extension PA binding site of the extension PA, wherein binding of the bridge tethers the extension PA to the base PA and/or the extension PAs to each other (see FIGS. 2B and 3C).

In one embodiment, the invention provides a composition comprising a Signal Generating Complex (SGC), wherein the composition comprises (A) a pair of target probes (TPs), wherein a first TP of the pair of TPs comprises a nucleic acid sequence comprising two segments, (i) a segment comprising a binding site for a first segment of a target nucleic acid, and (ii) a segment comprising a binding site for a first pre-pre-amplifier (PPA); and wherein a second TP of the pair of TPs comprises a nucleic acid sequence comprising two segments, (i) a segment comprising a binding site for a second segment of the target nucleic acid, and (ii) a segment comprising a binding site for a second PPA; (B) a pair of PPAs comprising the first and second PPAs, wherein the first PPA comprises a nucleic acid sequence comprising two segments, (i) a segment that binds to the first PPA binding site of the first TP, and (ii) a segment comprising a plurality of first pre-amplifier binding segment repeats (first PA-BSRs); and wherein the second PPA comprises a nucleic acid sequence comprising two segments, (i) a segment that binds to the second PPA binding site of the second TP, and (ii) a segment comprising a plurality of second PA-BSRs, wherein the first and second PA-BSRs are different sequences; (C) a plurality of pre-amplifiers (PAs), wherein the PAs comprise a nucleic acid sequence comprising three segments, (i) a segment complementary to the first PA-BSR, (ii) a segment complementary to the second PA-BSR, and (iii) a segment comprising a plurality of amplifier binding segment repeats (AMP-BSRs); (D) a plurality of base amplifiers (base AMPs), wherein the base AMPs comprise a nucleic acid sequence comprising three segments (i) a segment complementary to the AMP-BSRs, (ii) a segment comprising a plurality of label probe binding segment repeats (LP-BSRs), and (iii) a segment that binds to an extension amplifier (extension AMP); (E) a plurality of extension AMPs, wherein the extension AMPs comprise a nucleic acid sequence comprising two segments (i) a segment that binds to the extension AMP binding site of the base AMP, and (ii) a segment comprising a plurality of label probe binding segment repeats (LP-BSRs); and wherein the extension AMPs optionally comprise a third segment (iii) comprising a binding site for the extension PAs; and (F) a plurality of label probes (LPs), wherein the LPs comprise a nucleic acid sequence comprising two segments (i) a segment complementary to the LP-BSRs, and (ii) a segment that is detectable; wherein the respective binding sites and complementary segments are hybridized to form the SGC (see FIG. 2C).

In some embodiments, the segments of the PAs are in the order from 5' to 3' (i), (ii), (iii); (i), (iii), (ii); (ii), (i), (iii); (ii), (iii), (i); (iii), (i), (ii); or (iii), (ii), (i). In some embodiments, the segments of the base AMPs are in the order from 5' to 3' (i), (ii), (iii); (i), (iii), (ii); (ii), (i), (iii); (ii), (iii), (i); (iii), (i), (ii); or (iii), (ii), (i). In some embodiments, the segments of the extension AMPs are in the order from 5' to 3' (i), (ii), (iii); (i), (iii), (ii); (ii), (i), (iii); (ii), (iii), (i); (iii), (i), (ii); or (iii), (ii), (i).

In some embodiments, the binding sites between the base AMPs and the extension AMPs comprise complementary sequences (see FIGS. 2C and 3B). In some embodiments, the composition further comprises a bridge, wherein the bridge comprises two sections that bind to the extension AMP binding site of the base AMP and/or the extension AMP binding site of the extension AMP, wherein binding of the bridge tethers the extension AMP to the base AMP and/or the extension AMPs to each other (see FIGS. 2C and 3C).

In some embodiments, (I) wherein the first TP further comprises a third segment (iii) comprising a binding site for the second PPA; wherein the second TP further comprise a third segment (iii) comprising a binding site for the first PPA; and (II) wherein the first base PPA further comprises a fourth segment (iv) comprising a binding site for the second TP; wherein the second base PPA further comprises a fourth segment (iv) comprising a binding site for the first TP; or wherein the first PPA further comprises a third segment (iii) comprising a binding site for the second TP; wherein the second PPA further comprises a third segment (iii) comprising a binding site for the first TP (see FIG. 14A, lower circle).

In some embodiments, the segments of the first and second TPs are in the order from 5' to 3' (i), (ii), (iii); (i), (iii), (ii); (ii), (i), (iii); (ii), (iii), (i); (iii), (i), (ii); or (iii), (ii), (i). In some embodiments, the segments of the first and second base PPAs are in the order, from 5' to 3' (i), (ii), (iii), (iv); (i), (ii), (iv), (iii); (i), (iii), (ii), (iv); (i), (iii), (iv), (ii); (i), (iv), (ii), (iii); (i), (iv), (iii), (ii); (ii), (i), (iii), (iv); (ii), (i), (iv), (iii); (ii), (iii), (i), (iv); (ii), (iii), (iv), (i); (ii), (iv), (i), (iii); (ii), (iv), (iii), (i); (iii), (i), (ii), (iv); (iii), (i), (iv), (ii); (iii), (ii), (i), (iv); (iii), (ii), (iv), (i); (iii), (iv), (i), (ii); (iii), (iv), (ii), (i); (iv), (i), (ii), (iii); (iv), (i), (iii), (ii); (iv), (ii), (i), (iii); (iv), (ii), (iii), (i); (iv), (iii), (i), (ii); or (iv), (iii), (ii), (i). In some embodiments, the segments of the first and second PPAs are in the order from 5' to 3' (i), (ii), (iii); (i), (iii), (ii); (ii), (i), (iii); (ii), (iii), (i); (iii), (i), (ii); or (iii), (ii), (i).

In one embodiment, the invention provides a composition comprising a Signal Generating Complex (SGC), wherein the composition comprises (A) a pair of target probes (TPs), wherein a first TP of the pair of TPs comprises a nucleic acid sequence comprising two segments, (i) a segment comprising a binding site for a first segment of a target nucleic acid, and (ii) a segment comprising a binding site for a first base pre-pre-amplifier (base PPA); and wherein a second TP of the pair of TPs comprises a nucleic acid sequence comprising two segments, (i) a segment comprising a binding site for a second segment of the target nucleic acid, and (ii) a segment comprising a binding site for a second base PPA; (B) a pair of PPAs comprising the first and second PPAs, wherein the first PPA comprises a nucleic acid sequence comprising two segments, (i) a segment that binds to the first PPA binding site of the first TP, and (ii) a segment comprising a plurality of first pre-amplifier binding segment repeats (first PA-BSRs), wherein the first PA-BSRs comprise two segments, (ia) a segment comprising a binding site for a first pre-amplifier (first PA) and (ib) a segment comprising a binding site for a second PA; and wherein the second PPA comprises a nucleic acid sequence comprising two segments, (i) a segment that binds to the second PPA binding site of the second TP, and (ii) a segment comprising a plurality of second PA-BSRs, wherein the second PA-BSRs comprise two segments, (iia) a segment comprising a binding site for the second PA and (iib) a segment comprising a binding site for the first PA; (C) a plurality of the first PAs and the second PAs, wherein the first PAs comprise a nucleic acid sequence comprising three segments, (i) a segment complementary to the second PA-BSR, (ii) a segment complementary to the first PA-BSR, and (iii) a segment comprising a plurality of amplifier binding segment repeats (AMP-BSRs); and wherein the second PAs comprise a nucleic acid sequence comprising three segments, (i) a segment complementary to the first PA-BSR, (ii) a segment complementary to the second PA-BSR, and (iii) a segment comprising a plurality of amplifier binding segment repeats (AMP-BSRs); (D) a plurality of amplifiers (AMPs), wherein the AMPs comprise a nucleic acid sequence comprising two segments, (i) a segment complementary to the AMP-BSRs, and (ii) a segment comprising a plurality of label probe binding segment repeats (LP-BSRs); and (E) a plurality of label probes (LPs), wherein the LPs comprise a nucleic acid sequence comprising two segments, (i) a segment complementary to the LP-BSRs, and (ii) a segment that is detectable; wherein the respective binding sites and complementary segments are hybridized to form the SGC (see FIG. 5).

In some embodiments, the segments of the first PPA are in the order from 5' to 3' (i), (ia), (ib); (i), (ib), (ia); (ia), (i), (ib); (ia), (ib), (i); (ib), (i), (ia); or (ib), (ia), (i). In some embodiments, the segments of the second PPA are in the order from 5' to 3' (i), (iia), (iib); (i), (iib), (iia); (iia), (i), (iib); (iia), (iib), (i); (iib), (i), (iia); or (iib), (iia), (i).

In some embodiments, the PPAs comprise base PPAs and extension PPAs (see FIGS. 5 and 2A). In some embodiments, the PAs comprise base PAs and extension PAs (see FIGS. 5 and 2B). In some embodiments, the AMPs comprise base AMPs and extension AMPs (see FIGS. 5 and 2C).

In some embodiments, the base and extension molecules are tethered by a configuration comprising wherein the binding sites between the first base PPA and the first extension PPA and/or between the first extension PPAs comprise complementary sequences, and wherein the binding sites between the second base PPA and the second extension PPA and/or between the second extension PPAs comprise complementary sequences; and/or wherein the binding sites between the base PA and extension PA, and or the binding sites between the base AMP and extension AMP comprise complementary sequences (see FIGS. 5 and 3B).

In some embodiments, the base and extension molecules are tethered by a configuration comprising wherein the composition further comprises a pair of bridges comprising a first bridge and second bridge, wherein the first bridge comprises two sections that bind to the first extension PPA binding site of the first base PPA and/or the first extension PPA binding site of the first extension PPA; and wherein the second bridge comprises two sections that bind to the second extension PPA binding site of the second base PPA and/or the second extension PPA binding site of the second extension PPA; wherein binding of the bridge tethers the extension PPA to the base PPA and/or the extension PPAs to each other; or wherein the composition further comprises a bridge, wherein the bridge comprises two sections that bind to the extension PA or AMP binding site of the base PA or AMP and/or the extension PA or AMP binding site of the extension PA or AMP, wherein binding of the bridge tethers the extension PA or AMP to the base PA or AMP and/or the extension PAs or AMPs to each other (FIGS. 5 and 3C).

In some embodiments, the base and extension molecules are tethered by a configuration comprising wherein the composition further comprises a pair of bridges comprising a first bridge and second bridge, wherein the first bridge comprises two sections, (i) a section that binds to the first extension PPA binding site of the first base PPA and/or the first extension PPA binding site of the first extension PPA, and (ii) a section that binds to the second extension PPA binding site of the second extension PPA; wherein the second bridge comprises two sections, (i) a section that binds to the second extension PPA binding site of the second base PPA and/or the second extension PPA binding site of the second extension PPA, and (ii) a section that binds to the first extension PPA binding site of the first extension PPA; wherein binding of the bridge tethers the second extension PPA to the first base PPA or the second extension PPA to the first extension PPA, and tethers the first extension PPA to the second base PPA or the first extension PPA to the second extension PPA (see FIGS. 5 and 3D).

In some embodiments, the base and extension molecules are tethered by a configuration comprising wherein the first base PPA and/or the first extension PPA comprises a fourth segment (iv) comprising a binding site for the second extension PPA, and wherein the second base PPA and/or the second extension PPA comprises a fourth segment (iv) comprising a binding site for the first extension PPA (see FIGS. 5 and 2A and FIG. 4, middle circle).

In some embodiments, the segments of the first and second PPAs and/or the first and second extension PPAs are in the order from 5' to 3' (i), (ii), (iii), (iv); (i), (ii), (iv), (iii); (i), (iii), (ii), (iv); (i), (iii), (iv), (ii); (i), (iv), (ii), (iii); (i), (iv), (iii), (ii); (ii), (i), (iii), (iv); (ii), (i), (iv), (iii); (ii), (iii), (i), (iv); (ii), (iii), (iv), (i); (ii), (iv), (i), (iii); (ii), (iv), (iii), (i); (iii), (i), (ii), (iv); (iii), (i), (iv), (ii); (iii), (ii), (i), (iv); (iii), (ii), (iv) (i); (iii), (iv), (i), (ii); (iii), (iv), (ii), (i); (iv), (i), (ii), (iii); (iv), (i), (iii), (ii); (iv), (ii), (i), (iii); (iv), (ii), (iii), (i); (iv), (iii), (i), (ii); or (iv), (iii), (ii), (i).

In some embodiments, (I) wherein the first TP further comprises a third segment (iii) comprising a binding site for the second PPA; wherein the second TP further comprise a third segment (iii) comprising a binding site for the first PPA; and (II) wherein the first base PPA further comprises a fourth segment (iv) comprising a binding site for the second TP; wherein the second base PPA further comprises a fourth segment (iv) comprising a binding site for the first TP; or wherein the first PPA further comprises a third segment (iii) comprising a binding site for the second TP; wherein the second PPA further comprises a third segment (iii) comprising a binding site for the first TP (see FIG. 5 and FIG. 4, lower circle).

In some embodiments, the segments of the first and second TPs are in the order from 5' to 3' (i), (ii), (iii); (i), (iii), (ii); (ii), (i), (iii); (ii), (iii), (i); (iii), (i), (ii); or (iii), (ii), (i). In some embodiments, the segments of the first and second base PPAs are in the order from 5' to 3' (i), (ii), (iii), (iv); (i), (ii), (iv), (iii); (i), (iii), (ii), (iv); (i), (iii), (iv), (ii); (i), (iv), (ii), (iii); (i), (iv), (iii), (ii); (ii), (i), (iii), (iv); (ii), (i), (iv), (iii); (ii), (iii), (i), (iv); (ii), (iii), (iv), (i); (ii), (iv), (i), (iii); (ii), (iv), (iii), (i); (iii), (i), (ii), (iv); (iii), (i), (iv), (ii); (iii), (ii), (i), (iv); (iii), (ii), (iv) (i); (iii), (iv), (i), (ii); (iii), (iv), (ii), (i); (iv), (i), (ii), (iii); (iv), (i), (iii), (ii); (iv), (ii), (i), (iii); (iv), (ii), (iii), (i); (iv), (iii), (i), (ii); or (iv), (iii), (ii), (i). In some embodiments, the segments of the first and second PPAs are in the order from 5' to 3' (i), (ii), (iii); (i), (iii), (ii); (ii), (i), (iii); (ii), (iii), (i); (iii), (i), (ii); or (iii), (ii), (i).

In some embodiments, the composition further comprises a second SGC, wherein the second SGC comprises a second target that is different from a first target, wherein the SGC comprises an SGC configuration of any one of the SGCs described above independently of the configuration of the first SGC, and wherein the second SGC is distinguishable from the first SGC (see FIG. 6).

In some embodiments, the composition further comprises a third SGC, wherein the third SGC comprises a third target that is different from a first target and a second target, wherein the SGC comprises an SGC configuration of any one of the SGCs described above independently of the configuration of the first SGC and/or the second SGC, and wherein the third SGC is distinguishable from the first and second SGC.

In some embodiments, the composition further comprises a target nucleic acid to which the pair of TPs bind. In some embodiments, the composition comprises a cell, for example, a cell comprising the target nucleic acid(s).

In some embodiments, the invention provides a method of detecting a target nucleic acid, comprising contacting a sample nucleic acid with the components for assembly of an SGC as described above, assembling an SGC on the target nucleic acid, and detecting the target nucleic acid. In some embodiments, the nucleic acid is in a cell.

As described herein, the methods of the invention generally relate to in situ detection of target nucleic acids. Methods for in situ detection of nucleic acids are well known to those skilled in the art (see, for example, US 2008/0038725; US 2009/0081688; Hicks et al., *J. Mol. Histol.* 35:595-601 (2004)). As used herein, "in situ hybridization" or "ISH" refers to a type of hybridization that uses a directly or indirectly labeled complementary DNA or RNA strand, such as a probe, to bind to and localize a specific nucleic acid, such as DNA or RNA, in a sample, in particular a portion or section of tissue (in situ). The probe types can be double stranded DNA (dsDNA), single stranded DNA (ssDNA), single stranded complimentary RNA (sscRNA), messenger RNA (mRNA), micro RNA (miRNA), ribosomal RNA, mitochondrial RNA, and/or synthetic oligonucleotides. The term "fluorescent in situ hybridization" or "FISH" refers to a type of ISH utilizing a fluorescent label. The term "chromogenic in situ hybridization" or "CISH" refers to a type of ISH with a chromogenic label. ISH, FISH and CISH methods are well known to those skilled in the art (see, for example, Stoler, *Clinics in Laboratory Medicine* 10(1):215-236 (1990); *In situ hybridization. A practical approach*, Wilkinson, ed., IRL Press, Oxford (1992); Schwarzacher and Heslop-Harrison, *Practical in situ hybridization*, BIOS Scientific Publishers Ltd, Oxford (2000)). Other exemplary methods for detecting nucleic acids have been described, for example, in US2007-0015188, US2008-0038725, US2009-0081688, US2011-0059866, US2011-0059442, US2012-0071343, US2012-0100540, US2012-0214152, US2013-0023433, US2013-0171621, US2014-0178869, US2013-0294826, US2014-0249040, US2014-0357509, US2015-0045251, US2016-0186245, US2016-0115555, US2016-0201117, US2017-0101672, each of which is incorporated herein by reference.

For the methods of the invention for in situ detection of nucleic acid targets in a cell, including but not limited to in situ hybridization or flow cytometry, the cell is optionally fixed and/or permeabilized before hybridization of the target probes. Fixing and permeabilizing cells can facilitate retaining the nucleic acid targets in the cell and permit the target probes, label probes, amplifiers, pre-amplifiers, pre-pre-amplifiers, and so forth, to enter the cell and reach the target nucleic acid molecule. The cell is optionally washed to remove materials not captured to a nucleic acid target. The cell can be washed after any of various steps, for example, after hybridization of the target probes to the nucleic acid targets to remove unbound target probes, after hybridization of the pre-pre-amplifiers, pre-amplifiers, amplifiers, and/or label probes to the target probes, and the like. Methods for fixing and permeabilizing cells for in situ detection of nucleic acids, as well as methods for hybridizing, washing and detecting target nucleic acids, are also well known in the art (see, for example, US 2008/0038725; US 2009/0081688; Hicks et al., *J. Mol. Histol.* 35:595-601 (2004); Stoler, *Clinics in Laboratory Medicine* 10(1):215-236 (1990); *In situ hybridization. A practical approach*, Wilkinson, ed., IRL Press, Oxford (1992); Schwarzacher and Heslop-Harrison, *Practical in situ hybridization*, BIOS Scientific Publishers Ltd, Oxford (2000); Shapiro, *Practical Flow Cytometry* 3rd ed., Wiley-Liss, New York (1995); Ormerod, *Flow Cytometry*, 2nd ed., Springer (1999)). Exemplary fixing agents include, but are not limited to, aldehydes (formaldehyde, gluteraldehyde, and the like), acetone, alcohols (methanol, ethanol, and the like). Exemplary permeabilizing agents include, but are not limited to, alcohols (methanol, ethanol, and the like), acids (glacial acetic acid, and the like), detergents (Triton, NP-40, Tween™ 20, and the like), saponin, digitonin, Leucoperm™ (BioRad, Hercules, Calif.), and enzymes (for example, lysozyme, lipases, proteases and peptidases). Permeabilization can also occur by mechanical disruption, such as in tissue slices.

For in situ detection of double stranded nucleic acids, generally the sample is treated to denature the double stranded nucleic acids in the sample to provide accessibility for the target probes to bind by hybridization to a strand of the target double stranded nucleic acid. Conditions for denaturing double stranded nucleic acids are well known in the art, and include heat and chemical denaturation, for example, with base (NaOH), formamide, dimethyl sulfoxide, and the like (see Wang et al., *Environ. Health Toxicol.* 29:e2014007 (doi: 10.5620/eht.2014.29.e2014007) 2014; Sambrook et al., *Molecular Cloning: A Laboratory Manual*, Third Ed., Cold Spring Harbor Laboratory, New York (2001); Ausubel et al., *Current Protocols in Molecular Biology*, John Wiley and Sons, Baltimore, Md. (1999)). For example, NaOH, LiOH or KOH, or other high pH buffers (pH>11) can be used to denature double stranded nucleic acids such as DNA. In addition, heat and chemical denaturation methods can be used in combination.

As used herein, the term "plurality" is understood to mean two or more. Thus, a plurality can refer to, for example, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, 30 or more, 31 or more, 32 or more, 33 or more, 34 or more, 35 or more, 36 or more, 37 or more, 38 or more, 39 or more, 40 or more, 41 or more, 42 or more, 43 or more, 44 or more, 45 or more, 46 or more, 47 or more, 48 or more, 49 or more, 50 or more, 55 or more, 60 or more, 65 or more, 70 or more, 75 or more, 80 or more, 85 or more, 90 or more, 95 or more, 100 or more, 110 or more, 120 or more, 130 or more, 140 or more, 150 or more, 160 or more, 170 or more, 180 or more, 190 or more, 200 or more, 300 or more, 400 or more, 500 or more, 600 or more, 700 or more, 800 or more, 900 or more, or 1000 or more, or even a greater number, if desired for a particular use.

In designing binding sites between two nucleic acid sequences comprising complementary sequences, the complementary sequences can optionally be designed to maximize the difference in melting temperature ($dT_m$). This can be done by using melting temperature calculation algorithms known in the art (see, for example, SantaLucia, *Proc. Natl. Acad. Sci. U.S.A.* 95:1460-1465 (1998)). In addition, artificial modified bases such as Locked Nucleic Acid (LNA) or bridged nucleic acid (BNA) and naturally occurring 2'-O-methyl RNA are known to enhance the binding strength between complementary pairs (Petersen and Wengel, *Trends Biotechnol.* 21:74-81 (2003); Majlessi et al., *Nucl. Acids Res.* 26:2224-2229 (1998)). These modified bases can be strategically introduced into the binding site between components of an SGC, as desired.

One approach is to utilize modified nucleotides (LNA, BNA or 2'-O-methyl RNA). Because each modified base can increase the melting temperature, the length of binding regions between two nucleic acid sequences (i.e., complementary sequences) can be substantially shortened. The binding strength of a modified base to its complement is stronger, and the difference in melting temperatures ($dT_m$) is increased. Yet another embodiment is to use three modified bases (for example, three LNA, BNA or 2'-O-methyl RNA bases, or a combination of two or three different modified bases) in the complementary sequences of a nucleic acid component or between two nucleic acid components, for example of a signal generating complex (SGC), that are to be hybridized. Such components can be, for example, a pre-pre-amplifier, a pre-amplifier, an amplifier, a label probe, or a pair of target probes.

The modified bases, such as LNA or BNA, can be used in the segments of selected components of SGC, in particular those mediating binding between nucleic acid components, which increases the binding strength of the base to its complementary base, allowing a reduction in the length of the complementary segments (see, for example, Petersen and Wengel, *Trends Biotechnol.* 21:74-81 (2003); U.S. Pat. No. 7,399,845). Artificial bases that expand the natural 4-letter alphabet such as the Artificially Expanded Genetic Information System (AEGIS; Yang et al., *Nucl. Acids Res.* 34 (21): 6095-6101 (2006)) can be incorporated into the binding sites among the interacting components of the SGC. These artificial bases can increase the specificity of the interacting components, which in turn can allow lower stringency hybridization reactions to yield a higher signal.

The SGC also comprises a plurality of label probes (LPs). Each LP comprises a segment that is detectable. The detectable component can be directly attached to the LP, or the LP can hybridize to another nucleic acid that comprises the detectable component, i.e. the label. As used herein, a "label" is a moiety that facilitates detection of a molecule. Common labels in the context of the present invention include fluorescent, luminescent, light-scattering, and/or colorimetric labels. Suitable labels include enzymes, and fluorescent and chromogenic moieties, as well as radionuclides, substrates, cofactors, inhibitors, chemiluminescent moieties, magnetic particles, rare earth metals, metal isotopes, and the like. In a particular embodiment of the invention, the label is an enzyme. Exemplary enzyme labels include, but are not limited to Horse Radish Peroxidase (HRP), Alkaline Phosphatase (AP), β-galactosidase, glucose oxidase, and the like, as well as various proteases. Other labels include, but are not limited to, fluorophores, Dinitrophenyl (DNP), and the like. Labels are well known to those skilled in the art, as described, for example, in Hermanson, *Bioconjugate Techniques*, Academic Press, San Diego (1996), and U.S. Pat. Nos. 3,817,837; 3,850,752; 3,939,350; 3,996,345; 4,277,437; 4,275,149; and 4,366,241. Many labels are commercially available and can be used in methods and assays of the invention, including detectable enzyme/substrate combinations (Pierce, Rockford Ill.; Santa Cruz Biotechnology, Dallas Tex.; Invitrogen, Carlsbad Calif.). In a particular embodiment of the invention, the enzyme can utilize a chromogenic or fluorogenic substrate to produce a detectable signal, as described herein. Exemplary labels are described herein.

Any of a number of enzymes or non-enzyme labels can be utilized so long as the enzymatic activity or non-enzyme label, respectively, can be detected. The enzyme thereby produces a detectable signal, which can be utilized to detect a target nucleic acid. Particularly useful detectable signals are chromogenic or fluorogenic signals. Accordingly, particularly useful enzymes for use as a label include those for which a chromogenic or fluorogenic substrate is available. Such chromogenic or fluorogenic substrates can be converted by enzymatic reaction to a readily detectable chromogenic or fluorescent product, which can be readily detected and/or quantified using microscopy or spectroscopy. Such enzymes are well known to those skilled in the art, including but not limited to, horseradish peroxidase, alkaline phosphatase, β-galactosidase, glucose oxidase, and the like (see Hermanson, *Bioconjugate Techniques*, Academic Press, San Diego (1996)). Other enzymes that have well known chromogenic or fluorogenic substrates include various peptidases, where chromogenic or fluorogenic peptide substrates can be utilized to detect proteolytic cleavage reactions. The use of chromogenic and fluorogenic substrates is also well known in bacterial diagnostics, including but not limited to the use of α- and β-galactosidase, β-glucuronidase, 6-phospho-β-D-galatoside 6-phosphogalactohydrolase, β-gluosidase, α-glucosidase, amylase, neuraminidase, esterases, lipases, and the like (Manafi et al., *Microbiol. Rev.* 55:335-348 (1991)), and such enzymes with known chromogenic or fluorogenic substrates can readily be adapted for use in methods of the present invention.

Various chromogenic or fluorogenic substrates to produce detectable signals are well known to those skilled in the art and are commercially available. Exemplary substrates that can be utilized to produce a detectable signal include, but are not limited to, 3,3'-diaminobenzidine (DAB), 3,3',5,5'-tetramethylbenzidine (TMB), Chloronaphthol (4-CN)(4-chloro-1-naphthol), 2,2'-azino-bis(3-ethylbenzothiazoline-6-sulphonic acid) (ABTS), o-phenylenediamine dihydrochloride (OPD), and 3-amino-9-ethylcarbazole (AEC) for horseradish peroxidase; 5-bromo-4-chloro-3-indolyl-1-phosphate (BCIP), nitroblue tetrazolium (NBT), Fast Red (Fast Red TR/AS-MX), and p-Nitrophenyl Phosphate (PNPP) for alkaline phosphatase; 1-Methyl-3-indolyl-β-D-galactopyranoside and 2-Methoxy-4-(2-nitrovinyl)phenyl β-D-galactopyranoside for β-galactosidase; 2-Methoxy-4-(2-nitrovinyl)phenyl β-D-glucopyranoside for β-glucosidase; and the like. Exemplary fluorogenic substrates include, but are not limited to, 4-(Trifluoromethyl) umbelliferyl phosphate for alkaline phosphatase; 4-Methylumbelliferyl phosphate bis (2-amino-2-methyl-1,3-propanediol), 4-Methylumbelliferyl phosphate bis (cyclohexylammonium) and 4-Methylumbelliferyl phosphate for phosphatases; QuantaBlu™ and QuantaRed™ for horseradish peroxidase; 4-Methylumbelliferyl β-D-galactopyranoside, Fluorescein di(β-D-galactopyranoside) and Naphthofluorescein di-(β-D-galactopyranoside) for 3-galactosidase; 3-Acetylumbelliferyl β-D-glucopyranoside and 4-Methylumbelliferyl-β-D-glucopyranoside for 3-glucosidase; and 4-Methylumbelliferyl-α-D-galactopyranoside for α-galactosidase. Exemplary enzymes and substrates for producing a detectable signal are also described, for example, in US publication 2012/0100540. Various detectable enzyme substrates, including chromogenic or fluorogenic substrates, are well known and commercially available (Pierce, Rockford Ill.; Santa Cruz Biotechnology, Dallas Tex.; Invitrogen, Carlsbad Calif.; 42 Life Science; Biocare). Generally, the substrates are converted to products that form precipitates that are deposited at the site of the target nucleic acid. Other exemplary substrates include, but are not limited to, HRP-Green (42 Life Science), Betazoid DAB, Cardassian DAB, Romulin AEC, Bajoran Purple, Vina Green, Deep Space Black™, Warp Red™, Vulcan Fast Red and Ferangi Blue from Biocare (Concord Calif.; biocare.net/products/detection/chromogens).

Exemplary rare earth metals and metal isotopes suitable as a detectable label include, but are not limited to, lanthanide (III) isotopes such as 141Pr, 142Nd, 143Nd, 144Nd, 145Nd, 146Nd, 147Sm, 148Nd, 149Sm, 150Nd, 151Eu, 152Sm, 153Eu, 154Sm, 155Gd, 156Gd, 158Gd, 159Tb, 160Gd, 161Dy, 162Dy, 163Dy, 164Dy, 165Ho, 166Er, 167Er, 168Er, 169Tm, 170Er, 171Yb, 172Yb, 173Yb, 174Yb, 175Lu, and 176Yb Metal isotopes can be detected, for example, using time-of-flight mass spectrometry (TOF-MS) (for example, Fluidigm Helios and Hyperion systems, fluidigm.com/systems; South San Francisco, Calif.).

Biotin-avidin (or biotin-streptavidin) is a well known signal amplification system based on the fact that the two molecules have extraordinarily high affinity to each other and that one avidin/streptavidin molecule can bind four biotin molecules. Antibodies are widely used for signal amplification in immunohistochemistry and ISH. Tyramide signal amplification (TSA) is based on the deposition of a large number of haptenized tyramide molecules by peroxidase activity. Tyramine is a phenolic compound. In the presence of small amounts of hydrogen peroxide, immobilized Horse Radish Peroxidase (HRP) converts the labeled substrate into a short-lived, extremely reactive intermediate. The activated substrate molecules then very rapidly react with and covalently bind to electron-rich moieties of proteins, such as tyrosine, at or near the site of the peroxidase binding site. In this way, many hapten molecules conjugated to tyramide can be introduced at the hybridization site in situ. Subsequently, the deposited tyramide-hapten molecules can be visualized directly or indirectly. Such a detection system is described in more detail, for example, in U.S. publication 2012/0100540.

Embodiments described herein can utilize enzymes to generate a detectable signal using appropriate chromogenic or fluorogenic substrates. It is understood that, alternatively, a label probe can have a detectable label directly coupled to the nucleic acid portion of the label probe. Exemplary detectable labels are well known to those skilled in the art, including but not limited to chromogenic or fluorescent labels (see Hermanson, *Bioconjugate Techniques*, Academic Press, San Diego (1996)). Exemplary fluorophores useful as labels include, but are not limited to, rhodamine derivatives, for example, tetramethylrhodamine, rhodamine B, rhodamine 6G, sulforhodamine B, Texas Red (sulforhodamine 101), rhodamine 110, and derivatives thereof such as tetramethylrhodamine-5-(or 6), lissamine rhodamine B, and the like; 7-nitrobenz-2-oxa-1,3-diazole (NBD); fluorescein and derivatives thereof; napthalenes such as dansyl (5-dimethylaminonapthalene-1-sulfonyl); coumarin derivatives such as 7-amino-4-methylcoumarin-3-acetic acid (AMCA), 7-diethylamino-3-[(4'-(iodoacetyl)amino)phenyl]-4-methylcoumarin (DCIA), Alexa fluor dyes (Molecular Probes), and the like; 4,4-difluoro-4-bora-3a,4a-diaza-s-indacene (BODIPY™) and derivatives thereof (Molecular Probes; Eugene Oreg.); pyrenes and sulfonated pyrenes such as Cascade Blue' and derivatives thereof, including 8-methoxypyrene-1,3,6-trisulfonic acid, and the like; pyridyloxazole derivatives and dapoxyl derivatives (Molecular Probes); Lucifer Yellow (3,6-disulfonate-4-amino-naphthalimide) and derivatives thereof; CyDye™ fluorescent dyes (Amersham/GE Healthcare Life Sciences; Piscataway N.J.), ATTO 390, DyLight 395XL, ATTO 425, ATTO 465, ATTO 488, ATTO 490LS, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 643, ATTO 647, ATTO 647N, ATTO 655, ATTO Oxa12, ATTO 665, ATTO 680, ATTO 700, ATTO 725, ATTO 740, Cyan 500 NETS-Ester (ATTO-TECH, Siegen, Germany), and the like. Exemplary chromophores include, but are not limited to, phenolphthalein, malachite green, nitroaromatics such as nitrophenyl, diazo dyes, dabsyl (4-dimethylaminoazobenzene-4'-sulfonyl), and the like.

Well known methods such as microscopy, cytometry (e.g., mass cytometry, cytometry by time of flight (CyTOF), flow cytometry), or spectroscopy can be utilized to visualize chromogenic, fluorescent, or metal detectable signals associated with the respective target nucleic acids. In general, either chromogenic substrates or fluorogenic substrates, or chromogenic or fluorescent labels, or rare earth or metal isotopes, will be utilized for a particular assay, if different labels are used in the same assay, so that a single type of instrument can be used for detection of nucleic acid targets in the same sample.

As disclosed herein, the invention is based on building a signal-generating complex (SGC) bound to a target nucleic acid in order to detect the presence of the target nucleic acid in the cell. The components for building an SGC generally comprise nucleic acids such that nucleic acid hybridization reactions are used to bind the components of the SGC to the target nucleic acid. Methods of selecting appropriate regions and designing specific and selective reagents that bind to the target nucleic acids, in particular oligonucleotides or probes that specifically and selectively bind to a target nucleic acid, or other components of the SGC, are well known to those skilled in the art (see Sambrook et al., *Molecular Cloning: A Laboratory Manual*, Third Ed., Cold Spring Harbor Laboratory, New York (2001); Ausubel et al., Current Protocols in *Molecular Biology*, John Wiley and Sons, Baltimore, Md. (1999)). A desired specificity can be achieved using appropriate selection of regions of a target nucleic acid as well as appropriate lengths of a binding agent such as an oligonucleotide or probe, and such selection methods are well known to those skilled in the art. Thus, one skilled in the art will readily understand and can readily determine appropriate reagents, such as oligonucleotides or probes, that can be used to target one particular target nucleic acid over another target or non-target nucleic acid (i.e., specifically hybridized to a desired target nucleic acid), or to provide binding to the components of the SGC.

As described herein, embodiments of the invention include the use of target probe pairs that bind to the target nucleic acid. In the case where a pair of target probes binds to the same pre-amplifier (FIG. 1A), a probe configuration, sometimes referred to as a "Z" configuration, can be used. Such a configuration and its advantages for increasing sensitivity and decreasing background are described, for example, in U.S. Pat. No. 7,709,198, U.S. publications 2008/0038725 and 2009/0081688, and WO 2007/001986 and WO 2007/002006, each of which is incorporated herein by reference. U.S. Pat. No. 7,709,198 and U.S. publications 2008/0038725 and 2009/0081688 additionally describe details for selecting characteristics of the target probes, such as target probe pairs, including length, orientation, hybridization conditions, and the like. One skilled in the art can readily identify suitable configurations based on the teachings herein and, for example, in U.S. Pat. No. 7,709,198, U.S. publications 2008/0038725 and 2009/0081688, and WO 2007/001986 and WO 2007/002006.

As described herein, the target binding site of the target probes in a target probe pair can be in any desired orientation and combination. For example, the target binding site of one member of the target probe pair can be 5' or 3' to the pre-amplifier or pre-pre-amplifier binding site, and the other member of the pair can independently be oriented with the target binding site 5' or 3' to the pre-amplifier or pre-pre-amplifier binding site.

In another embodiment, the SGC used to detect the presence of a target nucleic acid is based on a collaborative hybridization of one or more components of the SGC (see US 20170101672 and WO 2017/066211, each of which is incorporated herein by reference). Such a collaborative hybridization is also referred to herein as BaseScope™. In a collaborative hybridization effect, the binding between two components of an SGC is mediated by two binding sites, and the melting temperature of the binding to the two sites simultaneously is higher than the melting temperature of the binding of one site alone (see US 20170101672 and WO 2017/066211). The collaborative hybridization effect can be enhanced by target probe set configurations as described in US 20170101672 and WO 2017/066211.

The methods of the invention, and related compositions, can utilize collaborative hybridization to increase specificity and to reduce background in in situ detection of nucleic acid targets, where a complex physiochemical environment and the presence of an overwhelming number of non-target molecules can generate high noise. Using such a collaborative hybridization method, the binding of label probes only occurs when the SGC is bound to the target nucleic acid. As described in US 20170101672 and WO 2017/066211 and illustrated in FIG. 1 thereof, the method can be readily modified to provide a desired signal to noise ratio by increasing the number of collaborative hybridizations in one or more components of the SGC.

In another embodiment, the collaborative hybridization can be applied to various components of the SGC. For example, the binding between components of an SGC can be a stable reaction, as described herein, or the binding can be configured to require a collaborative hybridization, also as described herein. In such a case, the binding component intended for collaborative hybridization are designed such that the component contains two segments that bind to another component.

Thus, the methods for detecting a target nucleic acid can utilize collaborative hybridization for the binding reactions between any one or all of the components in the detection system that provides an SGC specifically bound to a target nucleic acid. The number of components, and which components, to apply collaborative hybridization can be selected based on the desired assay conditions, the type of sample being assayed, a desired assay sensitivity, and so forth. Any one or combination of collaborative hybridization binding reactions can be used to increase the sensitivity and specificity of the assay. In embodiments of the invention, the collaborative hybridization can be between a pre-pre-amplifier and a pre-amplifier, between a pre-amplifier and an amplifier, between an amplifier and a label probe, or combinations thereof (see, for example, US 20170101672 and WO 2017/066211).

As disclosed herein, the components are generally bound directly to each other. In the case of nucleic acid containing components, the binding reaction is generally by hybridization. In the case of a hybridization reaction, the binding between the components is direct. If desired, an intermediary component can be included such that the binding of one component to another is indirect, for example, the intermediary component contains complementary binding sites to bridge two other components.

As disclosed herein, the steps of the methods of the invention, whereby components are assembled into an SGC bound to a target nucleic acid, can be performed concurrently or sequentially, in any order, so long as the target nucleic acid can be detected. In some cases, it can be desirable to reduce the number of assay steps, for example, reduce the number of hybridization and wash steps. One way of reducing the number of assay steps is to pre-assemble some or all components of the SGC prior to contacting with a cell. Such a pre-assembly can be performed by hybridizing some or all of the components of the SGC together prior to contacting the target nucleic acid. It is also possible to reduce the assay steps by pre-making some part of the SGC to integrate multiple components of the SGC through chemical synthesis, if desired.

It is understood that the invention can be carried out in any desired order, so long as the target nucleic acid is detected. Thus, in a method of the invention, the steps of contacting a cell with any components for assembly of an SGC can be performed in any desired order, can be carried out sequentially, or can be carried out simultaneously, or some steps can be performed sequentially while others are performed simultaneously, as desired, so long as the target nucleic acid is detected. It is further understood that embodiments disclosed herein can be independently combined with other embodiments disclosed herein, as desired, in order to utilize various configurations, component sizes, assay conditions, assay sensitivity, and the like.

It is understood that the invention can be carried out in any format that provides for the detection of a target nucleic acid. Although implementation of the invention has generally been described herein using in situ hybridization, it is understood that the invention can be carried out for detection of target nucleic acids in other formats, in particular for detection of target nucleic acids in a cell, as are well known in the art. One method that can be used for detecting target nucleic acids in a cell is flow cytometry, as is well known in the art (see, for example, Shapiro, *Practical Flow Cytometry* 3rd ed., Wiley-Liss, New York (1995); Ormerod, *Flow Cytometry,* 2nd ed., Springer (1999)). The methods, samples and kits of the invention can thus be used in an in situ hybridization assay format or another format, such as flow cytometry. The application of nucleic acid detection methods, including in situ hybridization, to flow cytometry has been described previously (see, for example, Hanley et al., *PLoS One,* 8(2):e57002. doi: 10.1371/journal.pone.0057002 (2013); Baxter et al., *Nature Protocols* 12(10):2029-2049 (2017)).

As described herein, the configuration of various components can be selected to provide a desired stable or collaborative hybridization binding reaction. It is understood that, even if a binding reaction is exemplified herein as a stable or unstable reaction, such as for a collaborative hybridization, any of the binding reactions can be modified, as desired, so long as the target nucleic acid is detected. It is further understood that the configuration can be varied and selected depending on the assay and hybridization conditions to be used. In general, if a binding reaction is desired to be stable, the segments of complementary nucleic acid sequence between the components is generally in the range of 10 to 50 nucleotides, or greater, for example, 16 to 30 nucleotides, such as 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides, or greater. If a binding reaction is desired to be relatively unstable, such as when a collaborative hybridization binding reaction is employed, the segments of complementary nucleic acid sequence between the components is generally in the range of 5 to 18 nucleotides, for example, 5, 6, 7, 8, 9, 10, 11, 12, 13, 14, 15, 16, 17 or 18 nucleotides. It is understood that the nucleotide lengths can be somewhat shorter or longer for a stable or unstable hybridization, depending on the conditions employed in the assay. It is further understood, as disclosed herein, that modified nucleotides such as LNA or BNA can be used to increase the binding strength at the modified base, thereby allowing length of the binding segment to be reduced. Thus, it is understood that, with respect to the length of nucleic acid segments that are complementary to other nucleic acid segments, the lengths described herein can be reduced further, if desired.

In some embodiments disclosed herein, a tier or layer of amplification molecules is extended by using base and extension amplification molecules, such as base and extension PPAs, base and extension PAs, and/or base and extension AMPs. In such embodiments, the build up of base and extension amplification molecules is also referred to herein as "tiles". The "tiles" can be used to extend the length of the layer of amplification molecules, as described herein. As used herein, the base amplification molecule is the molecule within a tier of molecules that binds to the lower tier, for example, a base PPA binds to a TP, a base PA binds to a PPA, and/or a base AMP binds to a PA, whereas an extension PPA binds to a base PPA and/or another extension PPA, an extension PA binds to a base PA and/or another extension PA, and/or an extension AMP binds to a base AMP and/or another extension AMP.

The length of each tile will depend on the number of repeats in each tile and the size of each repeating unit (i.e., PPA/PA/AMP binding segment repeats (BSRs)). The number of repeats can range from 2 to 20 repeats or even higher, as desired. For a PPA, the length of each tile will generally range from 56 to 560 bases, but it is understood that a shorter or longer sequence can be used, as desired, such as about 50 to about 600 bases, or any integer length in between. For the PA, the length of each tile will generally range from 50 to 500 but it is understood that a shorter or longer sequence can be used, as desired, such as about 35 to about 600 bases, or any integer length in between. For the AMP, the length of each tile will generally range from 36 to 360, but it is understood that a shorter or longer sequence can be used, as desired, such as about 25 to about 400 bases, or any integer length in between. The length of the binding segment repeats (BSRs) will generally range from 10-50 bases, for example, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 and 50. In a particular embodiment, the length of the PA-BSRs of the PPA is 28 bases. In a particular embodiment, the length of the AMP-BSRs of the PA is 25 bases. In a particular embodiment, the length of the LP-BSRs of the AMP is 18 bases.

With respect to a target probe pair, the target probe pair can be designed to bind to immediately adjacent segments of the target nucleic acid or on segments that have one to a number of bases between the target probe binding sites of the target probe pair. Generally, target probe pairs are designed for binding to the target nucleic acid such that there are generally between 0 to 500 bases between the binding sites on the target nucleic acid, for example, 0, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400, 420, 440, 460, 480, or 500 bases, or any integer length in between.

In some embodiments of the invention, the target probes are provided as a set that is specific for a target nucleic acid, where the set comprises two or more pairs of target probes that specifically hybridize to the same target nucleic acid. In such a case, the pairs of target probes in the target probe set specific for a target nucleic acid bind to different and non-overlapping sequences of the target nucleic acid. When a target probe set is used that has two or more pairs of target probes that can specifically hybridize to the same target nucleic acid, the molecule that binds to the target probe pairs, either a pre-amplifier (see FIG. 1A), or a pre-pre-amplifier (see FIGS. 1B and 1C), generally are the same for target probe pairs in the same target probe set. Thus, the target probe pairs that bind to the same target nucleic acid can be designed to comprise the same binding site for the molecule in the SGC that binds to the target probe pairs, that is, a pre-amplifier or pre-pre-amplifier. The use of multiple target probe pairs to detect a target nucleic acid provides for a higher signal associated with the assembly of multiple SGCs on the same target nucleic acid. In some embodiments, the number of target probe pairs used for binding to the same target nucleic acid are in the range of 1-10, 1-20, 1-30, 1-40, 1-50, 1-60, 1-70, 1-80, 1-90, 1-100, 1-110, 1-120, 1-130, 1-140, 1-150, 1-160, 1-170, 1-180, 1-190, or 1-200 pairs per target, or larger numbers of pairs, or any integer number of pairs in between, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, and the like.

The methods of the invention can be utilized to achieve the detection of desired target nucleic acids. In one embodiment, a target nucleic acid is detected with a plurality of target probe pairs. In such a case, target probe pairs are designed to bind to more than one region of a target nucleic acid to allow for the assembly of multiple SGCs onto a target nucleic acid. It is understood that the target binding sites of one target probe pair do not overlap with the target binding sites of another target probe pair if a plurality of target probe pairs are being used to bind to the same target nucleic acid.

In an embodiment of the invention, the target nucleic acids detected by the methods of the invention can be any target nucleic acid present in the cell sample. Thus, the target nucleic acids to be detected can be, but are not necessarily, the same type of nucleic acid. The target nucleic acids include but not limited to, RNA, including messenger RNA (mRNA), micro RNA (miRNA), ribosomal RNA (rRNA), mitochondrial RNA, non-coding RNA, and the like, or DNA, and the like, or DNA/RNA hybrids. In the case where the target nucleic acids are RNA, it is understood that the target nucleic acids can independently be selected from the group consisting of messenger RNA (mRNA), micro RNA (miRNA), ribosomal RNA (rRNA), mitochondrial RNA, and non-coding RNA. Thus, the target nucleic acids can independently be DNA, either single stranded or double stranded, or any type of RNA, either signal stranded or double stranded, or DNA/RNA hybrids.

In another embodiment, the methods of the invention can be applied to multiplex detection of target nucleic acids. In one embodiment, the methods of the invention are applied to the detection of two or more target nucleic acids, for example, 2, 3, 4, 5, 6, 7, 8, 9 or 10 or more target nucleic acids. The number of target nucleic acids that can be detected depends on the detection label. For fluorescent labels, up to 10 nucleic targets can generally be detected. For metal tagged probes using mass spectrometry-based detection, the number of target nucleic acids can be up to 150. A person skilled in the art can readily select suitable distinct labels to allow detection of more than one target nucleic acid in a sample.

In still another embodiment, the methods of the invention can be applied to simultaneous detection of double stranded nucleic acids and single stranded nucleic acids, for example, detection of DNA and RNA in the same sample. In such a case, probes can be designed to detect single stranded nucleic acids, such as RNA (see, for example, U.S. Pat. No. 7,709,198, U.S. publications 2008/0038725 and 2009/0081688, and 2017/0101672) and double stranded nucleic acids, such that both double stranded nucleic acids and single stranded nucleic acids, such as DNA and RNA, can be detected in the same sample.

The invention described herein generally relates to detection of nucleic acids in a sample. It is understood that the methods of the invention can additionally be applied to detecting target nucleic acids and optionally other molecules in the sample, in particular in the same cell as the target nucleic acid. For example, in addition to detecting target nucleic acids, proteins expressed in a cell can also concurrently be detected. Detection of proteins in a cell are well known to those skilled in the art, for example, by detecting the binding of protein-specific antibodies using any of the well known detection systems, including those described herein for detection of target nucleic acids. Detection of target nucleic acids and protein have been described (see, for example, Schulz et al., *Cell Syst.* 6(1):25-36 (2018)).

In situ detection methods can be used on tissue specimens immobilized on a glass slide, on single cells in suspension such as peripheral blood mononucleated cells (PBMCs) isolated from blood samples, and the like. Tissue specimens include, for example, tissue biopsy samples. Blood samples include, for example, blood samples taken for diagnostic purposes. In the case of a blood sample, the blood can be directly analyzed, such as in a blood smear, or the blood can be processed, for example, lysis of red blood cells, isolation of PBMCs or leukocytes, isolation of target cells, and the like, such that the cells in the sample analyzed by methods of the invention are in a blood sample or are derived from a blood sample. Similarly, a tissue specimen can be processed, for example, the tissue specimen minced and treated physically or enzymatically to disrupt the tissue into individual cells or cell clusters. Additionally, a cytological sample can be processed to isolate cells or disrupt cell clusters, if desired. Thus, the tissue, blood and cytological samples can be obtained and processed using methods well known in the art. The methods of the invention can be used in diagnostic applications to identify the presence or absence of pathological cells based on the presence or absence of a nucleic acid target that is a biomarker indicative of a pathology.

It is understood by those skilled in the art that any of a number of suitable samples can be used for detecting target nucleic acids using methods of the invention. The sample for use in methods of the invention will generally be a biological sample or tissue sample. Such a sample can be obtained from a biological subject, including a sample of biological tissue or fluid origin that is collected from an individual or some other source of biological material such as biopsy, autopsy or forensic materials. A biological sample also includes samples from a region of a biological subject containing or suspected of containing precancerous or cancer cells or tissues, for example, a tissue biopsy, including fine needle aspirates, blood sample, or cytological specimen. Such samples can be, but are not limited to, organs, tissues, tissue fractions and/or cells isolated from an organism such as a mammal. Exemplary biological samples include, but are not limited to, a cell culture, including a primary cell culture, a cell line, a tissue, an organ, an organelle, a biological fluid, and the like. Additional biological samples include but are not limited to a skin sample, tissue biopsies, including fine needle aspirates, cytological samples, stool, bodily fluids, including blood and/or serum samples, saliva, semen, and the like. Such samples can be used for medical or veterinary diagnostic purposes. A sample can also be obtained from other sources, for example, food, soil, surfaces of objects, and the like, and other materials for which detection of nucleic acids is desired. Thus, the methods of the invention can be used for detection of one or more pathogens, such as a DNA or RNA virus, a bacterium, a fungus, a single celled organism, such as a parasite, and the like, from a biological sample obtained from an individual or other sources.

Collection of cytological samples for analysis by methods of the invention are well known in the art (see, for example, Dey, "Cytology Sample Procurement, Fixation and Processing" in *Basic and Advanced Laboratory Techniques in Histopathology and Cytology* pp. 121-132, Springer, Singapore (2018); "Non-Gynocological Cytology Practice Guideline" American Society of Cytopathology, Adopted by the ASC executive board Mar. 2, 2004). Methods for processing samples for analysis of cervical tissue, including tissue biopsy and cytology samples, are well known in the art (see, for example, *Cecil Textbook of Medicine*, Bennett and Plum, eds., 20th ed., WB Saunders, Philadelphia (1996); *Colposcopy and Treatment of Cervical Intraepithelial Neoplasia: A Beginner's Manual*, Sellors and Sankaranarayanan, eds., International Agency for Research on Cancer, Lyon, France (2003); Kalaf and Cooper, *J. Clin. Pathol.* 60:449-455 (2007); Brown and Trimble, *Best Pract. Res. Clin. Obstet. Gynaecol.* 26:233-242 (2012); Waxman et al., *Obstet. Gynecol.* 120:1465-1471 (2012); *Cervical Cytology Practice Guidelines TOC*, Approved by the American Society of Cytopathology (ASC) Executive Board, Nov. 10, 2000)). In one embodiment, the cytological sample is a cervical sample, for example, a pap smear. In one embodiment, the sample is a fine needle aspirate.

In particular embodiments of the invention, the sample is a tissue specimen or is derived from a tissue specimen. In other particular embodiments of the invention, the sample is a blood sample or is derived from a blood sample. In still other particular embodiments of the invention, the sample is a cytological sample or is derived from a cytological sample.

The invention also provides a sample comprising a cell or a plurality of cells. The cell can optionally be fixed. The cells can optionally be permeabilized. Fixing and/or permeabilizing cells is particularly applicable to in situ assays. In one embodiment, the invention provides a sample of cells comprising an assembled SGC as described herein. The cells can optionally be fixed and/or permeabilized.

The invention additionally provides a slide comprising a cell or a plurality of cells. Optionally, the cell or cells are fixed to the slide. Optionally, the cell or cells are permeabilized. In particular embodiments, the cells on the slide are fixed and/or permeabilized for an in situ assay. In one embodiment, he invention provides a slide having immobilized thereon a plurality of cells comprising at least one cell containing a target nucleic acid and an assembled SGC as described above. The cells can optionally be fixed and/or permeabilized.

The invention also provides a kit comprising the components of an SGC, as described herein, where the kit does not include the target nucleic acid. Such a kit can comprise pre-amplifiers (PAs), amplifiers (AMPs) and label probes (LPs), and optionally pre-pre-amplifiers (PPAs), as disclosed herein. Optionally the kit can comprise target probes (TPs) directed to a particular target nucleic acids, or a plurality of target nucleic acids. The components of a kit of the invention can optionally be in a container, and optionally instructions for using the kit can be provided.

In one embodiment, the invention provides a kit comprising the components for assembling an SGC, wherein the kit comprises the PPAs, PAs, AMPs, and LPs of any one of SGCs described above or disclosed herein, including in any of FIGS. 2-6. In some embodiments, the kit further comprises the TPs for one or more target nucleic acids.

Embodiment 1. A composition comprising a Signal Generating Complex (SGC), wherein the composition comprises (A) a pair of target probes (TPs), wherein a first TP of the pair of TPs comprises a nucleic acid sequence comprising two segments, (i) a segment comprising a binding site for a first segment of a target nucleic acid, and (ii) a segment comprising a binding site for a first base pre-pre-amplifier (base PPA); and wherein a second TP of the pair of TPs comprises a nucleic acid sequence comprising two segments, (i) a segment comprising a binding site for a second segment of the target nucleic acid, and (ii) a segment comprising a binding site for a second base PPA; (B) a pair of base PPAs comprising the first and second base PPAs, wherein the first base PPA comprises a nucleic acid sequence comprising three segments, (i) a segment that binds to the first base PPA binding site of the first TP, (ii) a segment comprising a plurality of first pre-amplifier binding segment repeats (first PA-BSRs), and (iii) a segment comprising a binding site for a first extension pre-pre-amplifier (extension PPA); and wherein the second base PPA comprises a nucleic acid sequence comprising three segments, (i) a segment that binds to the second base PPA binding site of the second TP, (ii) a segment comprising a plurality of second pre-amplifier binding segment repeats (second PA-BSRs), and (iii) a segment comprising a binding site for a second extension PPA; wherein the first and second PA-BSRs are different sequences, and wherein the segments are in the order (i), (ii), (iii); (C) a set of extension PPAs comprising the first and second extension PPAs, wherein the first extension PPA comprises a nucleic acid sequence comprising two segments, (i) a segment that binds to the first extension PPA binding site of the first base PPA, and (ii) a segment comprising a plurality of the first PA-BSRs; and wherein the second extension PPA comprises a nucleic acid sequence comprising two segments, (i) a segment that binds to the second extension PPA binding site of the second base PPA, and (ii) a segment comprising a plurality of the second PA-BSRs; (D) a plurality of pre-amplifiers (PAs), wherein the PAs comprise a nucleic acid sequence comprising three segments, (i) a segment complementary to the first PA-BSR, (ii) a segment complementary to the second PA-BSR, and (iii) a segment comprising a plurality of amplifier binding segment repeats (AMP-BSRs); wherein the segments are in the order (i), (ii), (iii); (E) a plurality of amplifiers (AMPs), wherein the AMPs comprise a nucleic acid sequence comprising two segments, (i) a segment complementary to the AMP-BSRs, and (ii) a segment comprising a plurality of label probe binding segment repeats (LP-BSRs); and (F) a plurality of label probes (LPs), wherein the LPs comprise a nucleic acid sequence comprising two segments, (i) a segment complementary to the LP-BSRs, and (ii) a segment that is detectable; wherein the respective binding sites and complementary segments are hybridized to form the SGC.

Embodiment 2. The composition of embodiment 1, wherein the set of extension PPAs comprises at least one additional first extension PPA and at least one additional second extension PPA, wherein the additional first extension PPA comprises a nucleic acid sequence comprising two segments, (i) a segment comprising a binding site for the first extension PPA, and (ii) a segment comprising a plurality of the first PA-BSRs; wherein the additional second extension PPA comprises a nucleic acid sequence comprising two segments, (i) a segment comprising a binding site for the second extension PPA, and (ii) a segment comprising a plurality of the second PA-BSRs; and wherein the at least one additional first PPA optionally comprises a third segment (iii) comprising a second binding site for the first extension PPAs, and the at least one additional second PPA optionally comprises a third segment (iii) comprising a second binding site for the second extension PPAs, wherein the segments are in the order (i), (ii), (iii).

Embodiment 3. The composition of embodiment 1 or 2, wherein the binding sites between the first base PPA and the first extension PPA and/or between the extension PPAs comprise complementary sequences, and wherein the binding sites between the second base PPA and the second extension PPA and/or between the second extension PPAs comprise complementary sequences.

Embodiment 4. The composition of embodiment 1 or 2, wherein the composition further comprises a pair of bridges comprising a first bridge and second bridge, wherein the first bridge comprises two sections that bind to the first extension PPA binding site of the first base PPA and/or the first extension PPA binding site of the first extension PPA; and wherein the second bridge comprises two sections that bind to the second extension PPA binding site of the second base PPA and/or the second extension PPA binding site of the second extension PPA; wherein binding of the bridge tethers the extension PPA to the base PPA and/or the extension PPAs to each other.

Embodiment 5. The composition of embodiment 1 or 2, wherein the composition further comprises a pair of bridges comprising a first bridge and second bridge, wherein the first bridge comprises two sections, (i) a section that binds to the first extension PPA binding site of the first base PPA and/or the first extension PPA binding site of the first extension PPA, and (ii) a section that binds to the second extension PPA binding site of the second extension PPA; wherein the second bridge comprises two sections, (i) a section that binds to the second extension PPA binding site of the second base PPA and/or the second extension PPA binding site of the second extension PPA, and (ii) a section that binds to the first extension PPA binding site of the first extension PPA; wherein binding of the bridge tethers the second extension PPA to the first base PPA or the second extension PPA to the first extension PPA, and tethers the first extension PPA to the second base PPA or the first extension PPA to the second extension PPA.

Embodiment 6. The composition of embodiment 1 or 2, wherein the first base PPA and/or the first extension PPA comprises a fourth segment (iv) comprising a binding site for the second extension PPA, and wherein the second base PPA and/or the second extension PPA comprises a fourth segment (iv) comprising a binding site for the first extension PPA, wherein the segments of the PPA are in the order (i), (ii), (iv), (iii).

Embodiment 7. A composition comprising a Signal Generating Complex (SGC), wherein the composition comprises: (A) a pair of target probes (TPs), wherein a first TP of the pair of TPs comprises a nucleic acid sequence comprising two segments, (i) a segment comprising a binding site for a first segment of a target nucleic acid, and (ii) a segment comprising a binding site for a first pre-pre-amplifier (PPA); and wherein a second TP of the pair of TPs comprises a nucleic acid sequence comprising two segments, (i) a segment comprising a binding site for a second segment of the target nucleic acid, and (ii) a segment comprising a binding site for a second PPA; (B) a pair of PPAs comprising the first and second PPAs, wherein the first PPA comprises a nucleic acid sequence comprising two segments, (i) a segment that binds to the first PPA binding site of the first TP, and (ii) a segment comprising a plurality of first pre-amplifier binding segment repeats (first PA-BSRs); and wherein the second PPA comprises a nucleic acid sequence comprising two segments, (i) a segment that binds to the second PPA binding site of the second TP, and (ii) a segment comprising a plurality of second PA-BSRs, wherein the first and second PA-BSRs are different sequences; (C) a plurality of base pre-amplifiers (base PAs), wherein the base PAs comprise a nucleic acid sequence comprising four segments (i) a segment complementary to the first PA-BSRs, (ii) a segment complementary to the second PA-BSRs, (iii) a segment comprising a plurality of amplifier binding segment repeats (AMP-BSRs), and (iv) a segment that binds to an extension pre-amplifier (extension PA), wherein the segments are in the order (i), (ii), (iii), (iv); (D) a plurality of extension PAs, wherein the extension PAs comprise a nucleic acid sequence comprising two segments (i) a segment that binds to the extension PA binding site of the base PAs and (ii) a plurality of amplifier binding segment repeats (AMP-BSRs); and wherein the extension PAs optionally comprise a third segment (iii) comprising a binding site for the extension PAs, wherein the segments are in the order (i), (ii), (iii); (E) a plurality of amplifiers (AMPs), wherein the AMPS comprise a nucleic acid sequence comprising two segments, (i) a segment complementary to the AMP-BSRs, and (ii) a segment comprising a plurality of label probe binding segment repeats (LP-BSRs); and (F) a plurality of label probes (LPs), wherein the LPs comprise a nucleic acid sequence comprising two segments, (i) a segment complementary to the LP-BSRs, and (ii) a segment that is detectable; wherein the respective binding sites and complementary segments are hybridized to form the SGC.

Embodiment 8. The composition of embodiment 7, wherein the binding sites between the base PAs and the extension PAs comprise complementary sequences.

Embodiment 9. The composition of embodiment 7, wherein the composition further comprises a bridge, wherein the bridge comprises two sections that bind to the extension PA binding site of the base PA and/or the extension PA binding site of the extension PA, wherein binding of the bridge tethers the extension PA to the base PA and/or the extension PAs to each other.

Embodiment 10. A composition comprising a Signal Generating Complex (SGC), wherein the composition comprises: (A) a pair of target probes (TPs), wherein a first TP of the pair of TPs comprises a nucleic acid sequence comprising two segments, (i) a segment comprising a binding site for a first segment of a target nucleic acid, and (ii) a segment comprising a binding site for a first pre-pre-amplifier (PPA); and wherein a second TP of the pair of TPs comprises a nucleic acid sequence comprising two segments, (i) a segment comprising a binding site for a second segment of the target nucleic acid, and (ii) a segment comprising a binding site for a second PPA; (B) a pair of PPAs comprising the first and second PPAs, wherein the first PPA comprises a nucleic acid sequence comprising two segments, (i) a segment that binds to the first PPA binding site of the first TP, and (ii) a segment comprising a plurality of first pre-amplifier binding segment repeats (first PA-BSRs); and wherein the second PPA comprises a nucleic acid sequence comprising two segments, (i) a segment that binds to the second PPA binding site of the second TP, and (ii) a segment comprising a plurality of second PA-BSRs, wherein the first and second PA-BSRs are different sequences; (C) a plurality of pre-amplifiers (PAs), wherein the PAs comprise a nucleic acid sequence comprising three segments, (i) a segment complementary to the first PA-BSR, (ii) a segment complementary to the second PA-BSR, and (iii) a segment comprising a plurality of amplifier binding segment repeats (AMP-BSRs); wherein the segments are in the order (i), (ii), (iii); (D) a plurality of base amplifiers (base AMPs), wherein the base AMPs comprise a nucleic acid sequence comprising three segments (i) a segment complementary to the AMP-BSRs, (ii) a segment comprising a plurality of label probe binding segment repeats (LP-BSRs), and (iii) a segment that binds to an extension amplifier (extension AMP), in the order (i), (ii), (iii); (E) a plurality of extension AMPs, wherein the extension AMPs comprise a nucleic acid sequence comprising two segments (i) a segment that binds to the extension AMP binding site of the base AMP, and (ii) a segment comprising a plurality of label probe binding segment repeats (LP-BSRs); and wherein the extension AMPs optionally comprise a third segment (iii) comprising a binding site for the extension PAs, wherein the segments are in the order (i), (ii), (iii); (F) a plurality of label probes (LPs), wherein the LPs comprise a nucleic acid sequence comprising two segments (i) a segment complementary to the LP-BSRs, and (ii) a segment that is detectable; wherein the respective binding sites and complementary segments are hybridized to form the SGC.

Embodiment 11. The composition of embodiment 10, wherein the binding sites between the base AMPs and the extension AMPs comprise complementary sequences.

Embodiment 12. The composition of embodiment 10, wherein the composition further comprises a bridge, wherein the bridge comprises two sections that bind to the extension AMP binding site of the base AMP and/or the extension AMP binding site of the extension AMP, wherein binding of the bridge tethers the extension AMP to the base AMP and/or the extension AMPs to each other.

Embodiment 13. The composition of any one of embodiments 1-12: (I) wherein the first TP further comprises a third segment (iii) comprising a binding site for the second PPA; wherein the second TP further comprise a third segment (iii) comprising a binding site for the first PPA; and wherein the segments are in the order (i), (iii), (ii); and (II) wherein the first base PPA further comprises a fourth segment (iv) comprising a binding site for the second TP; wherein the second base PPA further comprises a fourth segment (iv) comprising a binding site for the first TP; wherein the segments are in the order (iv), (i), (ii), (iii); or wherein the first PPA further comprises a third segment (iii) comprising a binding site for the second TP; wherein the second PPA further comprises a third segment (iii) comprising a binding site for the first TP; wherein the segments are in the order (iii), (i), (ii).

Embodiment 14. A composition comprising a Signal Generating Complex (SGC), wherein the composition comprises: (A) a pair of target probes (TPs), wherein a first TP of the pair of TPs comprises a nucleic acid sequence comprising two segments, (i) a segment comprising a binding site for a first segment of a target nucleic acid, and (ii) a segment comprising a binding site for a first base pre-pre-amplifier (base PPA); and wherein a second TP of the pair of TPs comprises a nucleic acid sequence comprising two segments, (i) a segment comprising a binding site for a second segment of the target nucleic acid, and (ii) a segment comprising a binding site for a second base PPA; (B) a pair of PPAs comprising the first and second PPAs, wherein the first PPA comprises a nucleic acid sequence comprising two segments, (i) a segment that binds to the first PPA binding site of the first TP, and (ii) a segment comprising a plurality of first pre-amplifier binding segment repeats (first PA-BSRs), wherein the first PA-BSRs comprise two segments, (ia) a segment comprising a binding site for a first pre-amplifier (first PA) and (ib) a segment comprising a binding site for a second PA, wherein the segments of the first PPA are in the order (i), (ia), (ib); and wherein the second PPA comprises a nucleic acid sequence comprising two segments, (i) a segment that binds to the second PPA binding site of the second TP, and (ii) a segment comprising a plurality of second PA-BSRs, wherein the second PA-BSRs comprise two segments, (iia) a segment comprising a binding site for the second PA and (iib) a segment comprising a binding site for the first PA, wherein the segments of the second PPA are in the order (i), (iia), (iib); (C) a plurality of the first PAs and the second PAs, wherein the first PAs comprise a nucleic acid sequence comprising three segments, (i) a segment complementary to the second PA-BSR, (ii) a segment complementary to the first PA-BSR, and (iii) a segment comprising a plurality of amplifier binding segment repeats (AMP-BSRs); and wherein the second PAs comprise a nucleic acid sequence comprising three segments, (i) a segment complementary to the first PA-BSR, (ii) a segment complementary to the second PA-BSR, and (iii) a segment comprising a plurality of amplifier binding segment repeats (AMP-BSRs); (D) a plurality of amplifiers (AMPs), wherein the AMPs comprise a nucleic acid sequence comprising two segments, (i) a segment complementary to the AMP-BSRs, and (ii) a segment comprising a plurality of label probe binding segment repeats (LP-BSRs); and (E) a plurality of label probes (LPs), wherein the LPs comprise a nucleic acid sequence comprising two segments, (i) a segment complementary to the LP-BSRs, and (ii) a segment that is detectable; wherein the respective binding sites and complementary segments are hybridized to form the SGC.

Embodiment 15. The composition of embodiment 14, wherein the PPAs comprise base PPAs and extension PPAs.

Embodiment 16. The composition of embodiment 14, wherein the PAs comprise base PAs and extension PAs.

Embodiment 17. The composition of embodiment 14, wherein the AMPs comprise base AMPs and extension AMPs.

Embodiment 18. The composition of any one of embodiments 14-17, wherein the base and extension molecules are tethered by a configuration comprising wherein the binding sites between the first base PPA and the first extension PPA and/or between the first extension PPAs comprise complementary sequences, and wherein the binding sites between the second base PPA and the second extension PPA and/or between the second extension PPAs comprise complementary sequences; and/or wherein the binding sites between the base PA and extension PA, and or the binding sites between the base AMP and extension AMP comprise complementary sequences.

Embodiment 19. The composition of any one of embodiments 14-17, wherein the base and extension molecules are tethered by a configuration comprising wherein the composition further comprises a pair of bridges comprising a first bridge and second bridge, wherein the first bridge comprises two sections that bind to the first extension PPA binding site of the first base PPA and/or the first extension PPA binding site of the first extension PPA; and wherein the second bridge comprises two sections that bind to the second extension PPA binding site of the second base PPA and/or the second extension PPA binding site of the second extension PPA; wherein binding of the bridge tethers the extension PPA to the base PPA and/or the extension PPAs to each other; or wherein the composition further comprises a bridge, wherein the bridge comprises two sections that bind to the extension PA or AMP binding site of the base PA or AMP and/or the extension PA or AMP binding site of the extension PA or AMP, wherein binding of the bridge tethers the extension PA or AMP to the base PA or AMP and/or the extension PAs or AMPs to each other.

Embodiment 20. The composition of any one of embodiments 14-17, wherein the base and extension molecules are tethered by a configuration comprising wherein the composition further comprises a pair of bridges comprising a first bridge and second bridge, wherein the first bridge comprises two sections, (i) a section that binds to the first extension PPA binding site of the first base PPA and/or the first extension PPA binding site of the first extension PPA, and (ii) a section that binds to the second extension PPA binding site of the second extension PPA; wherein the second bridge comprises two sections, (i) a section that binds to the second extension PPA binding site of the second base PPA and/or the second extension PPA binding site of the second extension PPA, and (ii) a section that binds to the first extension PPA binding site of the first extension PPA; wherein binding of the bridge tethers the second extension PPA to the first base PPA or the second extension PPA to the first extension PPA, and tethers the first extension PPA to the second base PPA or the first extension PPA to the second extension PPA.

Embodiment 21. The composition of any one of embodiments 14-17, wherein the base and extension molecules are tethered by a configuration comprising wherein the first base PPA and/or the first extension PPA comprises a fourth segment (iv) comprising a binding site for the second extension PPA, and wherein the second base PPA and/or the second extension PPA comprises a fourth segment (iv) comprising a binding site for the first extension PPA, wherein the segments of the PPA are in the order (i), (ii), (iv), (iii).

Embodiment 22. The composition of any one of embodiments 14-21, (I) wherein the first TP further comprises a third segment (iii) comprising a binding site for the second PPA; wherein the second TP further comprise a third segment (iii) comprising a binding site for the first PPA; and wherein the segments are in the order (i), (iii), (ii); and (II) wherein the first base PPA further comprises a fourth segment (iv) comprising a binding site for the second TP; wherein the second base PPA further comprises a fourth segment (iv) comprising a binding site for the first TP; wherein the segments are in the order (iv), (i), (ii), (iii); or wherein the first PPA further comprises a third segment (iii) comprising a binding site for the second TP; wherein the second PPA further comprises a third segment (iii) comprising a binding site for the first TP; wherein the segments are in the order (iii), (i), (ii).

Embodiment 23. The composition of any one of embodiments 1-22, wherein the composition further comprises a second SGC, wherein the second SGC comprises a second target that is different from the target of embodiments 1-22, wherein the SGC comprises an SGC configuration of any one of embodiments 1-22 independently of the configuration of the first SGC, and wherein the second SGC is distinguishable from the first SGC.

Embodiment 24. The composition of embodiment 23, wherein the composition further comprises a third SGC, wherein the third SGC comprises a third target that is different from the target of embodiments 1-22 and the second target, wherein the SGC comprises an SGC configuration of any one of embodiments 1-22 independently of the configuration of the first SGC and/or the second SGC, and wherein the third SGC is distinguishable from the first and second SGC.

Embodiment 25. The composition of any one of embodiments 1-24, further comprising a target nucleic acid to which the pair of TPs bind.

Embodiment 26. The composition of any one of embodiments 1-25, further comprising a cell.

Embodiment 27. A method of detecting a target nucleic acid, comprising contacting a sample nucleic acid with the components for assembly of an SGC as in any one of embodiments 1-26, assembling an SGC on the target nucleic acid, and detecting the target nucleic acid.

Embodiment 28. The method of embodiment 27, wherein the nucleic acid is in a cell.

Embodiment 29. A kit comprising the components for assembling an SGC, wherein the kit comprises the PPAs, PAs, AMPS, and LPs of any one of embodiments 1-26.

Embodiment 30. The kit of embodiment 29, wherein the kit further comprises the TPs of any one of embodiments 1-26.

Embodiment 31. A sample of fixed and permeabilized cells comprising an assembled SGC of any one of embodiments 1-26.

Embodiment 32. A slide having immobilized thereon a plurality of fixed and permeabilized cells comprising at least one fixed and permeabilized cell containing a target nucleic acid and an assembled SGC of any one of embodiments 1-26.

Embodiment 33. A composition comprising a Signal Generating Complex (SGC), wherein the composition comprises: (A) a pair of target probes (TPs), wherein a first TP of the pair of TPs comprises a nucleic acid sequence comprising two segments, (i) a segment comprising a binding site for a first segment of a target nucleic acid, and (ii) a segment comprising a binding site for a first base pre-pre-amplifier (base PPA); and wherein a second TP of the pair of TPs comprises a nucleic acid sequence comprising two segments, (i) a segment comprising a binding site for a second segment of the target nucleic acid, and (ii) a segment comprising a binding site for a second base PPA; (B) a pair of base PPAs comprising the first and second base PPAs, wherein the first base PPA comprises a nucleic acid sequence comprising three segments, (i) a segment that binds to the first base PPA binding site of the first TP, (ii) a segment comprising a plurality of first pre-amplifier binding segment repeats (first PA-BSRs), and (iii) a segment comprising a binding site for a first extension pre-pre-amplifier (extension PPA); and wherein the second base PPA comprises a nucleic acid sequence comprising three segments, (i) a segment that binds to the second base PPA binding site of the second TP, (ii) a segment comprising a plurality of second pre-amplifier binding segment repeats (second PA-BSRs), and (iii) a segment comprising a binding site for a second extension PPA; wherein the first and second PA-BSRs are different sequences; (C) a set of extension PPAs comprising the first and second extension PPAs, wherein the first extension PPA comprises a nucleic acid sequence comprising two segments, (i) a segment that binds to the first extension PPA binding site of the first base PPA, and (ii) a segment comprising a plurality of the first PA-BSRs; and wherein the second extension PPA comprises a nucleic acid sequence comprising two segments, (i) a segment that binds to the second extension PPA binding site of the second base PPA, and (ii) a segment comprising a plurality of the second PA-BSRs; (D) a plurality of pre-amplifiers (PAs), wherein the PAs comprise a nucleic acid sequence comprising three segments, (i) a segment complementary to the first PA-BSR, (ii) a segment complementary to the second PA-BSR, and (iii) a segment comprising a plurality of amplifier binding segment repeats (AMP-BSRs); (E) a plurality of amplifiers (AMPs), wherein the AMPs comprise a nucleic acid sequence comprising two segments, (i) a segment complementary to the AMP-BSRs, and (ii) a segment comprising a plurality of label probe binding segment repeats (LP-BSRs); and (F) a plurality of label probes (LPs), wherein the LPs comprise a nucleic acid sequence comprising two segments, (i) a segment complementary to the LP-BSRs, and (ii) a segment that is detectable; wherein the respective binding sites and complementary segments are hybridized to form the SGC.

Embodiment 34. The composition of embodiment 33, wherein the set of extension PPAs comprises at least one additional first extension PPA and at least one additional second extension PPA, wherein the additional first extension PPA comprises a nucleic acid sequence comprising two segments, (i) a segment comprising a binding site for the first extension PPA, and (ii) a segment comprising a plurality of the first PA-BSRs; wherein the additional second extension PPA comprises a nucleic acid sequence comprising two segments, (i) a segment comprising a binding site for the second extension PPA, and (ii) a segment comprising a plurality of the second PA-BSRs; and wherein the at least one additional first PPA optionally comprises a third segment (iii) comprising a second binding site for the first extension PPAs, and the at least one additional second PPA optionally comprises a third segment (iii) comprising a second binding site for the second extension PPAs.

Embodiment 35. The composition of embodiment 33 or 34, wherein the binding sites between the first base PPA and the first extension PPA and/or between the extension PPAs comprise complementary sequences, and wherein the binding sites between the second base PPA and the second extension PPA and/or between the second extension PPAs comprise complementary sequences.

Embodiment 36. The composition of embodiment 33 or 34, wherein the composition further comprises a pair of bridges comprising a first bridge and second bridge, wherein the first bridge comprises two sections that bind to the first extension PPA binding site of the first base PPA and/or the first extension PPA binding site of the first extension PPA; and wherein the second bridge comprises two sections that bind to the second extension PPA binding site of the second base PPA and/or the second extension PPA binding site of the second extension PPA; wherein binding of the bridge tethers the extension PPA to the base PPA and/or the extension PPAs to each other.

Embodiment 37. The composition of embodiment 33 or 34, wherein the composition further comprises a pair of bridges comprising a first bridge and second bridge, wherein the first bridge comprises two sections, (i) a section that binds to the first extension PPA binding site of the first base PPA and/or the first extension PPA binding site of the first extension PPA, and (ii) a section that binds to the second extension PPA binding site of the second extension PPA; wherein the second bridge comprises two sections, (i) a section that binds to the second extension PPA binding site of the second base PPA and/or the second extension PPA binding site of the second extension PPA, and (ii) a section that binds to the first extension PPA binding site of the first extension PPA; wherein binding of the bridge tethers the second extension PPA to the first base PPA or the second extension PPA to the first extension PPA, and tethers the first extension PPA to the second base PPA or the first extension PPA to the second extension PPA.

Embodiment 38. The composition of embodiment 33 or 34, wherein the first base PPA and/or the first extension PPA comprises a fourth segment (iv) comprising a binding site for the second extension PPA, and wherein the second base PPA and/or the second extension PPA comprises a fourth segment (iv) comprising a binding site for the first extension PPA.

Embodiment 39. A composition comprising a Signal Generating Complex (SGC), wherein the composition comprises: (A) a pair of target probes (TPs), wherein a first TP of the pair of TPs comprises a nucleic acid sequence comprising two segments, (i) a segment comprising a binding site for a first segment of a target nucleic acid, and (ii) a segment comprising a binding site for a first pre-pre-amplifier (PPA); and wherein a second TP of the pair of TPs comprises a nucleic acid sequence comprising two segments, (i) a segment comprising a binding site for a second segment of the target nucleic acid, and (ii) a segment comprising a binding site for a second PPA; (B) a pair of PPAs comprising the first and second PPAs, wherein the first PPA comprises a nucleic acid sequence comprising two segments, (i) a segment that binds to the first PPA binding site of the first TP, and (ii) a segment comprising a plurality of first pre-amplifier binding segment repeats (first PA-BSRs); and wherein the second PPA comprises a nucleic acid sequence comprising two segments, (i) a segment that binds to the second PPA binding site of the second TP, and (ii) a segment comprising a plurality of second PA-BSRs, wherein the first and second PA-BSRs are different sequences; (C) a plurality of base pre-amplifiers (base PAs), wherein the base PAs comprise a nucleic acid sequence comprising four segments (i) a segment complementary to the first PA-BSRs, (ii) a segment complementary to the second PA-BSRs, (iii) a segment comprising a plurality of amplifier binding segment repeats (AMP-BSRs), and (iv) a segment that binds to an extension pre-amplifier (extension PA); (D) a plurality of extension PAs, wherein the extension PAs comprise a nucleic acid sequence comprising two segments (i) a segment that binds to the extension PA binding site of the base PAs and (ii) a plurality of amplifier binding segment repeats (AMP-BSRs); and wherein the extension PAs optionally comprise a third segment (iii) comprising a binding site for the extension PAs; (E) a plurality of amplifiers (AMPs), wherein the AMPS comprise a nucleic acid sequence comprising two segments, (i) a segment complementary to the AMP-BSRs, and (ii) a segment comprising a plurality of label probe binding segment repeats (LP-BSRs); and (F) a plurality of label probes (LPs), wherein the LPs comprise a nucleic acid sequence comprising two segments, (i) a segment complementary to the LP-BSRs, and (ii) a segment that is detectable; wherein the respective binding sites and complementary segments are hybridized to form the SGC.

Embodiment 40. The composition of embodiment 39, wherein the binding sites between the base PAs and the extension PAs comprise complementary sequences.

Embodiment 41. The composition of embodiment 39, wherein the composition further comprises a bridge, wherein the bridge comprises two sections that bind to the extension PA binding site of the base PA and/or the extension PA binding site of the extension PA, wherein binding of the bridge tethers the extension PA to the base PA and/or the extension PAs to each other.

Embodiment 42. A composition comprising a Signal Generating Complex (SGC), wherein the composition comprises: (A) a pair of target probes (TPs), wherein a first TP of the pair of TPs comprises a nucleic acid sequence comprising two segments, (i) a segment comprising a binding site for a first segment of a target nucleic acid, and (ii) a segment comprising a binding site for a first pre-pre-amplifier (PPA); and wherein a second TP of the pair of TPs comprises a nucleic acid sequence comprising two segments, (i) a segment comprising a binding site for a second segment of the target nucleic acid, and (ii) a segment comprising a binding site for a second PPA; (B) a pair of PPAs comprising the first and second PPAs, wherein the first PPA comprises a nucleic acid sequence comprising two segments, (i) a segment that binds to the first PPA binding site of the first TP, and (ii) a segment comprising a plurality of first pre-amplifier binding segment repeats (first PA-BSRs); and wherein the second PPA comprises a nucleic acid sequence comprising two segments, (i) a segment that binds to the second PPA binding site of the second TP, and (ii) a segment comprising a plurality of second PA-BSRs, wherein the first and second PA-BSRs are different sequences; (C) a plurality of pre-amplifiers (PAs), wherein the PAs comprise a nucleic acid sequence comprising three segments, (i) a segment complementary to the first PA-BSR, (ii) a segment complementary to the second PA-BSR, and (iii) a segment comprising a plurality of amplifier binding segment repeats (AMP-BSRs); (D) a plurality of base amplifiers (base AMPs), wherein the base AMPs comprise a nucleic acid sequence comprising three segments (i) a segment complementary to the AMP-BSRs, (ii) a segment comprising a plurality of label probe binding segment repeats (LP-BSRs), and (iii) a segment that binds to an extension amplifier (extension AMP); (E) a plurality of extension AMPs, wherein the extension AMPs comprise a nucleic acid sequence comprising two segments (i) a segment that binds to the extension AMP binding site of the base AMP, and (ii) a segment comprising a plurality of label probe binding segment repeats (LP-BSRs); and wherein the extension AMPs optionally comprise a third segment (iii) comprising a binding site for the extension PAs; (F) a plurality of label probes (LPs), wherein the LPs comprise a nucleic acid sequence comprising two segments (i) a segment complementary to the LP-BSRs, and (ii) a segment that is detectable; wherein the respective binding sites and complementary segments are hybridized to form the SGC.

Embodiment 43. The composition of embodiment 42, wherein the binding sites between the base AMPs and the extension AMPs comprise complementary sequences.

Embodiment 44. The composition of embodiment 42, wherein the composition further comprises a bridge, wherein the bridge comprises two sections that bind to the extension AMP binding site of the base AMP and/or the extension AMP binding site of the extension AMP, wherein binding of the bridge tethers the extension AMP to the base AMP and/or the extension AMPs to each other.

Embodiment 45. The composition of any one of embodiments 33-44: (I) wherein the first TP further comprises a third segment (iii) comprising a binding site for the second PPA; wherein the second TP further comprise a third segment (iii) comprising a binding site for the first PPA; and (II) wherein the first base PPA further comprises a fourth segment (iv) comprising a binding site for the second TP; wherein the second base PPA further comprises a fourth segment (iv) comprising a binding site for the first TP; or wherein the first PPA further comprises a third segment (iii) comprising a binding site for the second TP; wherein the second PPA further comprises a third segment (iii) comprising a binding site for the first TP.

Embodiment 46. A composition comprising a Signal Generating Complex (SGC), wherein the composition comprises: (A) a pair of target probes (TPs), wherein a first TP of the pair of TPs comprises a nucleic acid sequence comprising two segments, (i) a segment comprising a binding site for a first segment of a target nucleic acid, and (ii) a segment comprising a binding site for a first base pre-pre-amplifier (base PPA); and wherein a second TP of the pair of TPs comprises a nucleic acid sequence comprising two segments, (i) a segment comprising a binding site for a second segment of the target nucleic acid, and (ii) a segment comprising a binding site for a second base PPA; (B) a pair of PPAs comprising the first and second PPAs, wherein the first PPA comprises a nucleic acid sequence comprising two segments, (i) a segment that binds to the first PPA binding site of the first TP, and (ii) a segment comprising a plurality of first pre-amplifier binding segment repeats (first PA-BSRs), wherein the first PA-BSRs comprise two segments, (ia) a segment comprising a binding site for a first pre-amplifier (first PA) and (ib) a segment comprising a binding site for a second PA; and wherein the second PPA comprises a nucleic acid sequence comprising two segments, (i) a segment that binds to the second PPA binding site of the second TP, and (ii) a segment comprising a plurality of second PA-BSRs, wherein the second PA-BSRs comprise two segments, (iia) a segment comprising a binding site for the second PA and (iib) a segment comprising a binding site for the first PA; (C) a plurality of the first PAs and the second PAs, wherein the first PAs comprise a nucleic acid sequence comprising three segments, (i) a segment complementary to the second PA-BSR, (ii) a segment complementary to the first PA-BSR, and (iii) a segment comprising a plurality of amplifier binding segment repeats (AMP-BSRs); and wherein the second PAs comprise a nucleic acid sequence comprising three segments, (i) a segment complementary to the first PA-BSR, (ii) a segment complementary to the second PA-BSR, and (iii) a segment comprising a plurality of amplifier binding segment repeats (AMP-BSRs); (D) a plurality of amplifiers (AMPs), wherein the AMPs comprise a nucleic acid sequence comprising two segments, (i) a segment complementary to the AMP-BSRs, and (ii) a segment comprising a plurality of label probe binding segment repeats (LP-BSRs); and (E) a plurality of label probes (LPs), wherein the LPs comprise a nucleic acid sequence comprising two segments, (i) a segment complementary to the LP-BSRs, and (ii) a segment that is detectable; wherein the respective binding sites and complementary segments are hybridized to form the SGC.

Embodiment 47. The composition of embodiment 46, wherein the PPAs comprise base PPAs and extension PPAs.

Embodiment 48. The composition of embodiment 46, wherein the PAs comprise base PAs and extension PAs.

Embodiment 49. The composition of embodiment 46, wherein the AMPs comprise base AMPs and extension AMPs.

Embodiment 50. The composition of any one of embodiments 46-49, wherein the base and extension molecules are tethered by a configuration comprising: wherein the binding sites between the first base PPA and the first extension PPA and/or between the first extension PPAs comprise complementary sequences, and wherein the binding sites between the second base PPA and the second extension PPA and/or between the second extension PPAs comprise complementary sequences; and/or wherein the binding sites between the base PA and extension PA, and or the binding sites between the base AMP and extension AMP comprise complementary sequences.

Embodiment 51. The composition of any one of embodiments 46-49, wherein the base and extension molecules are tethered by a configuration comprising: wherein the composition further comprises a pair of bridges comprising a first bridge and second bridge, wherein the first bridge comprises two sections that bind to the first extension PPA binding site of the first base PPA and/or the first extension PPA binding site of the first extension PPA; and wherein the second bridge comprises two sections that bind to the second extension PPA binding site of the second base PPA and/or the second extension PPA binding site of the second extension PPA; wherein binding of the bridge tethers the extension PPA to the base PPA and/or the extension PPAs to each other; or wherein the composition further comprises a bridge, wherein the bridge comprises two sections that bind to the extension PA or AMP binding site of the base PA or AMP and/or the extension PA or AMP binding site of the extension PA or AMP, wherein binding of the bridge tethers the extension PA or AMP to the base PA or AMP and/or the extension PAs or AMPs to each other.

Embodiment 52. The composition of any one of embodiments 46-49, wherein the base and extension molecules are tethered by a configuration comprising: wherein the composition further comprises a pair of bridges comprising a first bridge and second bridge, wherein the first bridge comprises two sections, (i) a section that binds to the first extension PPA binding site of the first base PPA and/or the first extension PPA binding site of the first extension PPA, and (ii) a section that binds to the second extension PPA binding site of the second extension PPA; wherein the second bridge comprises two sections, (i) a section that binds to the second extension PPA binding site of the second base PPA and/or the second extension PPA binding site of the second extension PPA, and (ii) a section that binds to the first extension PPA binding site of the first extension PPA; wherein binding of the bridge tethers the second extension PPA to the first base PPA or the second extension PPA to the first extension PPA, and tethers the first extension PPA to the second base PPA or the first extension PPA to the second extension PPA.

Embodiment 53. The composition of any one of embodiments 46-49, wherein the base and extension molecules are tethered by a configuration comprising: wherein the first base PPA and/or the first extension PPA comprises a fourth segment (iv) comprising a binding site for the second extension PPA, and wherein the second base PPA and/or the second extension PPA comprises a fourth segment (iv) comprising a binding site for the first extension PPA.

Embodiment 54. The composition of any one of embodiments 46-53: (I) wherein the first TP further comprises a third segment (iii) comprising a binding site for the second PPA; wherein the second TP further comprise a third segment (iii) comprising a binding site for the first PPA; and (II) wherein the first base PPA further comprises a fourth segment (iv) comprising a binding site for the second TP; wherein the second base PPA further comprises a fourth segment (iv) comprising a binding site for the first TP; or wherein the first PPA further comprises a third segment (iii) comprising a binding site for the second TP; wherein the second PPA further comprises a third segment (iii) comprising a binding site for the first TP.

Embodiment 55. The composition of any one of embodiments 33-54, wherein the composition further comprises a second SGC, wherein the second SGC comprises a second target that is different from the target of embodiments 33-54, wherein the SGC comprises an SGC configuration of any one of embodiments 33-54 independently of the configuration of the first SGC, and wherein the second SGC is distinguishable from the first SGC.

Embodiment 56. The composition of embodiment 55, wherein the composition further comprises a third SGC, wherein the third SGC comprises a third target that is different from the target of embodiments 33-54 and the second target, wherein the SGC comprises an SGC configuration of any one of embodiments 33-54 independently of the configuration of the first SGC and/or the second SGC, and wherein the third SGC is distinguishable from the first and second SGC.

Embodiment 57. The composition of any one of embodiments 33-56, further comprising a target nucleic acid to which the pair of TPs bind.

Embodiment 58. The composition of any one of embodiments 33-57, further comprising a cell.

Embodiment 59. A method of detecting a target nucleic acid, comprising contacting a sample nucleic acid with the components for assembly of an SGC as in any one of embodiments 33-58, assembling an SGC on the target nucleic acid, and detecting the target nucleic acid.

Embodiment 60. The method of embodiment 59, wherein the nucleic acid is in a cell.

Embodiment 61. A kit comprising the components for assembling an SGC, wherein the kit comprises the PPAs, PAs, AMPs, and LPs of any one of embodiments 33-58.

Embodiment 62. The kit of embodiment 61, wherein the kit further comprises the TPs of any one of embodiments 33-58.

Embodiment 63. A sample of fixed and permeabilized cells comprising an assembled SGC of any one of embodiments 33-58.

Embodiment 64. A slide having immobilized thereon a plurality of fixed and permeabilized cells comprising at least one fixed and permeabilized cell containing a target nucleic acid and an assembled SGC of any one of embodiments 33-58.

Embodiment 65. A method of detecting a target nucleic acid, comprising (A) contacting a sample comprising a target nucleic acid with a pair of target probes (TPs), wherein a first TP of the pair of TPs comprises a nucleic acid sequence comprising two segments, (i) a segment comprising a binding site for a first segment of a target nucleic acid, and (ii) a segment comprising a binding site for a first base pre-pre-amplifier (base PPA); and wherein a second TP of the pair of TPs comprises a nucleic acid sequence comprising two segments, (i) a segment comprising a binding site for a second segment of the target nucleic acid, and (ii) a segment comprising a binding site for a second base PPA; (B) contacting the sample with a pair of base PPAs comprising the first and second base PPAs, wherein the first base PPA comprises a nucleic acid sequence comprising three segments, (i) a segment that binds to the first base PPA binding site of the first TP, (ii) a segment comprising a plurality of first pre-amplifier binding segment repeats (first PA-BSRs), and (iii) a segment comprising a binding site for a first extension pre-pre-amplifier (extension PPA); and wherein the second base PPA comprises a nucleic acid sequence comprising three segments, (i) a segment that binds to the second base PPA binding site of the second TP, (ii) a segment comprising a plurality of second pre-amplifier binding segment repeats (second PA-BSRs), and (iii) a segment comprising a binding site for a second extension PPA; wherein the first and second PA-BSRs are different sequences, and wherein the segments are in the order (i), (ii), (iii); (C) contacting the sample with a set of extension PPAs comprising the first and second extension PPAs, wherein the first extension PPA comprises a nucleic acid sequence comprising two segments, (i) a segment that binds to the first extension PPA binding site of the first base PPA, and (ii) a segment comprising a plurality of the first PA-BSRs; and wherein the second extension PPA comprises a nucleic acid sequence comprising two segments, (i) a segment that binds to the second extension PPA binding site of the second base PPA, and (ii) a segment comprising a plurality of the second PA-BSRs; (D) contacting the sample with a plurality of pre-amplifiers (PAs), wherein the PAs comprise a nucleic acid sequence comprising three segments, (i) a segment complementary to the first PA-BSR, (ii) a segment complementary to the second PA-BSR, and (iii) a segment comprising a plurality of amplifier binding segment repeats (AMP-BSRs); wherein the segments are in the order (i), (ii), (iii); (E) contacting the sample with a plurality of amplifiers (AMPs), wherein the AMPs comprise a nucleic acid sequence comprising two segments, (i) a segment complementary to the AMP-BSRs, and (ii) a segment comprising a plurality of label probe binding segment repeats (LP-BSRs); and (F) contacting the sample with a plurality of label probes (LPs), wherein the LPs comprise a nucleic acid sequence comprising two segments, (i) a segment complementary to the LP-BSRs, and (ii) a segment that is detectable; wherein the respective binding sites and complementary segments are hybridized to form a Signal Generating Complex (SGC), thereby detecting the target nucleic acid.

66. The method of embodiment 65, wherein the set of extension PPAs comprises at least one additional first extension PPA and at least one additional second extension PPA, wherein the additional first extension PPA comprises a nucleic acid sequence comprising two segments, (i) a segment comprising a binding site for the first extension PPA, and (ii) a segment comprising a plurality of the first PA-BSRs; wherein the additional second extension PPA comprises a nucleic acid sequence comprising two segments, (i) a segment comprising a binding site for the second extension PPA, and (ii) a segment comprising a plurality of the second PA-BSRs; and wherein the at least one additional first PPA optionally comprises a third segment (iii) comprising a second binding site for the first extension PPAs, and the at least one additional second PPA optionally comprises a third segment (iii) comprising a second binding site for the second extension PPAs, wherein the segments are in the order (i), (ii), (iii).

Embodiment 67. The method of embodiment 65 or 66, wherein the binding sites between the first base PPA and the first extension PPA and/or between the extension PPAs comprise complementary sequences, and wherein the binding sites between the second base PPA and the second extension PPA and/or between the second extension PPAs comprise complementary sequences.

Embodiment 68. The method of embodiment 65 or 66, wherein the composition further comprises a pair of bridges comprising a first bridge and second bridge, wherein the first bridge comprises two sections that bind to the first extension PPA binding site of the first base PPA and/or the first extension PPA binding site of the first extension PPA; and wherein the second bridge comprises two sections that bind to the second extension PPA binding site of the second base PPA and/or the second extension PPA binding site of the second extension PPA; wherein binding of the bridge tethers the extension PPA to the base PPA and/or the extension PPAs to each other.

Embodiment 69. The method of embodiment 65 or 66, wherein the composition further comprises a pair of bridges comprising a first bridge and second bridge, wherein the first bridge comprises two sections, (i) a section that binds to the first extension PPA binding site of the first base PPA and/or the first extension PPA binding site of the first extension PPA, and (ii) a section that binds to the second extension PPA binding site of the second extension PPA; wherein the second bridge comprises two sections, (i) a section that binds to the second extension PPA binding site of the second base PPA and/or the second extension PPA binding site of the second extension PPA, and (ii) a section that binds to the first extension PPA binding site of the first extension PPA; wherein binding of the bridge tethers the second extension PPA to the first base PPA or the second extension PPA to the first extension PPA, and tethers the first extension PPA to the second base PPA or the first extension PPA to the second extension PPA.

Embodiment 70. The method of embodiment 65 or 66, wherein the first base PPA and/or the first extension PPA comprises a fourth segment (iv) comprising a binding site for the second extension PPA, and wherein the second base PPA and/or the second extension PPA comprises a fourth segment (iv) comprising a binding site for the first extension PPA, wherein the segments of the PPA are in the order (i), (ii), (iv), (iii).

Embodiment 71. A method of detecting a target nucleic acid, comprising (A) contacting a sample comprising a target nucleic acid with a pair of target probes (TPs), wherein a first TP of the pair of TPs comprises a nucleic acid sequence comprising two segments, (i) a segment comprising a binding site for a first segment of a target nucleic acid, and (ii) a segment comprising a binding site for a first pre-pre-amplifier (PPA); and wherein a second TP of the pair of TPs comprises a nucleic acid sequence comprising two segments, (i) a segment comprising a binding site for a second segment of the target nucleic acid, and (ii) a segment comprising a binding site for a second PPA; (B) contacting the sample with a pair of PPAs comprising the first and second PPAs, wherein the first PPA comprises a nucleic acid sequence comprising two segments, (i) a segment that binds to the first PPA binding site of the first TP, and (ii) a segment comprising a plurality of first pre-amplifier binding segment repeats (first PA-BSRs); and wherein the second PPA comprises a nucleic acid sequence comprising two segments, (i) a segment that binds to the second PPA binding site of the second TP, and (ii) a segment comprising a plurality of second PA-BSRs, wherein the first and second PA-BSRs are different sequences; (C) contacting the sample with a plurality of base pre-amplifiers (base PAs), wherein the base PAs comprise a nucleic acid sequence comprising four segments (i) a segment complementary to the first PA-BSRs, (ii) a segment complementary to the second PA-BSRs, (iii) a segment comprising a plurality of amplifier binding segment repeats (AMP-BSRs), and (iv) a segment that binds to an extension pre-amplifier (extension PA), wherein the segments are in the order (i), (ii), (iii), (iv); (D) contacting the sample with a plurality of extension PAs, wherein the extension PAs comprise a nucleic acid sequence comprising two segments (i) a segment that binds to the extension PA binding site of the base PAs and (ii) a plurality of amplifier binding segment repeats (AMP-BSRs); and wherein the extension PAs optionally comprise a third segment (iii) comprising a binding site for the extension PAs, wherein the segments are in the order (i), (ii), (iii); (E) contacting the sample with a plurality of amplifiers (AMPs), wherein the AMPS comprise a nucleic acid sequence comprising two segments, (i) a segment complementary to the AMP-BSRs, and (ii) a segment comprising a plurality of label probe binding segment repeats (LP-BSRs); and (F) contacting the sample with a plurality of label probes (LPs), wherein the LPs comprise a nucleic acid sequence comprising two segments, (i) a segment complementary to the LP-BSRs, and (ii) a segment that is detectable; wherein the respective binding sites and complementary segments are hybridized to form a Signal Generating Complex (SGC), thereby detecting the target nucleic acid.

Embodiment 72. The method of embodiment 71, wherein the binding sites between the base PAs and the extension PAs comprise complementary sequences.

Embodiment 73. The method of embodiment 71, wherein the composition further comprises a bridge, wherein the bridge comprises two sections that bind to the extension PA binding site of the base PA and/or the extension PA binding site of the extension PA, wherein binding of the bridge tethers the extension PA to the base PA and/or the extension PAs to each other.

Embodiment 74. A method of detecting a target nucleic acid, comprising (A) contacting a sample comprising a target nucleic acid with a pair of target probes (TPs), wherein a first TP of the pair of TPs comprises a nucleic acid sequence comprising two segments, (i) a segment comprising a binding site for a first segment of a target nucleic acid, and (ii) a segment comprising a binding site for a first pre-pre-amplifier (PPA); and wherein a second TP of the pair of TPs comprises a nucleic acid sequence comprising two segments, (i) a segment comprising a binding site for a second segment of the target nucleic acid, and (ii) a segment comprising a binding site for a second PPA; (B) contacting the sample with a pair of PPAs comprising the first and second PPAs, wherein the first PPA comprises a nucleic acid sequence comprising two segments, (i) a segment that binds to the first PPA binding site of the first TP, and (ii) a segment comprising a plurality of first pre-amplifier binding segment repeats (first PA-BSRs); and wherein the second PPA comprises a nucleic acid sequence comprising two segments, (i) a segment that binds to the second PPA binding site of the second TP, and (ii) a segment comprising a plurality of second PA-BSRs, wherein the first and second PA-BSRs are different sequences; (C) contacting the sample with a plurality of pre-amplifiers (PAs), wherein the PAs comprise a nucleic acid sequence comprising three segments, (i) a segment complementary to the first PA-BSR, (ii) a segment complementary to the second PA-BSR, and (iii) a segment comprising a plurality of amplifier binding segment repeats (AMP-BSRs); wherein the segments are in the order (i), (ii), (iii); (D) contacting the sample with a plurality of base amplifiers (base AMPs), wherein the base AMPs comprise a nucleic acid sequence comprising three segments (i) a segment complementary to the AMP-BSRs, (ii) a segment comprising a plurality of label probe binding segment repeats (LP-BSRs), and (iii) a segment that binds to an extension amplifier (extension AMP), in the order (i), (ii), (iii); (E) contacting the sample with a plurality of extension AMPs, wherein the extension AMPs comprise a nucleic acid sequence comprising two segments (i) a segment that binds to the extension AMP binding site of the base AMP, and (ii) a segment comprising a plurality of label probe binding segment repeats (LP-BSRs); and wherein the extension AMPs optionally comprise a third segment (iii) comprising a binding site for the extension PAs, wherein the segments are in the order (i), (ii), (iii); (F) contacting the sample with a plurality of label probes (LPs), wherein the LPs comprise a nucleic acid sequence comprising two segments (i) a segment complementary to the LP-BSRs, and (ii) a segment that is detectable; wherein the respective binding sites and complementary segments are hybridized to form a Signal Generating Complex (SGC), thereby detecting the target nucleic acid.

Embodiment 75. The method of embodiment 74, wherein the binding sites between the base AMPs and the extension AMPs comprise complementary sequences.

Embodiment 76. The method of embodiment 74, wherein the composition further comprises a bridge, wherein the bridge comprises two sections that bind to the extension AMP binding site of the base AMP and/or the extension AMP binding site of the extension AMP, wherein binding of the bridge tethers the extension AMP to the base AMP and/or the extension AMPs to each other.

Embodiment 77. The method of any one of embodiments 65-76, (I) wherein the first TP further comprises a third segment (iii) comprising a binding site for the second PPA; wherein the second TP further comprise a third segment (iii) comprising a binding site for the first PPA; and wherein the segments are in the order (i), (iii), (ii); and (II) wherein the first base PPA further comprises a fourth segment (iv) comprising a binding site for the second TP; wherein the second base PPA further comprises a fourth segment (iv) comprising a binding site for the first TP; wherein the segments are in the order (iv), (i), (ii), (iii); or wherein the first PPA further comprises a third segment (iii) comprising a binding site for the second TP; wherein the second PPA further comprises a third segment (iii) comprising a binding site for the first TP; wherein the segments are in the order (iii), (i), (ii).

Embodiment 78. A method of detecting a target nucleic acid, comprising (A) contacting a sample comprising a target nucleic acid with a pair of target probes (TPs), wherein a first TP of the pair of TPs comprises a nucleic acid sequence comprising two segments, (i) a segment comprising a binding site for a first segment of a target nucleic acid, and (ii) a segment comprising a binding site for a first base pre-pre-amplifier (base PPA); and wherein a second TP of the pair of TPs comprises a nucleic acid sequence comprising two segments, (i) a segment comprising a binding site for a second segment of the target nucleic acid, and (ii) a segment comprising a binding site for a second base PPA; (B) contacting the sample with a pair of PPAs comprising the first and second PPAs, wherein the first PPA comprises a nucleic acid sequence comprising two segments, (i) a segment that binds to the first PPA binding site of the first TP, and (ii) a segment comprising a plurality of first pre-amplifier binding segment repeats (first PA-BSRs), wherein the first PA-BSRs comprise two segments, (ia) a segment comprising a binding site for a first pre-amplifier (first PA) and (ib) a segment comprising a binding site for a second PA, wherein the segments of the first PPA are in the order (i), (ia), (ib); and wherein the second PPA comprises a nucleic acid sequence comprising two segments, (i) a segment that binds to the second PPA binding site of the second TP, and (ii) a segment comprising a plurality of second PA-BSRs, wherein the second PA-BSRs comprise two segments, (iia) a segment comprising a binding site for the second PA and (iib) a segment comprising a binding site for the first PA, wherein the segments of the second PPA are in the order (i), (iia), (iib); (C) contacting the sample with a plurality of the first PAs and the second PAs, wherein the first PAs comprise a nucleic acid sequence comprising three segments, (i) a segment complementary to the second PA-BSR, (ii) a segment complementary to the first PA-BSR, and (iii) a segment comprising a plurality of amplifier binding segment repeats (AMP-BSRs); and wherein the second PAs comprise a nucleic acid sequence comprising three segments, (i) a segment complementary to the first PA-BSR, (ii) a segment complementary to the second PA-BSR, and (iii) a segment comprising a plurality of amplifier binding segment repeats (AMP-BSRs); (D) contacting the sample with a plurality of amplifiers (AMPs), wherein the AMPs comprise a nucleic acid sequence comprising two segments, (i) a segment complementary to the AMP-BSRs, and (ii) a segment comprising a plurality of label probe binding segment repeats (LP-BSRs); and (E) contacting the sample with a plurality of label probes (LPs), wherein the LPs comprise a nucleic acid sequence comprising two segments, (i) a segment complementary to the LP-BSRs, and (ii) a segment that is detectable; wherein the respective binding sites and complementary segments are hybridized to form a Signal Generating Complex (SGC), thereby detecting the target nucleic acid.

Embodiment 79. The method of embodiment 78, wherein the PPAs comprise base PPAs and extension PPAs.

Embodiment 80. The method of embodiment 78, wherein the PAs comprise base PAs and extension PAs.

Embodiment 81. The method of embodiment 78, wherein the AMPs comprise base AMPs and extension AMPs.

Embodiment 82. The method of any one of embodiments 78-81, wherein the base and extension molecules are tethered by a configuration comprising wherein the binding sites between the first base PPA and the first extension PPA and/or between the first extension PPAs comprise complementary sequences, and wherein the binding sites between the second base PPA and the second extension PPA and/or between the second extension PPAs comprise complementary sequences; and/or wherein the binding sites between the base PA and extension PA, and or the binding sites between the base AMP and extension AMP comprise complementary sequences.

Embodiment 83. The method of any one of embodiments 78-81, wherein the base and extension molecules are tethered by a configuration comprising wherein the composition further comprises a pair of bridges comprising a first bridge and second bridge, wherein the first bridge comprises two sections that bind to the first extension PPA binding site of the first base PPA and/or the first extension PPA binding site of the first extension PPA; and wherein the second bridge comprises two sections that bind to the second extension PPA binding site of the second base PPA and/or the second extension PPA binding site of the second extension PPA; wherein binding of the bridge tethers the extension PPA to the base PPA and/or the extension PPAs to each other; or wherein the composition further comprises a bridge, wherein the bridge comprises two sections that bind to the extension PA or AMP binding site of the base PA or AMP and/or the extension PA or AMP binding site of the extension PA or AMP, wherein binding of the bridge tethers the extension PA or AMP to the base PA or AMP and/or the extension PAs or AMPs to each other.

Embodiment 84. The method of any one of embodiments 78-81, wherein the base and extension molecules are tethered by a configuration comprising wherein the composition further comprises a pair of bridges comprising a first bridge and second bridge, wherein the first bridge comprises two sections, (i) a section that binds to the first extension PPA binding site of the first base PPA and/or the first extension PPA binding site of the first extension PPA, and (ii) a section that binds to the second extension PPA binding site of the second extension PPA; wherein the second bridge comprises two sections, (i) a section that binds to the second extension PPA binding site of the second base PPA and/or the second extension PPA binding site of the second extension PPA, and (ii) a section that binds to the first extension PPA binding site of the first extension PPA; wherein binding of the bridge tethers the second extension PPA to the first base PPA or the second extension PPA to the first extension PPA, and tethers the first extension PPA to the second base PPA or the first extension PPA to the second extension PPA.

Embodiment 85. The method of any one of embodiments 78-81, wherein the base and extension molecules are tethered by a configuration comprising wherein the first base PPA and/or the first extension PPA comprises a fourth segment (iv) comprising a binding site for the second extension PPA, and wherein the second base PPA and/or the second extension PPA comprises a fourth segment (iv) comprising a binding site for the first extension PPA, wherein the segments of the PPA are in the order (i), (ii), (iv), (iii).

Embodiment 86. The method of any one of embodiments 78-85, (I) wherein the first TP further comprises a third segment (iii) comprising a binding site for the second PPA; wherein the second TP further comprise a third segment (iii) comprising a binding site for the first PPA; and wherein the segments are in the order (i), (iii), (ii); and (II) wherein the first base PPA further comprises a fourth segment (iv) comprising a binding site for the second TP; wherein the second base PPA further comprises a fourth segment (iv) comprising a binding site for the first TP; wherein the segments are in the order (iv), (i), (ii), (iii); or wherein the first PPA further comprises a third segment (iii) comprising a binding site for the second TP; wherein the second PPA further comprises a third segment (iii) comprising a binding site for the first TP; wherein the segments are in the order (iii), (i), (ii).

Embodiment 87. The method of any one of embodiments 65-86, wherein the composition further comprises a second SGC, wherein the second SGC comprises a second target that is different from the target of embodiments 33-54, wherein the SGC comprises an SGC configuration of any one of embodiments 33-54 independently of the configuration of the first SGC, and wherein the second SGC is distinguishable from the first SGC.

Embodiment 88. The method of embodiment 87, wherein the composition further comprises a third SGC, wherein the third SGC comprises a third target that is different from the target of embodiments 65-86 and the second target, wherein the SGC comprises an SGC configuration of any one of embodiments 65-86 independently of the configuration of the first SGC and/or the second SGC, and wherein the third SGC is distinguishable from the first and second SGC.

Embodiment 89. The method of any one of embodiments 65-88, further comprising a target nucleic acid to which the pair of TPs bind.

Embodiment 90. The method of any one of embodiments 65-89, wherein the sample comprises a cell comprising the target nucleic acid.

Embodiment 91. A method of detecting a target nucleic acid, comprising (A) contacting a sample comprising a target nucleic acid with a pair of target probes (TPs), wherein a first TP of the pair of TPs comprises a nucleic acid sequence comprising two segments, (i) a segment comprising a binding site for a first segment of a target nucleic acid, and (ii) a segment comprising a binding site for a first base pre-pre-amplifier (base PPA); and wherein a second TP of the pair of TPs comprises a nucleic acid sequence comprising two segments, (i) a segment comprising a binding site for a second segment of the target nucleic acid, and (ii) a segment comprising a binding site for a second base PPA; (B) a pair of base PPAs comprising the first and second base PPAs, wherein the first base PPA comprises a nucleic acid sequence comprising three segments, (i) a segment that binds to the first base PPA binding site of the first TP, (ii) a segment comprising a plurality of first pre-amplifier binding segment repeats (first PA-BSRs), and (iii) a segment comprising a binding site for a first extension pre-pre-amplifier (extension PPA); and wherein the second base PPA comprises a nucleic acid sequence comprising three segments, (i) a segment that binds to the second base PPA binding site of the second TP, (ii) a segment comprising a plurality of second pre-amplifier binding segment repeats (second PA-BSRs), and (iii) a segment comprising a binding site for a second extension PPA; wherein the first and second PA-BSRs are different sequences; (C) a set of extension PPAs comprising the first and second extension PPAs, wherein the first extension PPA comprises a nucleic acid sequence comprising two segments, (i) a segment that binds to the first extension PPA binding site of the first base PPA, and (ii) a segment comprising a plurality of the first PA-BSRs; and wherein the second extension PPA comprises a nucleic acid sequence comprising two segments, (i) a segment that binds to the second extension PPA binding site of the second base PPA, and (ii) a segment comprising a plurality of the second PA-BSRs; (D) a plurality of pre-amplifiers (PAs), wherein the PAs comprise a nucleic acid sequence comprising three segments, (i) a segment complementary to the first PA-BSR, (ii) a segment complementary to the second PA-BSR, and (iii) a segment comprising a plurality of amplifier binding segment repeats (AMP-BSRs); (E) a plurality of amplifiers (AMPs), wherein the AMPs comprise a nucleic acid sequence comprising two segments, (i) a segment complementary to the AMP-BSRs, and (ii) a segment comprising a plurality of label probe binding segment repeats (LP-BSRs); and (F) a plurality of label probes (LPs), wherein the LPs comprise a nucleic acid sequence comprising two segments, (i) a segment complementary to the LP-BSRs, and (ii) a segment that is detectable; wherein the respective binding sites and complementary segments are hybridized to form a Signal Generating Complex (SGC), thereby detecting the target nucleic acid.

Embodiment 92. The method of embodiment 91, wherein the set of extension PPAs comprises at least one additional first extension PPA and at least one additional second extension PPA, wherein the additional first extension PPA comprises a nucleic acid sequence comprising two segments, (i) a segment comprising a binding site for the first extension PPA, and (ii) a segment comprising a plurality of the first PA-BSRs; wherein the additional second extension PPA comprises a nucleic acid sequence comprising two segments, (i) a segment comprising a binding site for the second extension PPA, and (ii) a segment comprising a plurality of the second PA-BSRs; and wherein the at least one additional first PPA optionally comprises a third segment (iii) comprising a second binding site for the first extension PPAs, and the at least one additional second PPA optionally comprises a third segment (iii) comprising a second binding site for the second extension PPAs.

Embodiment 93. The method of embodiment 91 or 92, wherein the binding sites between the first base PPA and the first extension PPA and/or between the extension PPAs comprise complementary sequences, and wherein the binding sites between the second base PPA and the second extension PPA and/or between the second extension PPAs comprise complementary sequences.

Embodiment 94. The method of embodiment 91 or 92, wherein the composition further comprises a pair of bridges comprising a first bridge and second bridge, wherein the first bridge comprises two sections that bind to the first extension PPA binding site of the first base PPA and/or the first extension PPA binding site of the first extension PPA; and wherein the second bridge comprises two sections that bind to the second extension PPA binding site of the second base PPA and/or the second extension PPA binding site of the second extension PPA; wherein binding of the bridge tethers the extension PPA to the base PPA and/or the extension PPAs to each other.

Embodiment 95. The method of embodiment 91 or 92, wherein the composition further comprises a pair of bridges comprising a first bridge and second bridge, wherein the first bridge comprises two sections, (i) a section that binds to the first extension PPA binding site of the first base PPA and/or the first extension PPA binding site of the first extension PPA, and (ii) a section that binds to the second extension PPA binding site of the second extension PPA; wherein the second bridge comprises two sections, (i) a section that binds to the second extension PPA binding site of the second base PPA and/or the second extension PPA binding site of the second extension PPA, and (ii) a section that binds to the first extension PPA binding site of the first extension PPA; wherein binding of the bridge tethers the second extension PPA to the first base PPA or the second extension PPA to the first extension PPA, and tethers the first extension PPA to the second base PPA or the first extension PPA to the second extension PPA.

Embodiment 96. The method of embodiment 91 or 92, wherein the first base PPA and/or the first extension PPA comprises a fourth segment (iv) comprising a binding site for the second extension PPA, and wherein the second base PPA and/or the second extension PPA comprises a fourth segment (iv) comprising a binding site for the first extension PPA.

Embodiment 97. A method of detecting a target nucleic acid, comprising (A) contacting a sample comprising a target nucleic acid with a pair of target probes (TPs), wherein a first TP of the pair of TPs comprises a nucleic acid sequence comprising two segments, (i) a segment comprising a binding site for a first segment of a target nucleic acid, and (ii) a segment comprising a binding site for a first pre-pre-amplifier (PPA); and wherein a second TP of the pair of TPs comprises a nucleic acid sequence comprising two segments, (i) a segment comprising a binding site for a second segment of the target nucleic acid, and (ii) a segment comprising a binding site for a second PPA; (B) a pair of PPAs comprising the first and second PPAs, wherein the first PPA comprises a nucleic acid sequence comprising two segments, (i) a segment that binds to the first PPA binding site of the first TP, and (ii) a segment comprising a plurality of first pre-amplifier binding segment repeats (first PA-BSRs); and wherein the second PPA comprises a nucleic acid sequence comprising two segments, (i) a segment that binds to the second PPA binding site of the second TP, and (ii) a segment comprising a plurality of second PA-BSRs, wherein the first and second PA-BSRs are different sequences; (C) a plurality of base pre-amplifiers (base PAs), wherein the base PAs comprise a nucleic acid sequence comprising four segments (i) a segment complementary to the first PA-BSRs, (ii) a segment complementary to the second PA-BSRs, (iii) a segment comprising a plurality of amplifier binding segment repeats (AMP-BSRs), and (iv) a segment that binds to an extension pre-amplifier (extension PA); (D) a plurality of extension PAs, wherein the extension PAs comprise a nucleic acid sequence comprising two segments (i) a segment that binds to the extension PA binding site of the base PAs and (ii) a plurality of amplifier binding segment repeats (AMP-BSRs); and wherein the extension PAs optionally comprise a third segment (iii) comprising a binding site for the extension PAs; (E) a plurality of amplifiers (AMPs), wherein the AMPS comprise a nucleic acid sequence comprising two segments, (i) a segment complementary to the AMP-BSRs, and (ii) a segment comprising a plurality of label probe binding segment repeats (LP-BSRs); and (F) a plurality of label probes (LPs), wherein the LPs comprise a nucleic acid sequence comprising two segments, (i) a segment complementary to the LP-BSRs, and (ii) a segment that is detectable; wherein the respective binding sites and complementary segments are hybridized to form a Signal Generating Complex (SGC), thereby detecting the target nucleic acid.

Embodiment 98. The method of embodiment 97, wherein the binding sites between the base PAs and the extension PAs comprise complementary sequences.

Embodiment 99. The method of embodiment 97, wherein the composition further comprises a bridge, wherein the bridge comprises two sections that bind to the extension PA binding site of the base PA and/or the extension PA binding site of the extension PA, wherein binding of the bridge tethers the extension PA to the base PA and/or the extension PAs to each other.

Embodiment 100. A method of detecting a target nucleic acid, comprising (A) contacting a sample comprising a target nucleic acid with a pair of target probes (TPs), wherein a first TP of the pair of TPs comprises a nucleic acid sequence comprising two segments, (i) a segment comprising a binding site for a first segment of a target nucleic acid, and (ii) a segment comprising a binding site for a first pre-pre-amplifier (PPA); and wherein a second TP of the pair of TPs comprises a nucleic acid sequence comprising two segments, (i) a segment comprising a binding site for a second segment of the target nucleic acid, and (ii) a segment comprising a binding site for a second PPA; (B) a pair of PPAs comprising the first and second PPAs, wherein the first PPA comprises a nucleic acid sequence comprising two segments, (i) a segment that binds to the first PPA binding site of the first TP, and (ii) a segment comprising a plurality of first pre-amplifier binding segment repeats (first PA-BSRs); and wherein the second PPA comprises a nucleic acid sequence comprising two segments, (i) a segment that binds to the second PPA binding site of the second TP, and (ii) a segment comprising a plurality of second PA-BSRs, wherein the first and second PA-BSRs are different sequences; (C) a plurality of pre-amplifiers (PAs), wherein the PAs comprise a nucleic acid sequence comprising three segments, (i) a segment complementary to the first PA-BSR, (ii) a segment complementary to the second PA-BSR, and (iii) a segment comprising a plurality of amplifier binding segment repeats (AMP-BSRs); (D) a plurality of base amplifiers (base AMPs), wherein the base AMPs comprise a nucleic acid sequence comprising three segments (i) a segment complementary to the AMP-BSRs, (ii) a segment comprising a plurality of label probe binding segment repeats (LP-BSRs), and (iii) a segment that binds to an extension amplifier (extension AMP); (E) a plurality of extension AMPs, wherein the extension AMPs comprise a nucleic acid sequence comprising two segments (i) a segment that binds to the extension AMP binding site of the base AMP, and (ii) a segment comprising a plurality of label probe binding segment repeats (LP-BSRs); and wherein the extension AMPs optionally comprise a third segment (iii) comprising a binding site for the extension PAs; (F) a plurality of label probes (LPs), wherein the LPs comprise a nucleic acid sequence comprising two segments (i) a segment complementary to the LP-BSRs, and (ii) a segment that is detectable; wherein the respective binding sites and complementary segments are hybridized to form a Signal Generating Complex (SGC), thereby detecting the target nucleic acid.

Embodiment 101. The method of embodiment 100, wherein the binding sites between the base AMPs and the extension AMPs comprise complementary sequences.

Embodiment 102. The method of embodiment 100, wherein the composition further comprises a bridge, wherein the bridge comprises two sections that bind to the extension AMP binding site of the base AMP and/or the extension AMP binding site of the extension AMP, wherein binding of the bridge tethers the extension AMP to the base AMP and/or the extension AMPs to each other.

Embodiment 103. The method of any one of embodiments 91-102: (I) wherein the first TP further comprises a third segment (iii) comprising a binding site for the second PPA; wherein the second TP further comprise a third segment (iii) comprising a binding site for the first PPA; and (II) wherein the first base PPA further comprises a fourth segment (iv) comprising a binding site for the second TP; wherein the second base PPA further comprises a fourth segment (iv) comprising a binding site for the first TP; or wherein the first PPA further comprises a third segment (iii) comprising a binding site for the second TP; wherein the second PPA further comprises a third segment (iii) comprising a binding site for the first TP.

Embodiment 104. A method of detecting a target nucleic acid, comprising (A) contacting a sample comprising a target nucleic acid with a pair of target probes (TPs), wherein a first TP of the pair of TPs comprises a nucleic acid sequence comprising two segments, (i) a segment comprising a binding site for a first segment of a target nucleic acid, and (ii) a segment comprising a binding site for a first base pre-pre-amplifier (base PPA); and wherein a second TP of the pair of TPs comprises a nucleic acid sequence comprising two segments, (i) a segment comprising a binding site for a second segment of the target nucleic acid, and (ii) a segment comprising a binding site for a second base PPA; (B) a pair of PPAs comprising the first and second PPAs, wherein the first PPA comprises a nucleic acid sequence comprising two segments, (i) a segment that binds to the first PPA binding site of the first TP, and (ii) a segment comprising a plurality of first pre-amplifier binding segment repeats (first PA-BSRs), wherein the first PA-BSRs comprise two segments, (ia) a segment comprising a binding site for a first pre-amplifier (first PA) and (ib) a segment comprising a binding site for a second PA; and wherein the second PPA comprises a nucleic acid sequence comprising two segments, (i) a segment that binds to the second PPA binding site of the second TP, and (ii) a segment comprising a plurality of second PA-BSRs, wherein the second PA-BSRs comprise two segments, (iia) a segment comprising a binding site for the second PA and (iib) a segment comprising a binding site for the first PA; (C) a plurality of the first PAs and the second PAs, wherein the first PAs comprise a nucleic acid sequence comprising three segments, (i) a segment complementary to the second PA-BSR, (ii) a segment complementary to the first PA-BSR, and (iii) a segment comprising a plurality of amplifier binding segment repeats (AMP-BSRs); and wherein the second PAs comprise a nucleic acid sequence comprising three segments, (i) a segment complementary to the first PA-BSR, (ii) a segment complementary to the second PA-BSR, and (iii) a segment comprising a plurality of amplifier binding segment repeats (AMP-BSRs); (D) a plurality of amplifiers (AMPs), wherein the AMPs comprise a nucleic acid sequence comprising two segments, (i) a segment complementary to the AMP-BSRs, and (ii) a segment comprising a plurality of label probe binding segment repeats (LP-BSRs); and (E) a plurality of label probes (LPs), wherein the LPs comprise a nucleic acid sequence comprising two segments, (i) a segment complementary to the LP-BSRs, and (ii) a segment that is detectable; wherein the respective binding sites and complementary segments are hybridized to form a Signal Generating Complex (SGC), thereby detecting the target nucleic acid.

Embodiment 105. The method of embodiment 104, wherein the PPAs comprise base PPAs and extension PPAs.

Embodiment 106. The method of embodiment 104, wherein the PAs comprise base PAs and extension PAs.

Embodiment 107. The method of embodiment 104, wherein the AMPs comprise base AMPs and extension AMPs.

Embodiment 108. The method of any one of embodiments 104-107, wherein the base and extension molecules are tethered by a configuration comprising: wherein the binding sites between the first base PPA and the first extension PPA and/or between the first extension PPAs comprise complementary sequences, and wherein the binding sites between the second base PPA and the second extension PPA and/or between the second extension PPAs comprise complementary sequences; and/or wherein the binding sites between the base PA and extension PA, and or the binding sites between the base AMP and extension AMP comprise complementary sequences.

Embodiment 109. The method of any one of embodiments 104-107, wherein the base and extension molecules are tethered by a configuration comprising: wherein the composition further comprises a pair of bridges comprising a first bridge and second bridge, wherein the first bridge comprises two sections that bind to the first extension PPA binding site of the first base PPA and/or the first extension PPA binding site of the first extension PPA; and wherein the second bridge comprises two sections that bind to the second extension PPA binding site of the second base PPA and/or the second extension PPA binding site of the second extension PPA; wherein binding of the bridge tethers the extension PPA to the base PPA and/or the extension PPAs to each other; or wherein the composition further comprises a bridge, wherein the bridge comprises two sections that bind to the extension PA or AMP binding site of the base PA or AMP and/or the extension PA or AMP binding site of the extension PA or AMP, wherein binding of the bridge tethers the extension PA or AMP to the base PA or AMP and/or the extension PAs or AMPs to each other.

Embodiment 110. The method of any one of embodiments 104-107, wherein the base and extension molecules are tethered by a configuration comprising: wherein the composition further comprises a pair of bridges comprising a first bridge and second bridge, wherein the first bridge comprises two sections, (i) a section that binds to the first extension PPA binding site of the first base PPA and/or the first extension PPA binding site of the first extension PPA, and (ii) a section that binds to the second extension PPA binding site of the second extension PPA; wherein the second bridge comprises two sections, (i) a section that binds to the second extension PPA binding site of the second base PPA and/or the second extension PPA binding site of the second extension PPA, and (ii) a section that binds to the first extension PPA binding site of the first extension PPA; wherein binding of the bridge tethers the second extension PPA to the first base PPA or the second extension PPA to the first extension PPA, and tethers the first extension PPA to the second base PPA or the first extension PPA to the second extension PPA.

Embodiment 111. The method of any one of embodiments 104-107, wherein the base and extension molecules are tethered by a configuration comprising: wherein the first base PPA and/or the first extension PPA comprises a fourth segment (iv) comprising a binding site for the second extension PPA, and wherein the second base PPA and/or the second extension PPA comprises a fourth segment (iv) comprising a binding site for the first extension PPA.

Embodiment 112. The method of any one of embodiments 104-111: (I) wherein the first TP further comprises a third segment (iii) comprising a binding site for the second PPA; wherein the second TP further comprise a third segment (iii) comprising a binding site for the first PPA; and (II) wherein the first base PPA further comprises a fourth segment (iv) comprising a binding site for the second TP; wherein the second base PPA further comprises a fourth segment (iv) comprising a binding site for the first TP; or wherein the first PPA further comprises a third segment (iii) comprising a binding site for the second TP; wherein the second PPA further comprises a third segment (iii) comprising a binding site for the first TP.

Embodiment 113. The method of any one of embodiments 91-112, wherein the composition further comprises a second SGC, wherein the second SGC comprises a second target that is different from the target of embodiments 91-112, wherein the SGC comprises an SGC configuration of any one of embodiments 91-112 independently of the configuration of the first SGC, and wherein the second SGC is distinguishable from the first SGC.

Embodiment 114. The method of embodiment 113, wherein the composition further comprises a third SGC, wherein the third SGC comprises a third target that is different from the target of embodiments 33-54 and the second target, wherein the SGC comprises an SGC configuration of any one of embodiments 33-54 independently of the configuration of the first SGC and/or the second SGC, and wherein the third SGC is distinguishable from the first and second SGC.

Embodiment 115. The method of any one of embodiments 91-114, further comprising a target nucleic acid to which the pair of TPs bind.

Embodiment 116. The method of any one of embodiments 91-115, further comprising a cell.

It is understood that modifications which do not substantially affect the activity of the various embodiments of this invention are also provided within the definition of the invention provided herein. Accordingly, the following examples are intended to illustrate but not limit the present invention.

Example 1

Detection of Nucleic Acids Using Amplification Molecule Extension

In a demonstration of one embodiment of a method of using amplification molecule extension, a single pair of target probes was hybridized to neighboring regions of a short nucleic acid sequence within the human RNA polymerase II subunit A (POLR2A) mRNA transcript in formalin-fixed paraffin-embedded HeLa cell sample. The pre-pre-amplifier layer was divided between multiple molecules. In FIG. 7A, the pre-pre-amplifier was divided into two distinct molecules (base PPA plus one extension PPA). The first pre-pre-amplifier hybridizes to the target probe, while the second anneals directly to the first pre-pre-amplifier to extend the PPA sequence and increase the number of pre-amplifier hybridization domains (binding segment repeats). In FIG. 7B, the pre-pre-amplifier was made up of three distinct molecules (base PPA plus two extension PPAs). The first pre-pre-amplifier hybridized to the target probe, the second hybridized directly to the first pre-pre-amplifier (as described in FIG. 3B), and the third hybridized directly to the second pre-pre-amplifier.

In this experiment, a single pair of target probes was used to detect a small region of the human POLR2A mRNA transcript in formalin-fixed, paraffin embedded cultured HeLa cells. Signal was amplified using a three-layered (three tiered) amplification system, with extension of the pre-preamplifier sequence by direct hybridization (as depicted in FIG. 3B). In the experiment shown in FIG. 7A, two pre-pre-amplifier molecules were joined by annealing directly to one another (base PPA plus extension PPA), increasing the number of binding segment repeats (BSRs) available for hybridization of pre-amplifier. In the experiment shown in FIG. 7B, three pre-pre-amplifier molecules were joined by annealing directly to one another (base PPA plus two extension PPAs), further increasing the number of binding segment repeats (BSRs) available for hybridization of pre-amplifiers, and therefore the amplification power and overall dot size generated by each SGC.

In this case, the resulting total pre-pre-amplifier sequence created with three molecules (base PPA plus two extension PPAs; FIG. 7B) is longer than the total pre-pre-amplifier sequence created with two molecules (base PPA plus one extension PPA; FIG. 7A), and the resulting increased number of pre-amplifier hybridization domains creates an overall larger SGC. This results in larger signal dots in FIG. 7B compared to FIG. 7A.

Example 2

Detection of Nucleic Acids Using Symmetric Amplification Molecules

In a demonstration of one embodiment of a method using symmetric amplification molecules to increase the amount of label probe within each SGC, a single pair of target probes was hybridized to neighboring regions of a short nucleic acid sequence within the human POLR2A mRNA transcript. A pre-pre-amplifier layer was hybridized to the target probe pair. Two distinct pre-amplifiers were symmetrically hybridized to the pre-pre-amplifier layer to allow the generation of an SGC with increased amplification power (see FIGS. 4 and 5).

In this experiment, a single pair of target probes detected a small region of the human POLR2A mRNA transcript in formalin-fixed, paraffin embedded cultured HeLa cells, and signal was amplified using a three-layered amplification system. In this example, symmetric collaborative hybridization was employed at the second layer of amplification, using two distinct pre-pre-amplifier molecules to create two symmetric collaborative hybridization sites, allowing for two distinct pre-amplifiers to bind in a balanced orientation, as depicted in FIG. 5.

Figure 8A:
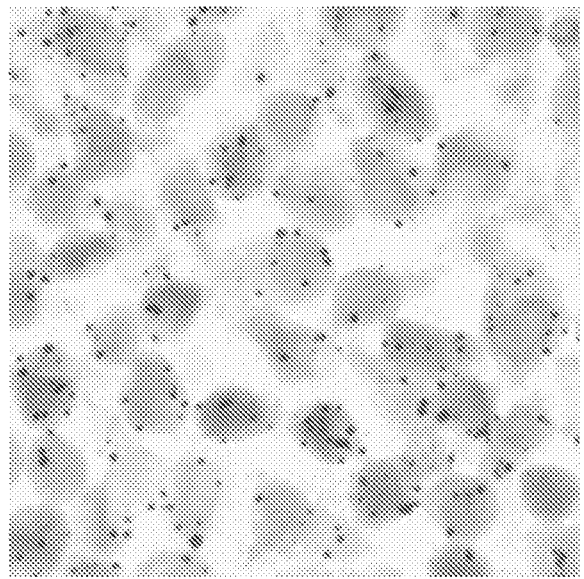
FIGS. 8A-8C show detection of nucleic acids by in situ hybridization using symmetric amplification molecules to increase the amount of label probe within each SGC.
Figure 8B:
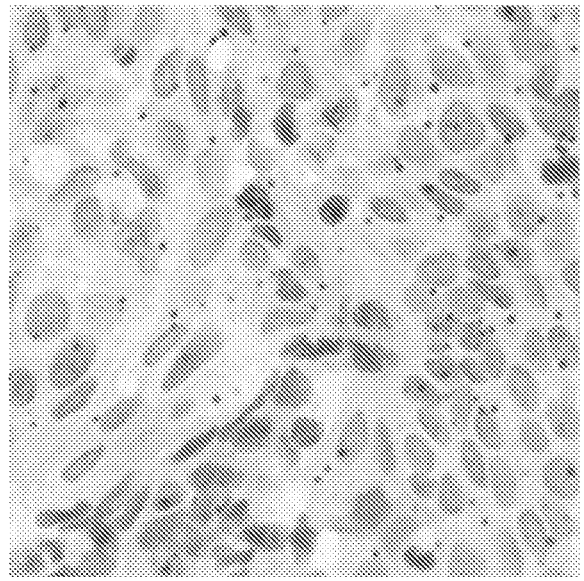
Figure 8C:
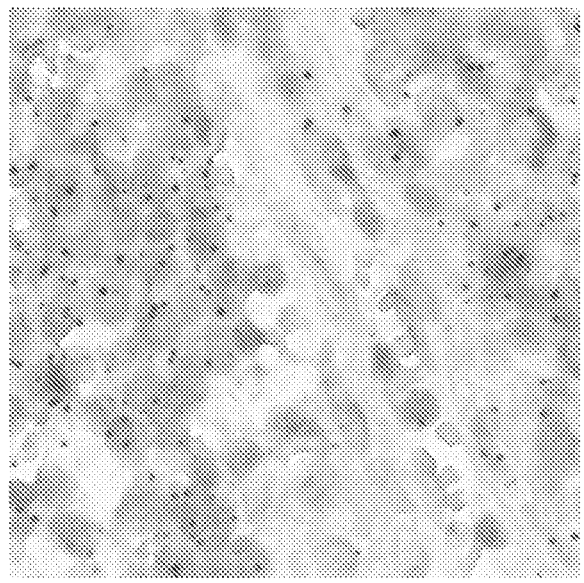

As shown in FIG. 8A, this embodiment was demonstrated in formalin-fixed paraffin-embedded HeLa cell sample. In FIG. 8B, this embodiment is demonstrated in a formalin-fixed paraffin-embedded human cervical cancer sample. In FIG. 8C, this embodiment is demonstrated in a formalin-fixed paraffin-embedded human tonsil sample.

Example 3

Detection of Multiple Nucleic Acid Targets within the Same Tissue Sample

In demonstration of the simultaneous detection of multiple target nucleic acids in the same sample, two distinct nucleic acid targets, human POLR2A (stained red) and human PPIB (stained green) were detected using one embodiment of the methods described herein, as exemplified in FIG. 6.

In the experiment shown in FIG. 9A, one pair of target probes detected the first target, a small region of the human RNA polymerase II subunit A (POLR2A) mRNA transcript (stained red), while another probe pair detected the second target, a small region of the human peptidylprolyl isomerase B (PPIB) mRNA transcript (stained green) in formalin-fixed, paraffin embedded cultured HeLa cells. Signal representing each target was amplified using a multi-layered amplification system with direct hybridization allowing for amplifier molecule extension (see FIG. 6). In FIG. 9B, the same signal amplification method was used to detect human POLR2A mRNA transcript (stained red) and human PPIB mRNA transcript (stained green) in a formalin-fixed, paraffin embedded human colon cancer tumor.

In the experiment shown in FIG. 9A, a single probe pair was used to detect each target in formalin-fixed paraffin-embedded HeLa cells. In FIG. 9B, a single probe pair was used to detect each target in formalin-fixed paraffin-embedded human colon cancer tissue. In each of FIGS. 9A and 9B, representative "red" staining is indicated with an upward pointing arrow, and representative "green" staining is indicated with a downward pointing arrow, with red and green staining observed throughout the images. Both the POLR2A and PPIB mRNAs were detected in Hela cells and human colon cancer tissue in the same sample.

Throughout this application various publications have been referenced. The disclosures of these publications in their entireties are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A composition comprising a Signal Generating Complex (SGC), wherein the composition comprises:
   (A) a pair of target probes (TPs), wherein a first TP of the pair of TPs comprises a nucleic acid sequence comprising two segments, (i) a segment comprising a binding site for a first segment of a target nucleic acid, and (ii) a segment comprising a binding site for a first base pre-pre-amplifier (PPA); and wherein a second TP of the pair of TPs comprises a nucleic acid sequence comprising two segments, (i) a segment comprising a binding site for a second segment of the target nucleic acid, and (ii) a segment comprising a binding site for a second base PPA;
   (B) a pair of base PPAs comprising the first base PPA and the second base PPA, wherein the first base PPA comprises a nucleic acid sequence comprising three segments, (i) a segment that binds the first TP, (ii) a segment comprising a plurality of first preamplifier binding segment repeats (PA-BSRs), and (iii) a segment comprising a binding site for a first extension pre-pre-amplifier (PPA); and wherein the second base PPA comprises a nucleic acid sequence comprising three segments, (i) a segment that binds the second TP, (ii) a segment comprising a plurality of second PA-BSRs, and (iii) a segment comprising a binding site for a second extension PPA; wherein the first PA-BSRs and the second PA-BSRs are different sequences, and wherein the segments of each of the first base PPA and the second base PPA are in the order (i), (ii), and (iii) and the order is either from 5' to 3' or 3' to 5' for the first base PPA and either from 5' to 3' or 3' to 5' for the second base PPA;
   (C) a set of extension PPAs comprising the first extension PPA and the second extension PPA, wherein the first extension PPA comprises a nucleic acid sequence comprising two segments, (i) a segment that binds to the first base PPA, and (ii) a segment comprising a plurality of the first PA-BSRs; and wherein the second extension PPA comprises a nucleic acid sequence comprising two segments, (i) a segment that binds to the second base PPA, and (ii) a segment comprising a plurality of the second PA-BSRs;
   (D) a plurality of pre-amplifiers (PAs), wherein the PAs comprise a nucleic acid sequence comprising three segments, (i) a segment complementary to the first PA-BSR, (ii) a segment complementary to the second PA-BSR, and (iii) a segment comprising a plurality of amplifier binding segment repeats (AMP-BSRs); wherein the segments of each of the plurality of PAs are in the order (i), (ii), and (iii) and the order is either from 5' to 3' or 3' to 5' for each of the plurality of PAs;
   (E) a plurality of amplifiers (AMPs), wherein the AMPs comprise a nucleic acid sequence comprising two segments, (i) a segment complementary to the AMP-BSRs, and (ii) a segment comprising a plurality of label probe binding segment repeats (LP-BSRs); and
   (F) a plurality of label probes (LPs), wherein the LPs comprise a nucleic acid sequence comprising two segments, (i) a segment complementary to the LP-BSRs, and (ii) a segment that is detectable;
   wherein the SGC is formed by combining items (A) to (E) and the target nucleic acid together.

2. The composition of claim 1, wherein the set of extension PPAs comprises at least one additional first extension PPA and at least one additional second extension PPA, wherein the additional first extension PPA comprises a nucleic acid sequence comprising two segments, (i) a segment comprising a binding site for the first extension PPA, and (ii) a segment comprising a plurality of the first PA-BSRs; wherein the additional second extension PPA comprises a nucleic acid sequence comprising two segments, (i) a segment comprising a binding site for the second extension PPA, and (ii) a segment comprising a plurality of the second PA-BSRs; and wherein the at least one additional first PPA optionally comprises a third segment (iii) comprising a second binding site for the first extension PPAs, and the at least one additional second PPA optionally comprises a third segment (iii) comprising a second binding site for the second extension PPAs, wherein the segments of each of the at least one additional first PPA and the at least one additional second PPA are in the order (i), (ii), and (iii) when each of the at least one additional first PPA and the at least one additional second PPAs comprises (iii) and the order is either from 5' to 3' or 3' to 5' for the at least one additional first PPA and either from 5' to 3' or 3' to 5' for the at least one additional second PPA.

3. The composition of claim 1, wherein the composition further comprises a pair of bridges comprising a first bridge and second bridge, wherein the first bridge comprises two sections that bind to the first base PPA and the first extension PPA, respectively; and wherein the second bridge comprises two sections that bind to the second base PPA and the second extension PPA, respectively; wherein binding of the first bridge to the first base PPA and the first extension PPA tethers the first base PPA to the first extension PPA, and binding of the second bridge to the second base PPA and the second extension PPA tethers the second base PPA to the second extension PPA.

4. The composition of claim 1, wherein the composition further comprises a pair of bridges comprising a first bridge and second bridge, wherein the first bridge comprises two sections, (i) a section that binds to the first base PPA or the first extension PPA, and (ii) a section that binds to the second extension PPA; wherein the second bridge comprises two sections, (i) a section that binds to the second base PPA or the second extension PPA, and (ii) a section that binds to the first extension PPA; wherein binding of the first bridge to the first base PPA or the first extension PPA and the second extension PPA tethers the second extension PPA to the first base PPA or the second extension PPA to the first extension PPA, and binding of the second bridge to the second base PPA or the second extension PPA and the first extension PPA tethers the first extension PPA to the second base PPA or the first extension PPA to the second extension PPA.

5. The composition of claim 1, wherein the first base PPA and/or the first extension PPA comprises a fourth segment (iv) comprising a binding site for the second extension PPA, and wherein the second base PPA and/or the second extension PPA comprises a fourth segment (iv) comprising a binding site for the first extension PPA, wherein the segments of each of the first base PPA and the second base PPA are in the order (i), (ii), (iv), and (iii) when each of the first base PPA and the second base PP A comprises (iv) and the order is either from 5' to 3' or 3' to 5' for the first base PPA and either from 5' to 3' or 3' to 5' for the second base PPA, and the segments of each of the first extension PPA and the second extension PPA are in the order (i), (ii), (iv), and (iii) if each of the first extension PPA and the second extension PPA comprises (iv) and the order is either from 5' to 3' or 3' to 5' for the first extension PPA and either from 5' to 3' or 3' to 5' for the second extension PPA.

6. The composition of claim 1:
(I) wherein the first TP further comprises a third segment (iii) comprising a binding site for the second base PPA; wherein the second TP further comprise a third segment (iii) comprising a binding site for the first base PPA; and wherein the segments of each of the first TP and the second TP are in the order (i), (iii), and (ii) and the order is either from 5' to 3' or 3' to 5' for the first TP and either from 5' to 3' or 3' to 5' for the second TP; and
(II) wherein the first base PPA further comprises a fourth segment (iv) comprising a binding site for the second TP; wherein the second base PPA further comprises a fourth segment (iv) comprising a binding site for the first TP; wherein the segments of the first base PPA and the second base PPA are in the order (iv), (i), (ii), and (iii) and the order is either from 5' to 3' or 3' to 5' for the first base PPA and either from 5' to 3' or 3' to 5' for the second base PPA; or
wherein the first extension PPA further comprises a third segment (iii) comprising a binding site for the second TP; wherein the second extension PPA further comprises a third segment (iii) comprising a binding site for the first TP; wherein the segments of each of the first extension PPA and the second extension PPA are in the order (iii), (i), and (ii) and the order is either from 5' to 3' or 3' to 5' for the first extension PPA and either from 5' to 3' or 3' to 5' for the second extension PPA.

7. The composition of claim 1, wherein the SGC of claim 1 is a first SGC and the composition further comprises a second SGC, wherein the second SGC comprises and target nucleic acid that is different from the target nucleic acid of claim 1, wherein the second SGC has a similar configuration of the first SGC of claim 1 and the configuration of the second SGC is distinguishable from the configuration of the first SGC.

8. The composition of claim 7, wherein the composition further comprises a third SGC, wherein the third SGC comprises a target nucleic acid that is different from the target nucleic acid of claim 1 and the second target nucleic acid, wherein the third SGC has a similar configuration of the first SGC configuration of claim 1 and/or has a similar configuration of the second SGC, and wherein the configuration of the third SGC is distinguishable from the configuration of the first SGC and the configuration of the second SGC.

9. The composition of claim 1, further comprising the target nucleic acid.

10. The composition of claim 1, further comprising a cell.

11. A composition comprising a Signal Generating Complex (SGC), wherein the composition comprises:
(A) a pair of target probes (TPs), wherein a first TP of the pair of TPs comprises a nucleic acid sequence comprising two segments, (i) a segment comprising a binding site for a first segment of a target nucleic acid, and (ii) a segment comprising a binding site for a first base pre-pre-amplifier (PPA); and wherein a second TP of the pair of TPs comprises a nucleic acid sequence comprising two segments, (i) a segment comprising a binding site for a second segment of the target nucleic acid, and (ii) a segment comprising a binding site for a second base PPA;
(B) a pair of PPAs comprising the first PPA and the second PPA, wherein the first PPA comprises a nucleic acid sequence comprising two segments, (i) a segment that binds to the first TP, and (ii) a segment comprising a plurality of first pre-amplifier binding segment repeats (PA-BSRs), wherein the first PA-BSRs comprise two segments, (ia) a segment comprising a binding site for a first pre-amplifier (PA) and (ib) a segment comprising a binding site for a second PA, wherein the segments of the first PPA are in the order (i), (ia), and (ib); and wherein the second PPA comprises a nucleic acid sequence comprising two segments, (i) a segment that binds the second TP, and (ii) a segment comprising a plurality of second PA-BSRs, wherein the second PA-BSRs comprise two segments, (iia) a segment comprising a binding site for the second PA and (iib) a segment comprising a binding site for the first PA, wherein the segments of the second PPA are the order (i), (iia), and (iib) and the order is either from 5' to 3' or 3' to 5' for the first PPA and either from 5' to 3' or 3' to 5' for the second PPA;

(C) a plurality of the first PAs and a plurality of the second PAs, wherein the first PAs comprise a nucleic acid sequence comprising three segments, (i) a segment complementary to the second PA-BSR, (ii) a segment complementary to the first PA-BSR, and (iii) a segment comprising a plurality of amplifier binding segment repeats (AMP-BSRs); and wherein the second PAs comprises a nucleic acid sequence comprising three segments, (i) a segment complementary to the first PA-BSR, (ii) a segment complementary to the second PA-BSR, and (iii) a segment comprising a plurality of amplifier binding segment repeats (AMP-BSRs);

(D) a plurality of amplifiers (AMPs), wherein the AMPs comprise a nucleic acid sequence comprising two segments, (i) a segment complementary to the AMP-BSRs, and (ii) a segment comprising a plurality of label probe binding segment repeats (LP-BSRs); and (E) a plurality of label probes (LPs), wherein the LPs comprise a nucleic acid sequence comprising two segments, (i) a segment complementary to the LP-BSRs, and (ii) a segment that is detectable;

wherein the SGC is formed by combining items (A) to (E) and the target nucleic acid together.

12. The composition of claim 11, wherein the pairs of PPAs comprise base PPAs and extension PPAs; wherein the first PAs and the second PAs comprise base PAs and extension PAs; and/or wherein the plurality of AMPs comprise base AMPs and extension AMPs.

13. A method of detecting a target nucleic acid in a sample, the method comprising contacting the sample comprising the target nucleic acid with items (A) to (F) of claim 1; assembling the SGC by mixing items (A) to (F) with the target nucleic acid in the sample; and detecting the target nucleic acid in the sample.

14. A kit for assembling the SGC of claim 1, wherein the kit comprises items (A) to (F) of claim 1.

15. A sample for fixed and permeabilized cells comprising the SGC of claim 1.

* * * * *